United States Patent
Wipf et al.

(10) Patent No.: US 8,288,551 B2
(45) Date of Patent: Oct. 16, 2012

(54) TARGETED NITROXIDE AGENTS

(75) Inventors: Peter Wipf, Pittsburgh, PA (US); Marie Celine Frantz, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 621 days.

(21) Appl. No.: 12/505,294

(22) Filed: Jul. 17, 2009

(65) Prior Publication Data

US 2010/0035869 A1     Feb. 11, 2010

Related U.S. Application Data

(60) Provisional application No. 61/081,585, filed on Jul. 17, 2008, provisional application No. 61/158,569, filed on Mar. 9, 2009, provisional application No. 61/178,570, filed on May 15, 2009.

(51) Int. Cl.
*C07D 211/00*     (2006.01)
*A61K 31/445*     (2006.01)

(52) U.S. Cl. ........................... 546/242; 514/315

(58) Field of Classification Search .................. 546/242; 514/315
See application file for complete search history.

(56) References Cited

U.S. PATENT DOCUMENTS

| | | | |
|---|---|---|---|
| 7,528,174 | B2 | 5/2009 | Wipf et al. |
| 7,718,603 | B1 | 5/2010 | Wipf et al. |
| 2007/0161544 | A1 | 7/2007 | Wipf et al. |
| 2007/0161573 | A1 | 7/2007 | Wipf et al. |
| 2011/0039792 | A1 | 2/2011 | Wipf et al. |
| 2011/0172214 | A1 | 7/2011 | Wipf et al. |
| 2012/0004263 | A1 | 1/2012 | Niedernhofer et al. |

OTHER PUBLICATIONS

Fink et al., "Hemigramicidin-TEMPO conjugates: Novel mitochondria-targeted anti-oxidants," *Biochemical Pharmacology* 74(6):801-809, Sep. 15, 2007.
Hahn et al., "Tempol, a Stable Free Radical, Is a Novel Murine Radiation Protector," *Cancer Research* 52:1750-1753, 1992.
Jiang et al., "Structural Requirements for Optimized Delivery, Inhibition of Oxidative Stress, and Antiapoptotic Activity of Targeted Nitroxides," *The Journal of Pharmacology and Experimental Therapeutics* 320(3):1050-1060, Mar. 1, 2007.
Macias et al., "Treatment with a Novel Hemigramicidin-TEMPO Conjugate Prolongs Survival in a Rat Model of Lethal Hemorrhagic Shock," *Annals of Surgery* 245(2):305-314, Feb. 1, 2007.
Mitchell et al., "Radiation, Radicals, and Images," *Annals New York Academy of Sciences* 899:28-43, 2000.
Wipf et al., "Convergent Approach to ($E$)-Alkene and Cyclopropane Peptide Isosteres," *Organic Letters* 7(1):103-106, 2005.
Wipf et al., "Mitochondrial Targeting of Selective Electron Scavengers: Synthesis and Biological Analysis of Hemigramicidin— TEMPO Conjugates," *JACS* 127(36):12460-12461, Sep. 1, 2005 (Published online Aug. 15, 2005).
European Supplemental Search Report from corresponding European Application No. 09798808.3 dated Feb. 22, 2012.
International Search Report from PCT Application No. PCT/US2009/051004, mailed Mar. 12, 2010.
Written Opinion of the International Search Authority from PCT Application No. PCT/US2009/051004, mailed Mar. 12, 2010.
International Preliminary Report on Patentability from PCT Application No. PCT/US2009/051004, dated Jan. 18, 2011.

*Primary Examiner* — Janet Andres
*Assistant Examiner* — John Mabry
(74) *Attorney, Agent, or Firm* — Klarquist Sparkman, LLP

(57) ABSTRACT

Provided herein are compositions and related methods useful for free radical scavenging, with particular selectivity for mitochondria. The compounds comprise a nitroxide-containing group attached to a mitochondria-targeting group. The compounds can be cross-linked into dimers without loss of activity. Also provided herein are methods, for preventing, mitigating and treating damage caused by radiation. The method comprises delivering a compound, as described herein, to a patient in an amount and dosage regimen effective to prevent, mitigate or treat damage caused by radiation.

22 Claims, 39 Drawing Sheets

TEMPOL

XJB-5-133

XJB-5-208

XJB-2-300

XJB-2-70

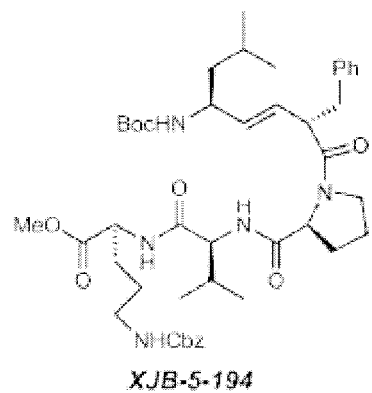
XJB-5-194
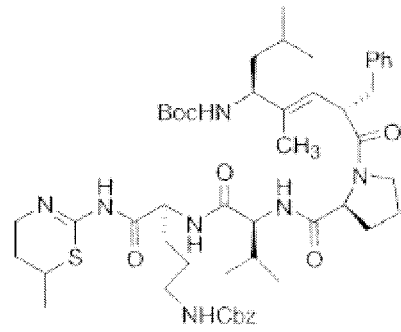
XJB-5-241
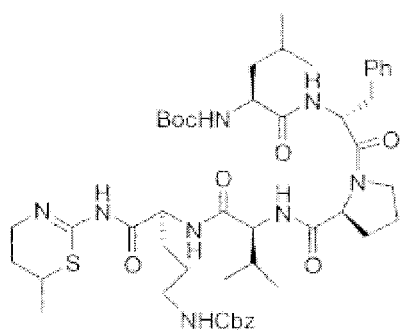
XJB-5-127
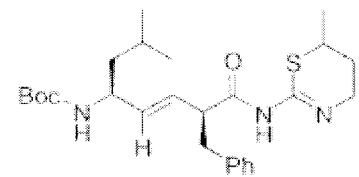
XJB-5-234
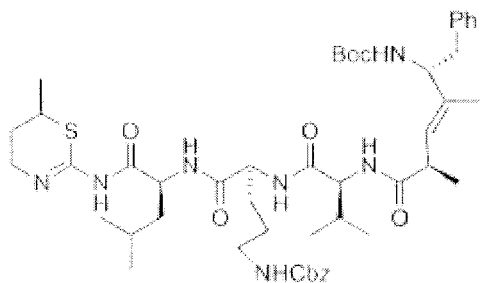
XJB-7-42
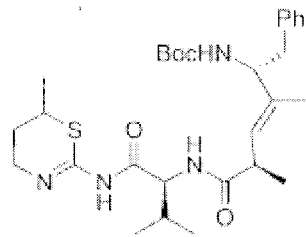
XJB-7-43
*Fig. 2-3*

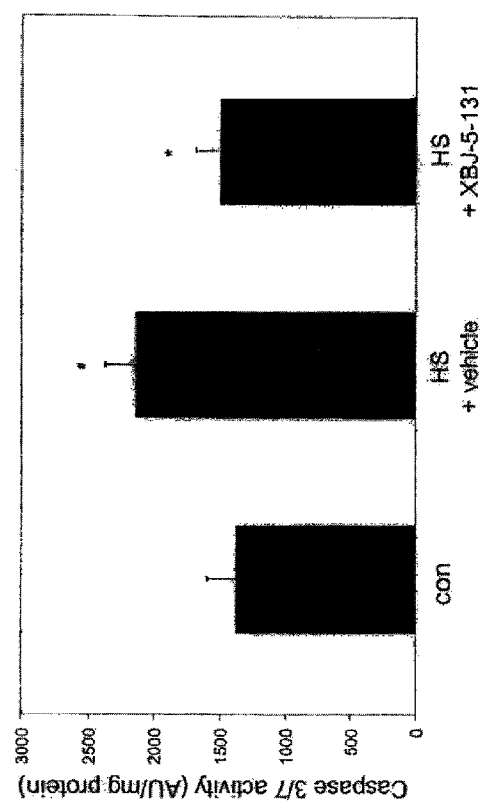
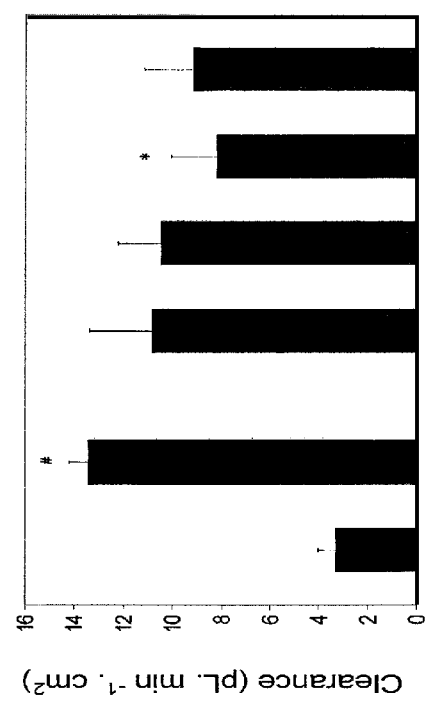
Fig. 8
Fig. 9

| | XJB | n | Oil | n |
|---|---|---|---|---|
| Dystonia | 8.7 | 5 | 6.8 | 3 |
| Trembling | 9.8 | 5 | 8.5 | 3 |
| Kyphosis | 12.6 | 5 | 10.8 | 3 |
| Ataxia | 17.1 | 5 | 13.2 | 3 |
| Wasting | 16.5 | 5 | 14.2 | 3 |
| Eyes | 22.0 | 1 | 14.3 | 2 |
| Priapism | 17.0 | 1 | 17.6 | 2 |
| Decreased activity | 22.4 | 3 | 17.0 | 3 |
| Incontinence | | 3 | 12.4 | 2 |
| AGING SCORE (delay in onset of symptoms) | 90% | 5 | 10% | 3 |
| | $p \leq 0.05$ | | | |

TARGETED NITROXIDE AGENTS

CROSS REFERENCE TO RELATED APPLICATIONS

This application claims the benefit under 35 U.S.C. §119 (e) to U.S. Provisional Patent Application Nos. 61/081,585, filed on Jul. 17, 2008; 61/158,569, filed on Mar. 9, 2009; and 61/178,570, filed on May 15, 2009, each of which is incorporated herein by reference in its entirety.

STATEMENT REGARDING FEDERAL FUNDING

The U.S. Government has a paid-up license in this invention and the right in limited circumstances to require the patent owner to license others on reasonable terms as provided for by the terms of Grant No. GM067082, awarded by the National Institutes of Health and Grant No. W81XWH-05-2-0026, awarded by the Defense Advanced Research Projects Agency.

Provided herein are novel compounds and compositions of matter comprising a nitroxide group-containing cargo (or "nitroxide containing group") and a mitochondria-targeting group (or "targeting group"). The targeting group is believed, without any intent to be bound, to have the ability to selectively deliver the composition to mitochondrial, delivering the antioxidant and free-radical scavenging activity of the nitroxide group to cells, including but not limited to an enrichment in mitochondria. These compounds are useful, generally, for their anti-oxidant and free-radical scavenging capacity, and, more specifically, for example and without limitation, for their radioprotective abilities and prevention as well as mitigation of degenerative diseases.

Oxidation stress in cells typically manifests itself by way of generating reactive oxygen species ("ROS") and reactive nitrogen species ("RNS"). Specifically, the cellular respiration pathway generates ROS and RNS within the mitochondrial membrane of the cell, see Kelso et al., Selective Targeting of a Redox-active Ubiquinone to Mitochondria within Cells: Antioxidant and Antiapoptotic Properties, J Biol. Chem. 276:4588 (2001). Reactive oxygen species include free radicals, reactive anions containing oxygen atoms, and molecules containing oxygen atoms that can either produce free radicals or are chemically activated by them. Specific examples include superoxide anion, hydroxyl radical, and hydroperoxides. In many disease states, the normal response to ROS and RNS generation is impaired.

Naturally occurring enzymes, such as superoxide dismutase ("SOD") and catalase salvage ROS and RNS radicals to allow normal metabolic activity to occur. Significant deviations from cell homeostasis, such as hemorrhagic shock, lead to an oxidative stress state, thereby causing "electron leakage" from the mitochondrial membrane. This "electron leakage" produces an excess amount of ROS for which the cell's natural antioxidants cannot compensate. Specifically, SOD cannot accommodate the excess production of ROS associated with hemorrhagic shock which ultimately leads to premature mitochondria dysfunction and cell death via apoptosis, see Kentner et al., Early Antioxidant Therapy with TEMPOL during Hemorrhagic Shock Increases Survival in Rats, J Trauma Inj Infect Crit. Care., 968 (2002).

Cardiolipin ("CL") is an anionic phospholipid exclusively found in the inner mitochondrial membrane of eukaryotic cells, see Iverson, S. L. and S. Orrenius, The cardiolipincy-tochrome c interaction and the mitochondria) regulation of apoptosis, Arch Biochem. 423:37-46 (2003). Under normal conditions, the pro-apoptotic protein cytochrome c is anchored to the mitochondrial inner membrane by binding with CL, see Tuominen, E. K. J., et al. Phospholipid cytochrome c interaction: evidence for the extended lipid anchorage, J Biol. Chem., 277:8822-8826 (2002). The acyl moieties of CL are susceptible to peroxidation by reactive oxygen species. When ROS are generated within mitochondria in excess quantities, cytochrome C bound to CL can function as an oxidase and induces extensive peroxidation of CL in the mitochondrial membrane, see Kagan, V. E. et al., Cytochrome c acts as a cardiolipin oxygenase required, for release of proapoptotic, factors, Nat Chem Biol. 1:223-232 (2005); also Kagan, V. E. et al., Oxidative lipidomics of apoptosis: redox catalytic interactions of cytochrome c with cardiolipin and phosphatidylserine, Free Rad Biol Med. 37:1963-1985 (2005).

The peroxidation of the CL weakens the binding between the CL and cytochrome C, see Shidoji, Y. et al., Loss of molecular interaction between cytochrome C and cardiolipin due to lipid peroxidation, Biochem Biophys Res Comm. 264: 343-347 (1999). This leads to the release of the cytochrome C into the mitochondrial intermembrane space, inducing apoptotic cell death. Further, the peroxidation of CL has the effect of opening the mitochondrial permeability transition pore ("MPTP"), see Dolder, M. et al., Mitochondria creatine kinase in contact sites: Interaction with porin and adenine nucleotide translocase, role in permeability transition and sensitivity to oxidative damage, Biol Sign Recept., 10:93-111 (2001); also Imai, H. et al., Protection from inactivation of the adenine nucleotide translocator during hypoglycaemia-induced apoptosis by mitochondria/phospholipid hydroperoxide glutathione peroxidase, Biochem J., 371:799-809 (2003). Accordingly, the mitochondrial membrane swells and releases the cytochrome C into the cytosol. Excess cytochrome C in the cytosol leads to cellular apoptosis, see Iverson, S. L. et al. The cardiolipin-cytochrome c interaction and the mitochondria regulation of apoptosis, Arch Biochem Biophys. 423:37-46 (2003).

Moreover, mitochondrial dysfunction and cell death may ultimately lead to multiple organ failure despite resuscitative efforts or supplemental oxygen supply, see Cairns, C., Rude Unhinging of the Machinery of Life: Metabolic approaches to hemorrhagic Shock, Curr Crit. Care., 7:437 (2001). Accordingly, there is a need in the art for an antioxidant which scavenges the ROS, thereby reducing oxidative stress. Reduction of oxidative stress delays, even inhibits, physiological conditions that otherwise might occur, such as hypoxia.

Also, there is also a need to improve the permeability of antioxidants' penetration of the cellular membrane. One of the limitations of SOD is that it cannot easily penetrate the cell membrane. However, nitroxide radicals, such as TEMPO (2,2,6,6-tetramethylpiperidine-N-oxyl) and its derivatives, have been shown to penetrate the cell membrane better than SOD. Further, nitroxide radicals like, for example and without limitation, TEMPO prevent the formation of ROS, particularly superoxide, due to their reduction by the mitochondrial electron transport chain to hydroxylamine radical scavengers, see Wipf, P. et al., Mitochondria targeting of selective electron scavengers: synthesis and biological analysis of hemigramicidin-TEMPO conjugates, J Am Chem Soc. 127:12460-12461. Accordingly, selective delivery of TEMPO derivatives may lead to a therapeutically beneficial reduction of ROS and may delay or inhibit cell death due to the reduction of oxidative stress on the cell.

Selective delivery may be accomplished by way of a number of different pathways—e.g., by a biological or chemical moiety having a specific targeting sequence for penetration of the cell membrane, ultimately being taken up by the mitochondrial membrane. Selective delivery of a nitroxide SOD mimic into the mitochondrial membrane has proven difficult. Accordingly, there is a need in the art for effective and selective delivery of antioxidants that specifically target the mitochondria and its membranes as well as inter-membrane space to help reduce the ROS and RNS species. The antioxidants also help prevent cellular and mitochondria apoptotic activity which often results due to increased ROS species, see Kelso et al., Selective Targeting of a Redox-active Ubiquinone to Mitochondria within Cells: Antioxidant and Antiapoptotic Properties, J Biol Chem., 276: 4588 (2001). Examples of mitochondria-targeting antioxidants are described in United States Patent Publication Nos. 20070161573 and 20070161544.

There remains a very real need for a composition and associated methods for delivering cargo of various types to mitochondria. In one embodiment, a composition comprising membrane active peptidyl fragments having a high affinity with the mitochondria linked to cargo is provided. The cargo may be selected from a large group of candidates. There is a need for compositions and methods for effectively treating a condition that is caused by excessive mitochondria production of ROS and RNS in the mitochondrial membrane. There also is a need for compounds that can protect cells and tissues of animals against radiation damage.

Radiation Exposure

The biologic consequences of exposure to ionizing radiation (IR) include genomic instability and cell death (Little J B, Nagasawa H, Pfenning T, et al Radiation-induced genomic instability: Delayed mutagenic and cytogenetic effects of X rays and alpha particles. Radiat Res 1997; 148:299-307). It is assumed that radiolytically generated radicals are the primary cause of damage from IR. Direct radiolysis of water and the secondary reactive intermediates with a short lifetime ($10^{-10}$-$10^{-6}$ seconds) mediate the chemical reactions that trigger the damage of cellular macromolecules, including DNA and proteins, as well as phospholipids in membranes (Mitchell J B, Russo A, Kuppusamy P, et al. Radiation, radicals, and images. Ann NY Acad Sci 2000; 899:28-43). The DNA is believed to be the primary target for the radical attack, resulting in single and double DNA strand breaks (Bryant P E. Enzymatic restriction of mammalian cell DNA: Evidence for double-strand breaks as potentially lethal lesions. Int J Radiat Biol 1985; 48:55-60). To maintain the genomic integrity, multiple pathways of DNA repair and cell-cycle checkpoint control are activated in response to irradiation-induced DNA damage (Elledge S J. Cell cycle checkpoints: Preventing an identity crisis. Science 1996; 274:1664-1672). Failure of these repair and regulatory systems leads to genotoxicity, malignant transformation, and cell death (Sachs R K, Chen A M, Brenner D J. Proximity effects in the production of chromosome aberrations by ionizing radiation. Int J Radiat Biol 1997; 71:1-19).

One of the major mechanisms of IR-induced cell death is apoptosis, most commonly realized through a mitochondria-dependent intrinsic pathway (Newton K, Strasser A. Ionizing radiation and chemotherapeutic drugs induce apoptosis in lymphocytes in the absence of Fas or FADD/MORT1 signaling. Implications for cancer therapy. J Exp Med 2000; 191: 195-200). The latter includes permeabilization of mitochondria followed by the release of cytochrome (cyt) c and other proapoptotic factors (Smac/Diablo [second mitochondrial-derived activator of caspase/direct inhibitor of apoptosis-binding protein with low pI], EndoG [endonuclease G], Omi/HtrA2, and AIF [apoptosisinducing factor]) into the cytosol as the key events in the execution of the death program. The released cyt c facilitates the formation of apoptosomes by interacting with apoptotic protease activating factor 1 (Apaf-1) and then recruits and activates procaspase-9 and triggers the proteolytic cascade that ultimately leads to cell disintegration. Release of proapoptotic factors and caspase activation designate the commencement of irreversible stages of apoptosis. Therefore, significant drug discovery efforts were directed toward the prevention of these events, particularly of the mitochondrial injury representing an important point of no return (Szewczyk A, Wojtczak L. Mitochondria as a pharmacological target. Pharmacol Rev 2002; 54:101-127). However, the exact mechanisms of cyt c release from mitochondria are still poorly understood. It was postulated that generation of reactive oxygen species (ROS), likely by means of disrupted electron transport, has a crucial role in promoting cyt c release from mitochondria (Kowaltowski A J, Castilho R F, Vercesi A E. Opening of the mitochondrial permeability transition pore by uncoupling or inorganic phosphate in the presence of Ca2+ is dependent on mitochondrial-generated reactive oxygen species. FEBS Lett 1996; 378:150-152). Notably, ROS can induce mitochondria membrane permeabilization both in vitro and in vivo, and the mitochondrial membrane transition pore was shown to be redox sensitive (Kroemer G, Reed J C. Mitochondrial control of cell death. Nat Med 2000; 6:513-519).

Conversely, antioxidants and reductants, overexpression of manganese superoxide dismutase (MnSOD) (Wong G H, Elwell J H, Oberley L W, et al. Manganous superoxide dismutase is essential for cellular resistance to cytotoxicity of tumor necrosis factor. Cell 1989; 58:923-931), and thioredoxin (Iwata S, Hori T, Sato N, et al. Adult T cell leukemia (ATL)-derived factor/human thioredoxin prevents apoptosis of lymphoid cells induced by L-cystine and glutathione depletion: Possible involvement of thiol-mediated redox regulation in apoptosis caused by pro-oxidant state. J Immunol 1997; 158:3108-3117) can delay or inhibit apoptosis. Previous studies showed that early in apoptosis, a mitochondria-specific phospholipid-cardiolipin (CL) translocated from the inner to the outer mitochondrial membrane and activated cyt c into a CL-specific peroxidase (Fernandez M G, Troiano L, Moretti L, et al. Early changes in intramitochondrial cardiolipin distribution during apoptosis. Cell Growth Differ 2002; 13:449-455 and Kagan V E, Tyurin V A, Jiang J, et al Cytochrome c acts as a cardiolipin oxygenase required for release of proapoptotic factors. Nat Chem Biol 2005; 1:223-232). The activated cyt c further catalyzed the oxidation of CL by using mitochondrially generated ROS (Kagan V E, Tyurin V A, Jiang J, et al. Cytochrome c acts as a cardiolipin oxygenase required for release of proapoptotic factors. Nat Chem Biol 2005; 1:223-232). Most importantly, oxidized CL is an important contributor to the release of cyt c from mitochondria (Kagan V E, Tyurin V A, Jiang J, et al. Cytochrome c acts as a cardiolipin oxygenase required for release of proapoptotic factors. Nat Chem Biol 2005; 1:223-232 and Petrosillo G, Casanova G, Matera M, et al Interaction of peroxidized cardiolipin with rat-heart mitochondrial membranes: Induction of permeability transition and cytochrome c release. FEBS Lett 2006; 580:6311-6316), which might be attributed to changes in microenvironment for the interaction between this phospholipid and cyt c (Ott M, Robertson J D, Gogvadze V, et al. Cytochrome c release from mitochondria proceeds by a two-step process. Proc Natl Acad Sci USA 2002; 99:1259-1263 and Gamido C, Galluzzi L, Brunet M, et al. Mechanisms of cytochrome c release from mitochondria. Cell Death Differ 2006; 13:1423-1433) and/or participation of oxidized CL in the formation of mitochondrial permeability transition pores (MTP) in coordination with Bcl-2 family proteins (Bid, Bax/Bak), as well as adenine nucleotide translocator (ANT) and voltage-dependent anion channel (VDAC) (Petrosillo G, Casanova G, Matera M, et al Interaction of peroxidized cardiolipin with rat-heart mitochondrial membranes: Induction of permeability transition and cytochrome c release. FEBS Lett 2006; 580:6311-6316 and Gonzalvez F, Gottlieb E. Cardiolipin: Setting the beat of apoptosis. Apoptosis 2007; 12:877-885). In addition to their essential role in the apoptotic signaling pathway, ROS were also implicated in perpetuation of the bystander effect (Narayanan P K, Goodwin E H, Lehnert B E. Alpha particles initiate biological production of superoxide anions and hydrogen peroxide in human cells. Cancer Res 1997; 57:3963-3971 and Iyer R, Lehnert B E. Factors underlying the cell growth-related bystander responses to alpha particles. Cancer Res 2000; 60:1290-1298) and genomic instability after irradiation exposure (Spitz D R, Azzam EI, Li JJ, et al. Metabolic oxidation/reduction reactions and cellular responses to ionizing radiation: A unifying concept in stress response biology. Cancer Metastasis Rev 2004; 23:311-322; Limoli CL, Giedzinski E, Morgan W F, et al. Persistent oxidative stress in chromosomally unstable cells. Cancer Res 2003; 63:3107-3111; and Kim G J, Chandrasekaran K, Morgan W F. Mitochondrial dysfunction, persistently elevated levels of reactive oxygen species and radiation-induced genomic instability: A review. Mutagenesis 2006; 21:361-367). Hence, elimination of intracellular ROS, particularly its major source, mitochondrial ROS, by antioxidants may be an important opportunity for developing radioprotectors and radiomitigators. Protection by antioxidants against IR has been studied for more than 50 years (Weiss J F, Landauer M R. Radioprotection by antioxidants. Ann N Y Acad Sci 2000; 899:44-60).

One of the major mechanisms of ionizing irradiation induced cell death is apoptosis, most commonly realized through a mitochondria dependent intrinsic pathway. Oxidation of cardiolipin catalyzed by cytochrome c ("cyt c"), release of cytochrome c and other pro-apoptotic factors into the cytosol and subsequent caspase activation are the key events in the execution of the death program designating the commencement of irreversible stages of apoptosis.

In Belikova, N A, et al., (Cardiolipin-Specific Peroxidase Reactions of Cytochrome C in Mitochondria During Irradiation-Induced Apoptosis, *Int. J. Radiation Oncology Biol. Phys.*, Vol. 69, No. 1, pp. 176-186, 2007), a small interfering RNA (siRNA) approach was used to engineer HeLa cells with lowered contents of cyt c (14%, HeLa 1.2 cells). Cells were treated by γ-irradiation (in doses of 5-40 Gy). Lipid oxidation was characterized by electrospray ionization mass spectrometry analysis and fluorescence highperformance liquid chromatography-based Amplex Red assay. Release of a proapoptotic factor (cyt c, Smac/DIABLO) was detected by Western blotting. Apoptosis was revealed by caspase-3/7 activation and phosphatidylserine externalization. They showed that irradiation caused selective accumulation of hydroperoxides in cardiolipin (CL) but not in other phospholipids. HeLa 1.2 cells responded by a lower irradiation-induced accumulation of CL oxidation products than parental HeLa cells. Proportionally decreased release of a proapoptotic factor, Smac/DIABLO, was detected in cyt c-deficient cells after irradiation. Caspase-3/7 activation and phosphatidylserine externalization were proportional to the cyt c content in cells. They concluded that cytochrome c is an important catalyst of CL peroxidation, critical to the execution of the apoptotic program. This new role of cyt c in irradiation-induced apoptosis is essential for the development of new radioprotectors and radiosensitizers.

Significant drug discovery efforts have been directed towards prevention of these events, particularly of the mitochondrial injury that represents an important point of no return. Although the exact mechanisms are still not well understood, generation of reactive oxygen species (ROS) and oxidation of cardiolipin by the peroxidase function of cytochrome c/cardiolipin complexes are believed to play a critical role in promoting cytochrome c release from mitochondria. ROS—superoxide radicals dismutating to $H_2O_2$—feed the peroxidase cycle and facilitate accumulation of oxidized cardiolipin. Hence, elimination of intracellular ROS, particularly its major source, mitochondrial ROS, by electron and radical scavengers is a promising opportunity for developing radioprotectors and radiomitigators. Significant research has been conducted in the field of radiation protection to use antioxidants against ionizing irradiation (Weiss et al Radioprotection by Antioxidants. Ann N Y Acad Sci 2000; 899:44-60).

A new class of antioxidants, stable nitroxide radicals, has been suggested as potent radioprotectors due to multiplicity of their direct radical scavenging properties as well as catalytic enzyme-like mechanisms (Saito et al. Two reaction sites of a spin label, TEMPOL with hydroxyl radical. J Pharm Sci 2003; 92:275-280; Mitchell et al. Biologically active metal-independent superoxide dismutase mimics. Biochemistry 1990; 29:2802-2807). TEMPOL (4-hydroxy-2,2,6,6-tetramethylpiperidine-N-oxyl) is a nitroxide whose properties as a radioprotector in vitro and in vivo have been extensively studied (Mitchell et al Nitroxides as radiation protectors. Mil Med 2002; 167:49-50; Hahn et al. In vivo radioprotection and effects on blood pressure of the stable free radical nitroxides. Int J Radiat Oncol Biol Phys 1998; 42:839-842. Mitchell et al. Inhibition of oxygen-dependent radiation-induced damage by the nitroxide superoxide dismutase mimic, tempol. Arch Biochem Biophys 1991; 289:62-70; Hahn et al. Tempol, a stable free radical, is a novel murine radiation protector. Cancer Res 1992; 52:1750-1753). Currently, TEMPOL is in clinical trials as a topical radiation protector to prevent hair loss during cancer radiotherapy. While found promising and relatively effective, the required high millimolar concentrations of TEMPOL, mainly due to its poor partitioning into cells and mitochondria, set a limit for its broader applications (Gariboldi et al. Study of in vitro and in vivo effects of the piperidine nitroxide Tempol—a potential new therapeutic agent for gliomas. Eur J Cancer 2003; 39:829-837). In addition, it has been demonstrated that TEMPOL must be present during irradiation to exert its radioprotective effect (Mitchell et al. Radiation, radicals, and images. Ann N Y Acad Sci 2000; 899:28-43; Mitchell et al Inhibition of oxygen-dependent radiation-induced damage by the nitroxide superoxide dismutase mimic, tempol. Arch Biochem Biophys 1991; 289: 62-70), This suggests that the protective mechanisms of TEMPOL are limited to its interactions with short-lived radiolytic intermediates produced by irradiation.

Sufficient concentrations of antioxidants at the sites of free radical generation are critical to optimized protection strategies. A great deal of research has indicated that mitochondria are both the primary source and major target of ROS (Reviewed in Orrenius S. Reactive oxygen species in mitochondria-mediated cell death. Drug Metab Rev 2007; 39:443-455). In fact, mitochondria have been long considered as an important target for drug discovery (Szewczyk et al., Mitochondria as a pharmacological target. 221 Pharmacol. Rev. 54:101-127; 2002; Garber K. Targeting mitochondria emerges as therapeutic strategy. J. Natl. Cancer Inst. 97:1800-1801; 2005).

Chemistry-based approaches to targeting of compounds to mitochondria include the use of proteins and peptides, as well as the attachment of payloads to lipophilic cationic compounds, triphenyl phosphonium phosphate, sulfonylureas, anthracyclines, and other agents with proven or hypothetical affinities for mitochondria (Murphy M P. Targeting bioactive compounds to mitochondria. Trends Biotechnol. 15:326-330; 1997; Dhanasekaran et al, Mitochondria superoxide dismutase mimetic inhibits peroxideinduced oxidative damage and apoptosis: role of mitochondrial superoxide. Free Radic. Biol. Med. 157 39:567-583; 2005; Hoye et al., Targeting Mitochondria. Acc. Chem. Res. 41: 87-97, 2008). However, at the time of this writing, no evidence has been presented that GS-nitroxides

SUMMARY

There remains a very real need for a composition and associated methods for delivering cargo of various types to mitochondria, specifically antioxidants. Provided herein are compounds comprising a targeting group and a cargo that is a nitroxide-containing group and compositions comprising the compounds. As illustrated in the Examples, below, compounds and compositions described herein have use in the prophylaxis and treatment of exposure to ionizing radiation, in anti-ageing therapies and, generally, in treating conditions that benefit from antioxidant treatment. Examples of these compounds are provided below and in the claims. For example, the effective mitochondrial concentration of mitochondria targeted conjugated nitroxides (—N—O., —N—OH or N=O containing compounds and groups) against γ-irradiation could be increased up to 1,000 times (and their required tissues concentrations can be reduced 1,000 times from 10 mM to 10 μM) compared with parent non-conjugated nitroxides. Enrichment in mitochondria of mitochondria targeted nitroxides has been demonstrated by EPR spectroscopy as well as by MS analysis of their content in mitochondria obtained from cells incubated with mitochondria targeted nitroxides. Delivery of mitochondria targeted-nitroxides into mitochondria does not depend on the mitochondrial membrane potential. Therefore, mitochondria targeted nitroxides can accumulate not only in intact but also in de-energized or damaged mitochondria with low membrane potential. Moreover, mitochondria targeted nitroxide conjugates are delivered into mitochondria without affecting the mitochondrial membrane potential. Hence, they do not impair the major mitochondrial function, the energy production, in cells. In addition, the conjugated nitroxides provide a new important feature, post irradiation protection.

Like other nitroxides, conjugated mitochondria targeted nitroxides might potentially lower blood pressure and sympathetic nerve activity. However, the dramatically reduced dose of mitochondria targeted nitroxides (about 1,000-fold), compared to non-conjugated parental nitroxides, may be significantly below of those inducing side effects.

BRIEF DESCRIPTION OF THE DRAWINGS

FIG. 5A shows an FD4 read-out of TEMPOL which is used as a "positive control" for the gut mucosal protection assay. FIG. 5B shows an FD4 read-out of TEMPO conjugate XJB-5-208 reflecting gut mucosal protection. FIG. 5C shows an FD4 read-out of XJB-5-125 which has the TEMPO payload, but fails to provide protection against gut barrier dysfunction induced by hemorrhage. FIG. 5D shows an FD4 read-out of XJB-5-127 which lacks the TEMPO payload and fails to provide protection against gut barrier dysfunction induced by hemorrhage. FIG. 5E shows an FD4 read-out of TEMPO conjugate XJB-5-131 reflecting gut mucosal protection. FIG. 5F shows an FD4 read-out of XJB-5-133 which lacks the TEMPO payload even though it possesses the same hemigramicidin mitochondria targeting moiety as the most active compound, XJB-5-131. FIG. 5G shows an FD4 read-out of XJB-5-197 which has the TEMPO payload, but fails to provide protection against gut barrier dysfunction induced by hemorrhage. FIG. 5H shows an FD4 read-out of XJB-S-194 which lacks the TEMPO payload and fails to provide protection against gut barrier dysfunction induced by hemorrhage.

FIG. 6A is a graphical representation of superoxide production based upon mean fluorescence intensity from 10,000 ileal cells. FIG. 6B is a graphical representation of phosphatidylserine (PS) externalization as indicated by the percentage of annexin V-positive cells. FIG. 6C is a graphical representation of caspase-3 activity as indicated by amount of its specific substrate present, Z-DVED-AMC, in nmol/mg protein. FIG. 6D is a graphical representation of DNA fragmentation as indicated by propidium iodide fluorescence. FIG. 6E is a graphical representation of PS externalization at different concentrations of the compound 5a (as shown in FIG. 3). FIG. 6F is a graphical representation of adenosine triphosphate (ATP) levels in mitochondria in the presence or absence of 5a or 2-deoxyglucose.

FIG. 7 illustrates the effects of intraluminal XJB-5-131 on hemorrhage-induced peroxidation of phospholipids in intestinal mucosa.

FIG. 8 is a graphical representation of caspase 3 and 7 activity that illustrates the effects of intraluminal XJB-5-131.

FIG. 9 is a graphical representation of permeability of XJB-5-131 with respect to Caco-2BBe human enterocyte-like monolayers subjected to oxidative stress. The permeability of the monolayers is expressed as a clearance (pL·h⁻¹·cm2).

DETAILED DESCRIPTION

Figure 1:
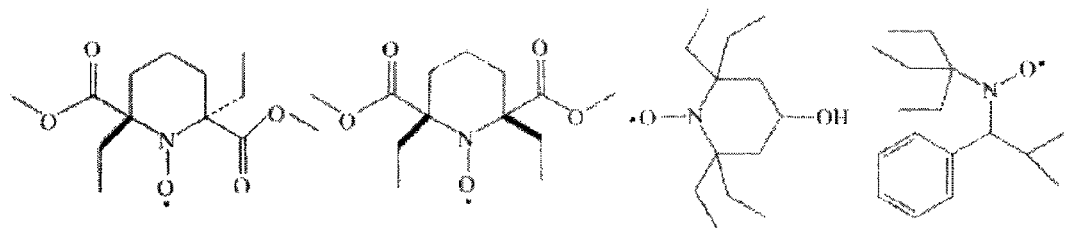
FIG. 1 provides non-limiting examples of certain nitroxides. The logP values were estimated using the online calculator of molecular properties and drug likeness on the Molinspirations Web site (www.molinspiration.com/cgi-bin/properties). TIPNO=tert-butyl isopropyl phenyl nitroxide.
Figure 1:
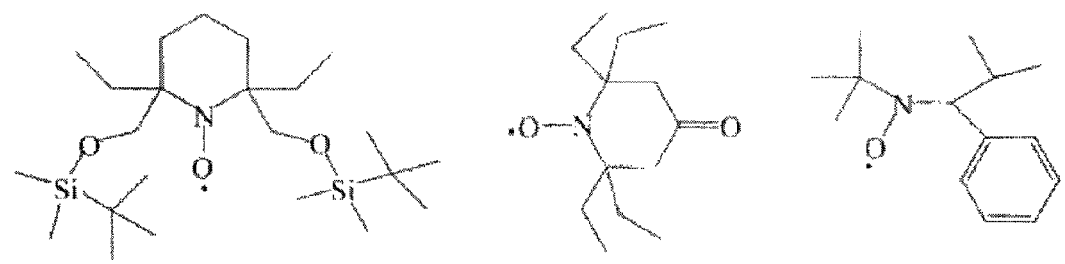
Figure 1:
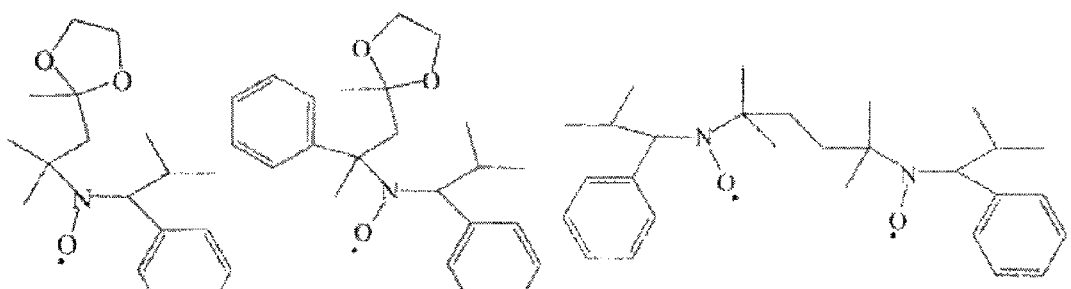
Figure 1:
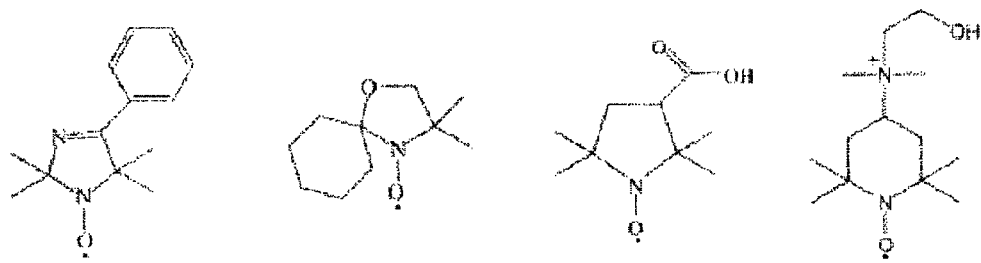

As used herein, the term "subject" refers to members of the animal kingdom including but not limited to human beings. The term "reactive oxygen species" ("ROS") includes, but is not limited to, superoxide anion, hydroxyl, and hydroperoxide radicals.

An antioxidant compound is defined herein as a compound that decreases the rate of oxidation of other compounds or prevents a substance from reacting with oxygen or oxygen containing compounds. A compound may be determined to be an antioxidant compound by assessing its ability to decrease molecular oxidation and/or cellular sequellae of oxidative stress, for example, and without limitation, the ability to decrease lipid peroxidation and/or decrease oxidative damage to protein or nucleic acid. In one embodiment, an antioxidant has a level of antioxidant activity between 0.01 and 1000 times the antioxidant activity of ascorbic acid in at least one assay that measures antioxidant activity.

Provided herein are compounds and compositions comprising a targeting group and a cargo, such as a nitroxide-containing group. The cargo may be any useful compound, such as an antioxidant, as are well known in the medical and chemical arts. The cargo may comprise a factor having antimicrobial activity. For example, the targeting groups may be cross-linked to antibacterial enzymes, such as lysozyme, or antibiotics, such as penicillin. Other methods for attaching the targeting groups to a cargo are well known in the art. In one embodiment, the cargo is an antioxidant, such as a nitroxide-containing group. In another embodiment, the cargo transported by mitochondria-selective targeting agents may include an inhibitor of NOS activity. The cargo may have a property selected from the group consisting of antioxidant, radioprotective, protective, anti-apoptotic, therapeutic, ameliorative, NOS antagonist and combinations thereof. In another embodiment, the cargo may have the ability to inhibit nitric oxide synthase enzyme activity. It will be appreciated that a wide variety of cargos may be employed in the composition described herein. Non-limiting examples of cargos include: a 2-amino-6-methyl-thiazine, a ubiquinone analog, a ubiquinone analog fragment moiety, a ubiquinone analog fragment moiety lacking a hydrophilic tail, a superoxide dismutase mimetic, a superoxide dismutase biomimetic and a salen-manganese compound.

While the generation of ROS in small amounts is a typical byproduct of the cellular respiration pathway, certain conditions, including a disease or other medical condition, may occur in the patient when the amount of ROS is excessive to the point where natural enzyme mechanisms cannot scavenge the amount of ROS being produced. Therefore, compounds, compositions and methods that scavenge reactive oxygen species that are present within the mitochondrial membrane of the cell are useful and are provided herein. These compounds, compositions and methods have the utility of being able to scavenge an excess amount of ROS being produced that naturally occurring enzymes SOD and catalase, among others, cannot cope with.

In one non-limiting embodiment, the compound has the structure:

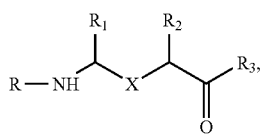

(Formula 1)

wherein X is one of

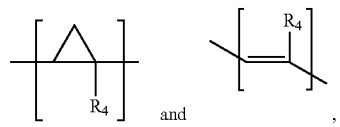

and $R_1$, $R_2$ and $R_4$ are, independently, hydrogen, $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl. $R_3$ is —NH—$R_5$, —O—$R_5$ or —CH$_2$—$R_5$, where $R_5$ is an —N—O., —N—OH or N═O containing group. In one embodiment, $R_3$ is

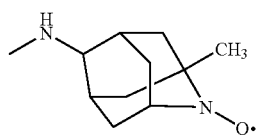

(1-Me-AZADO or 1-methyl 2-azaadamantane N-oxyl). In another embodiment $R_3$ is

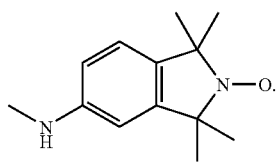

(TMIO; 1,1,3,3-tetramethylisoindolin-2-yloxyl).
R is —C(O)—$R_6$, —C(O)O—$R_6$, or —P(O)—($R_6$)$_2$, wherein $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted, including Ac (Acetyl, R═—C(O)—CH$_3$), Boc (R═—C(O)O-tert-butyl), Cbz (R═—C(O)O-benzyl (Bn)) groups. R also may be a diphenylphosphate group, that is,

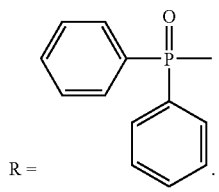

Excluded from this is the enantiomer XJB-5-208. In certain embodiments, $R_1$ is t-butyl and $R_2$ and $R_4$ are H; for instance:

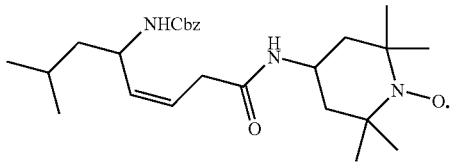

jmf129-51

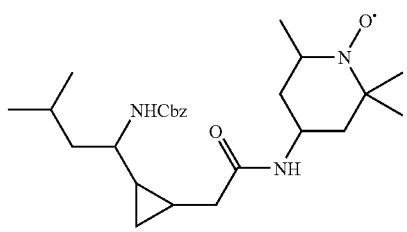

jmf129-37

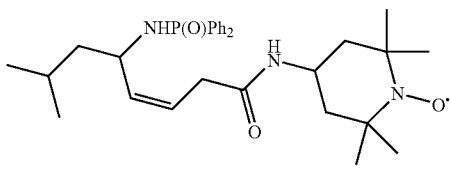

jmf129-52

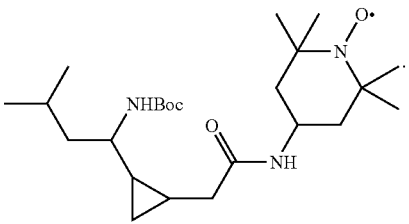

jmf129-83

As used herein, unless indicated otherwise, for instance in a structure, all compounds and/or structures described herein comprise all possible stereoisomers, individually or mixtures thereof.

As indicated above, $R_5$ is an —N—O., —N—OH or —N═O containing group (not —N—O., —N—OH or —N═O alone, but groups containing those moieties, such as TEMPO, etc, as described herein). As is known to one ordinarily skilled in the art, nitroxide and nitroxide derivatives, including TEMPOL and associated TEMPO derivatives are stable radicals that can withstand biological environments. Therefore, the presence of the 4-amino-TEMPO, TEMPOL or another nitroxide "payload" within the mitochondria membrane can serve as an effective and efficient electron scavenger of the ROS being produced within the membrane. Non-limiting examples of this include TEMPO (2,2,6,6-Tetramethyl-4-piperidine 1-oxyl) and TEMPOL (4-Hydroxy-TEMPO), in which, when incorporated into the compound described herein, for example, when $R_3$ is —NH—$R_5$, —O—$R_5$:

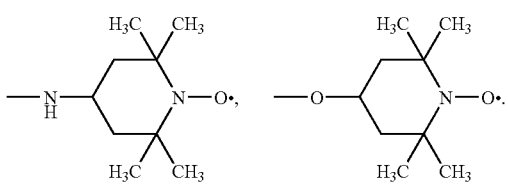

Additional non-limiting examples of —N—O•, —N—OH or N=O containing group are provided in Table 1 and in FIG. 1 (from Jiang, J., et al. "Structural Requirements for Optimized Delivery, Inhibition of Oxidative Stress, and Antiapoptotic Activity of Targeted Nitroxides", J Pharmacol Exp Therap. 2007, 320(3):1050-60). A person of ordinary skill in the art would be able to conjugate (covalently attach) any of these compounds to the rest of the compound using common linkers and/or conjugation chemistries, such as the chemistries described herein. Table 1 provides a non-limiting excerpt from a list of over 300 identified commercially-available —N—O•, —N—OH or N=O containing compounds that may be useful in preparation of the compounds or compositions described herein.

TABLE 1

Commercially-available —N—O•, —N—OH or N=O containing groups

| Structure | Name | CAS No. |
|---|---|---|
| 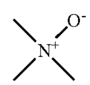 | Trimethylamine N-Oxide | 1184-78-7 |
| 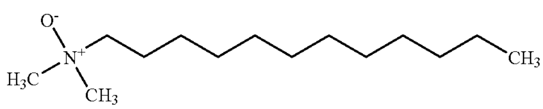 | N,N-Dimethyldodecylamine N-Oxide | 1643-20-570592-80-2 |
| 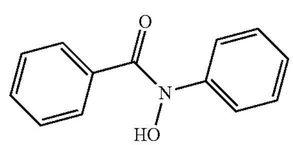 | N-Benzoyl-N-Phenylhydroxylamine | 304-88-1 |
| 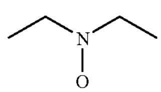 | N,N-Diethylhydroxylamine | 3710-84-7 |
| 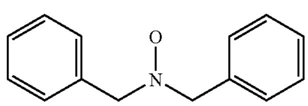 | N,N-Dibenzylhydroxylamine | 14165-27-6621-07-8 |
| 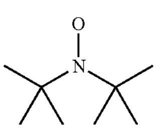 | Di-Tert-Butyl Nitroxide | 2406-25-9 |
| 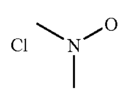 | N,N-Dimethylhydroxylamine Hydrochloride | 16645-06-0 |
| 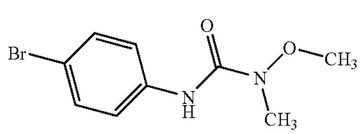 | Metobromuron | 3060-89-7 |
| 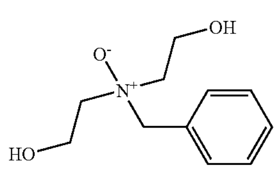 | Benzyl-Di-Beta-Hydroxy Ethylamine-N-Oxide | |
| 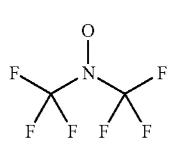 | Bis(Trifluoromethyl)Nitroxide | 2154-71-4 |

TABLE 1-continued

Commercially-available —N—O•, —N—OH or N=O containing groups

| Structure | Name | CAS No. |
|---|---|---|
| 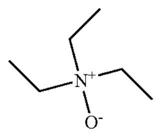 | Triethylamine N-Oxide | 2687-45-8 |
| | | |
| 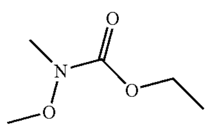 | N-Methoxy-N-Methylcarbamate | 6919-62-6 |
| 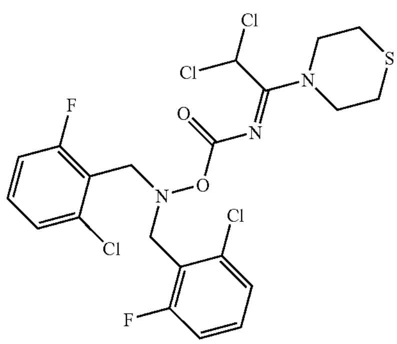 | N,N-Bis(2-Chloro-6-Fluorobenzyl)-N-[(([2,2-Dichloro-1-(1,4-Thiazinan-4-yl+)ethylidene]amino)carbonyl)oxy]amine | |
| 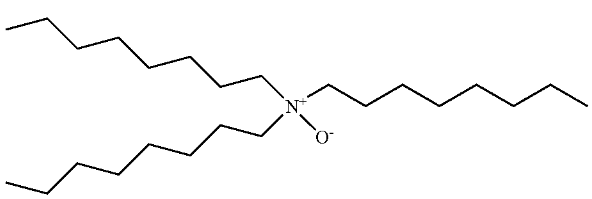 | Tri-N-Octylamine N-Oxide | 13103-04-3 |
| 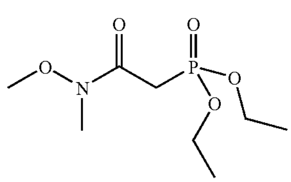 | Diethyl(N-Methoxy-N-Methylcarbamoylmethyl) Phoshonate | 124931-12-0 |
| 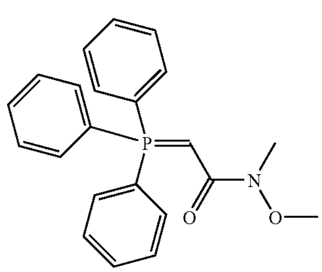 | N-Methoxy-N-Methyl-2-(Triphenylphosphoranylidene)Acetamide | 129986-67-0 |

TABLE 1-continued

Commercially-available —N—O•, —N—OH or N=O containing groups

| Structure | Name | CAS No. |
|---|---|---|
| 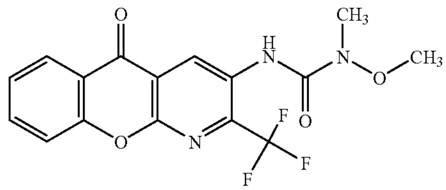 | N-Methoxy-N-Methyl-N'-[5-Oxo-2-(Trifluoromethyl)-5h-Chromeno[2,3-B]Pyridi+N-3-Y1]Urea |  |
| 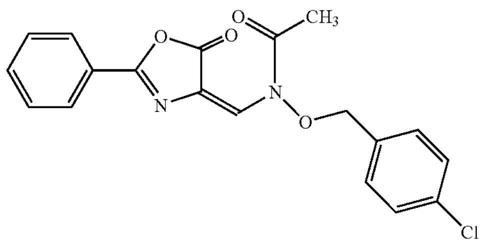 | N-[(4-Chlorobenzyl)Oxy]-N-([5-Oxo-2-Phenyl-1,3-Oxazol-4(5h)-Yliden]Methyl+)Acetamide |  |
| 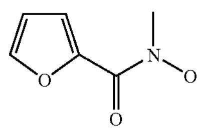 | N-Methylfurohydroxamic Acid | 109531-96-6 |
| 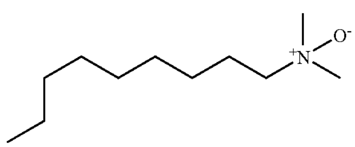 | N,N-Dimethylnonylamine N-Oxide | 2536-13-2 |
| 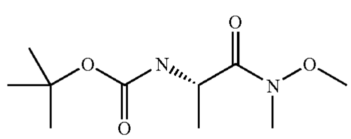 | N-(Tert-Butoxycarbonyl)-L-Alanine N'-Methoxy-N'-Methylamide | 87694-49-3 |
| 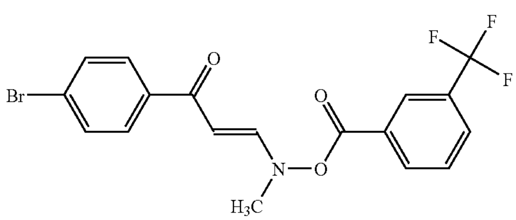 | 1-(4-Bromophenyl)-3-(Methyl([3-(Trifluoromethyl)Benzoyl]Oxy)Amino)-2-Prop+En-1-One |  |
| 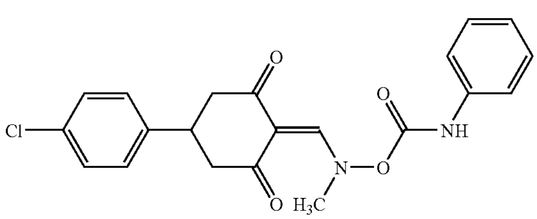 | 2-([[(Anilinocarbonyl)Oxy](Methyl)Amino]Methylene)-5-(4-Chlorophenyl)-1,3+-Cyclohexanedione |  |
| 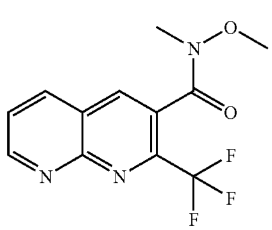 | N-Methoxy-N-Methyl-2-(Trifluoromethyl)-1,8-Naphthyridine-3-Carboxamide |  |

TABLE 1-continued

Commercially-available —N—O•, —N—OH or N=O containing groups

| Structure | Name | CAS No. |
|---|---|---|
| 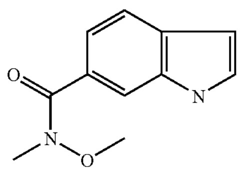 | N-Methoxy-N-Methyl-Indole-6-Carboxamide | |
| 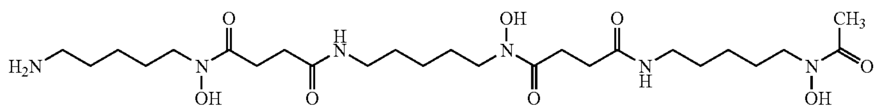 | Desferrioxamin | |
| 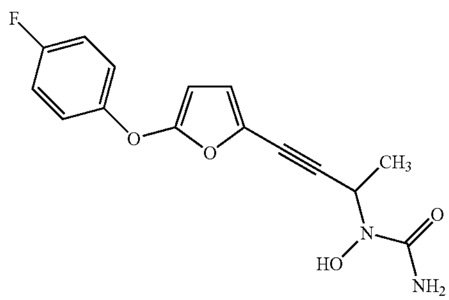 | AKOS 91254 | 127408-31-5 |
| 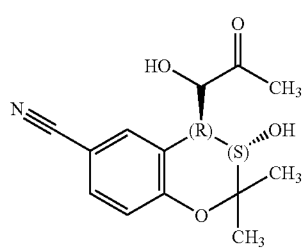 | N-[(3s,4r)-6-Cyano-3,4-Dihydro-3-Hydroxy-2,2-Dimethyl-2h-1-Benzopyran-4-Y+L]-N-Hydroxyacetamide | 127408-31-5 |
| 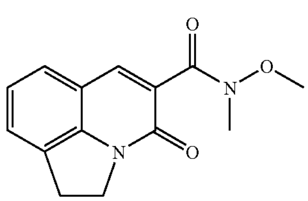 | N-Methoxy-N-Methyl-1,2-Dihydro-4-Oxo-Pyrrolo[3,2,1-Ij]Quinoline-5-Carboxa+Mide | |
| 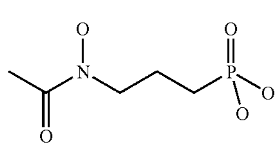 | Fr-900098 | |
| 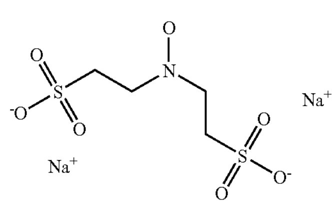 | 2,2'-(Hydroxyimino)Bis-Ethanesulfonic Acid Disodium Salt | 133986-51-3 |

TABLE 1-continued

Commercially-available —N—O•, —N—OH or N=O containing groups

| Structure | Name | CAS No. |
|---|---|---|
| 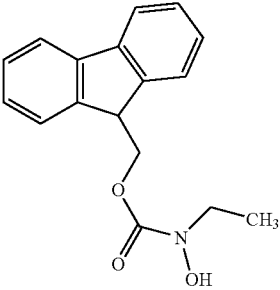 | Fmoc-N-Ethyl-Hydroxylamine | |
| 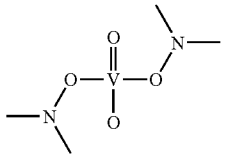 | Bis(N,N-Dimethylhydroxamido)Hydroxooxovanadate | |
| 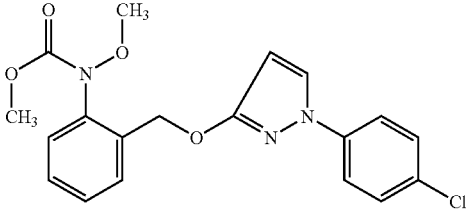 | Pyraclostrobin | 175013-18-0 |
| 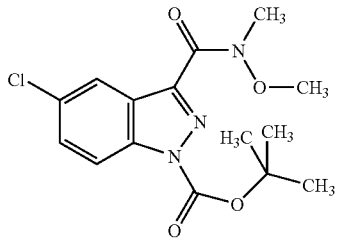 | 1-Boc-5-Chloro-3-(Methoxy-Methyl-Carbamoyl)Indazole | |
| 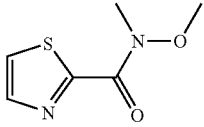 | N-Methoxy-N-Methyl-Thiazole-2-Carboxamide | |
| 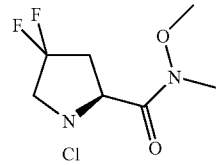 | 4,4-Difluoro-N-Methyl-N-Methoxy-L-Prolinamide Hcl | |
| 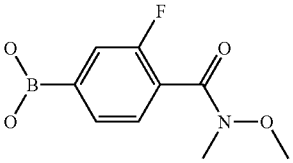 | 3-Fluoro-4-(Methoxy(Methyl)Carbamoyl)Phenylboronic Acid | 913835-59-3 |

TABLE 1-continued

Commercially-available —N—O•, —N—OH or N=O containing groups

| Structure | Name | CAS No. |
|---|---|---|
| 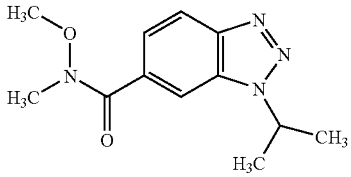 | 1-Isopropyl-N-Methoxy-N-Methyl-1h-Benzo[D][1,2,3]Triazole-6-Carboxamide | 467235-06-9 |
| 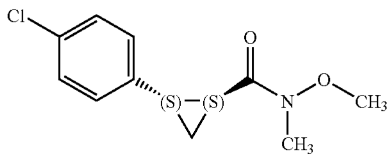 | (Trans)-2-(4-Chlorophenyl)-N-Methoxy-N-Methylcyclopropanecarboxamide | |
| 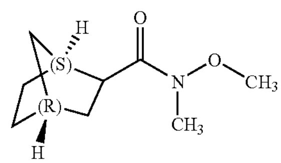 | Bicyclo[2.2.1]Heptane-2-Carboxylic Acid Methoxy-Methyl-Amide | |
| 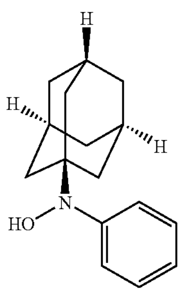 | Akos Bc-0582 | |
| 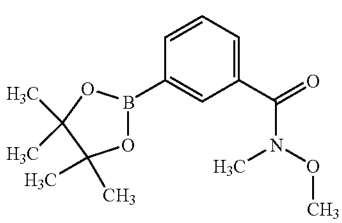 | 3-(N,O-Dimethylhydroxylaminocarbonyl)Phenylboronic Acid, Pinacol Ester | |
| 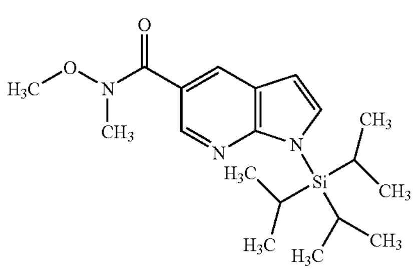 | 1-Triisopropylsilanyl-1h-Pyrrolo[2,3-B]Pyridine-5-Carboxylic Acid Methoxy+-Methyl-Amide | |

According to one embodiment, the compound has the structure

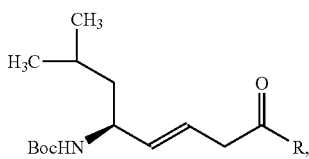

or the structure

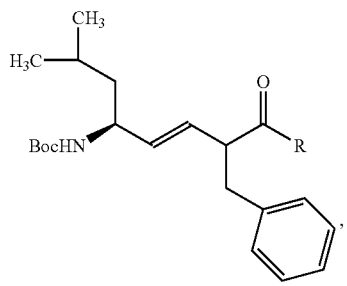

wherein R is —NH—R$_1$, —O—R$_1$ or —CH$_2$—R$_1$, and R$_1$ is an —N—O., —N—OH or N=O containing group. In one embodiment, R is —NH—R$_1$, and in another R is —NH-TEMPO.

According to another embodiment, the compound has the structure:

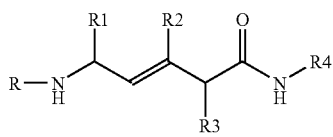

(Formula 2)

in which R1, R2 and R3 are, independently, hydrogen, C$_1$-C$_6$ straight or branched-chain alkyl, optionally including a phenyl (C$_6$H$_5$) group, that optionally is methyl-, hydroxyl- or fluoro-substituted, including 2-methyl propyl, benzyl, methyl-, hydroxyl- or fluoro-substituted benzyl, such as 4-hydroxybenzyl. R4 is an —N—O., —N—OH or N=O containing group. In one embodiment, R4 is

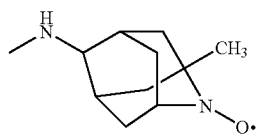

(1-Me-AZADO or 1-methyl 2-azaadamantane N-oxyl). In another embodiment R4 is

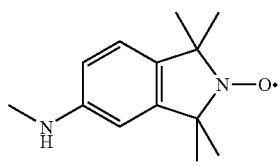

(TMIO; 1,1,3,3-tetramethylisoindolin-2-yloxyl). R is —C(O)—R5, —C(O)O—R5, or —P(O)—(R5)$_2$, wherein R5 is C$_1$-C$_6$ straight or branched-chain alkyl, optionally comprising one or more phenyl (—C$_6$H$_5$) groups, and that optionally are methyl-, ethyl-, hydroxyl- or fluoro-substituted, including Ac, Boc, and Cbz groups. R also may be a diphenylphosphate group, that is, R=

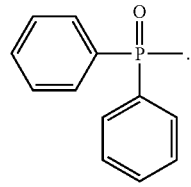

In certain specific embodiments, in which R4 is TEMPO, the compound has one of the structures A, A1, A2, or A3 (Ac=Acetyl=CH$_3$C(O)—):

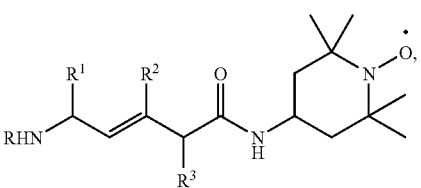

A

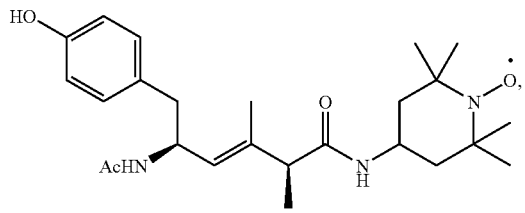

A1

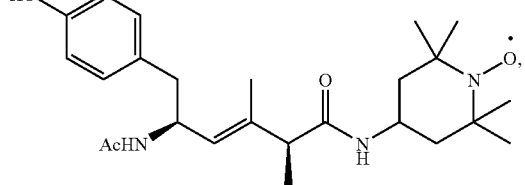

A2

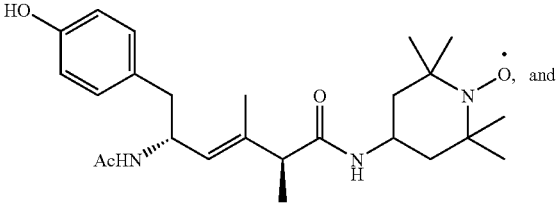

A3

According to another embodiment, the compound has the structure

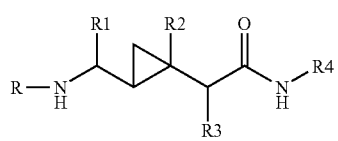

(Formula 3)

In which R1, R2 and R3 are, independently, hydrogen, C$_1$-C$_6$ straight or branched-chain alkyl, optionally including a phenyl (C₆H₅) group, that optionally is methyl-, hydroxyl- or fluoro-substituted, including 2-methyl propyl, benzyl, methyl-, hydroxyl- or fluoro-substituted benzyl, such as 4-hydroxybenzyl. R4 is an —N—O., —N—OH or N=O containing group. In one embodiment, R4 is

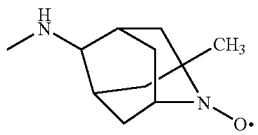

(1-Me-AZADO or 1-methyl 2-azaadamantane N-oxyl). In another embodiment R4 is

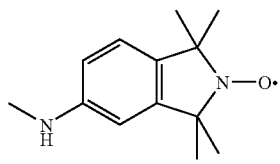

(TMIO; 1,1,3,3-tetramethylisoindolin-2-yloxyl). R is —C(O)—R5, —C(O)O—R5, or —P(O)—(R5)₂, wherein R5 is C₁-C₆ straight or branched-chain alkyl, optionally comprising one or more phenyl (—C₆H₅) groups, and that optionally are methyl-, ethyl-, hydroxyl- or fluoro-substituted, including Ac, Boc, and Cbz groups. R also may be a diphenylphosphate group, that is,

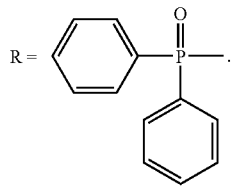

In certain specific embodiments, in which R4 is TEMPO, the compound has one of the structures D, D1, D2, or D3 (Ac=Acetyl=CH₃C(O)—):

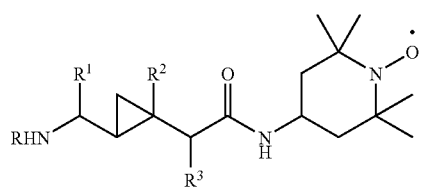

D

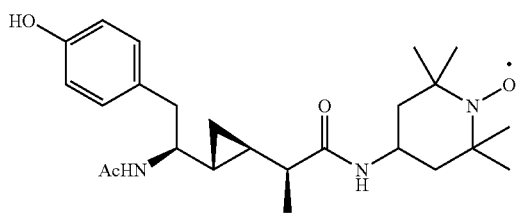

D1

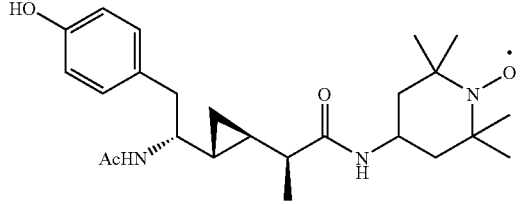

D2

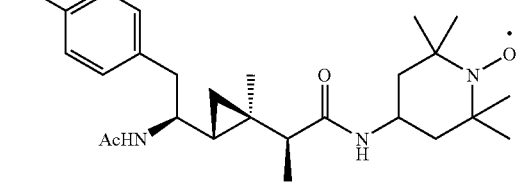

D3

In another non-limiting embodiment, the compound has the structure:

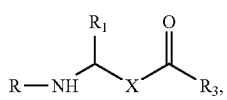

(Formula 4)

wherein X is one of

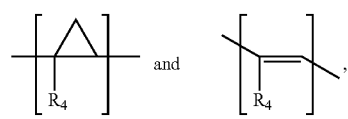

and

R₁ and R₄ are, independently, hydrogen, C₁-C₆ straight or branched-chain alkyl, optionally including a phenyl (C₆H₅) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl. R₃ is —NH—R₅, —O—R₅ or —CH₂—R₅, where R₅ is an —N—O., —N—OH or N=O containing group. In one embodiment, R₃ is

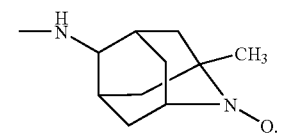

(1-Me-AZADO or 1-methyl azaadamantane N-oxyl). In another embodiment $R_3$ is

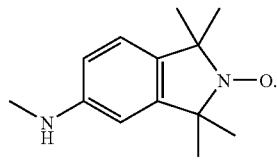

(TMIO; 1,1,3,3-tetramethylisoindolin-2-yloxyl).

R is —C(O)—$R_6$, —C(O)O—$R_6$, or —P(O)—$(R_6)_2$, wherein $R_6$ is $C_1$-$C_6$ straight or branched-chain alkyl optionally comprising one or more phenyl (—$C_6H_5$) groups, and that optionally are methyl-, ethyl-, hydroxyl- or fluoro-substituted, including Ac (Acetyl, R=—C(O)—$CH_3$), Boc (R=—C(O)O-tert-butyl), Cbz (R=—C(O)O-benzyl (Bn)) groups. R also may be a diphenylphosphate group, that is,

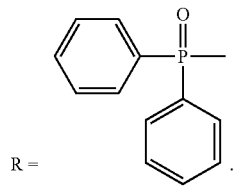

In one non-limiting embodiment, the compound has one of the structures

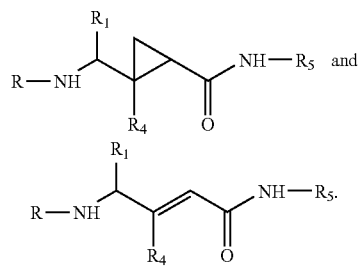

In yet another non-limiting embodiment, the compound has the structure

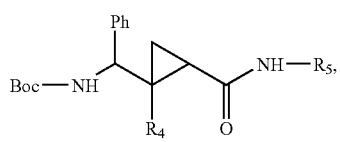

in which $R_4$ is hydrogen or methyl.

The compounds described above, such as the compound of Formula 1, can be synthesized by any useful method. The compound JP4-039 was synthesized by the method of Example 8. In one embodiment, a method of making a compound of Formula 1 is provided. The compounds are synthesized by the following steps:

reacting an aldehyde of structure R1—C(O)—, wherein, for example and without limitation, R1 is $C_1$-$C_6$ straight or branched-chain alkyl, optionally including a phenyl ($C_6H_5$) group, that optionally is methyl-, hydroxyl- or fluoro-substituted, including: methyl, ethyl, propyl, 2-propyl, butyl, t-butyl, pentyl, hexyl, benzyl, hydroxybenzyl (e.g., 4-hydroxybenzyl), phenyl and hydroxyphenyl, with (R)-2-methylpropane-2-sulfinamide to form an imine, for example

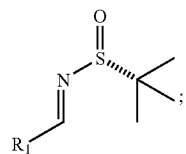

reacting a terminal alkyne-1-ol (HCC—$R_2$—$CH_2$—OH), wherein, for example and without limitation, $R_2$ is not present or is branched or straight-chained alkylene, including methyl, ethyl, propyl, etc., with a tert-butyl diphenylsilane salt to produce an alkyne, for example

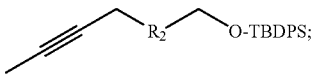

reacting (by hydrozirconation) the alkyne with the imine in the presence of an organozirconium catalyst to produce an alkene, for example

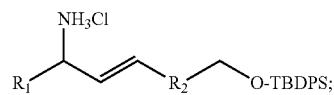

D1. acylating the alkene to produce a carbamate, for example

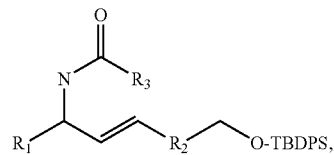

wherein, for example and without limitation, $R_3$ is $C_1$-$C_6$ straight or branched-chain alkyl, optionally including a phenyl ($C_6H_5$) group, that optionally is methyl-, hydroxyl- or fluoro-substituted, including including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

D2. optionally, cyclopropanating the alkene and then acylating the alkene to produce a carbamate, for example

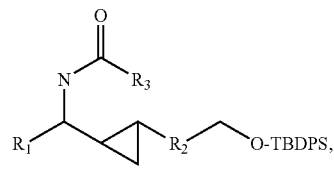

wherein, for example and without limitation, $R_3$ is $C_1$-$C_6$ straight or branched-chain alkyl, optionally including a phenyl ($C_6H_5$) group, that optionally is methyl-, hydroxyl- or fluoro-substituted, including including: methyl, ethyl, propyl, 2-propyl, butyl, t-butyl, pentyl, hexyl, benzyl, hydroxybenzyl (e.g., 4-hydroxybenzyl), phenyl and hydroxyphenyl;

removing the t-butyldiphenylsilyl group from the carbamate to produce an alcohol, for example

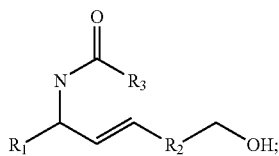

oxidizing the alcohol to produce a carboxylic acid, for example

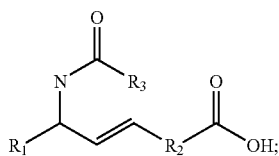

and reacting the carboxylic acid with a nitroxide-containing compound comprising one of a hydroxyl or amine in a condensation reaction to produce the antioxidant compound, for example

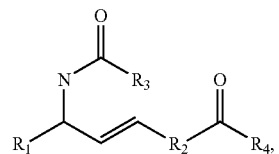

wherein $R_4$ is —NH—$R_4$ or —O—$R_4$, and $R_4$ is an —N—O., —N—OH or N═O containing group, such as described above.

Figure 2:
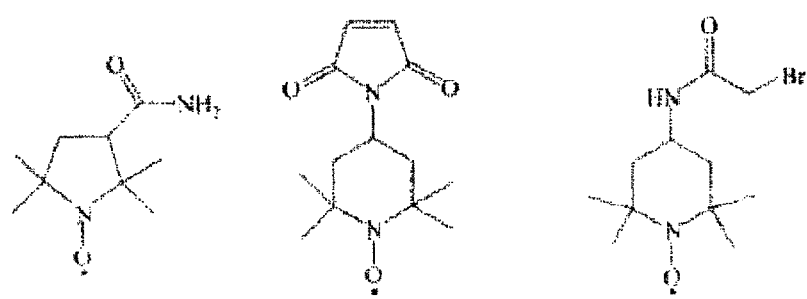
FIG. 2 provides examples of structures of certain mitochondria-targeting antioxidant compounds referenced herein, and the structure of TEMPOL.
Figures 1, 2:
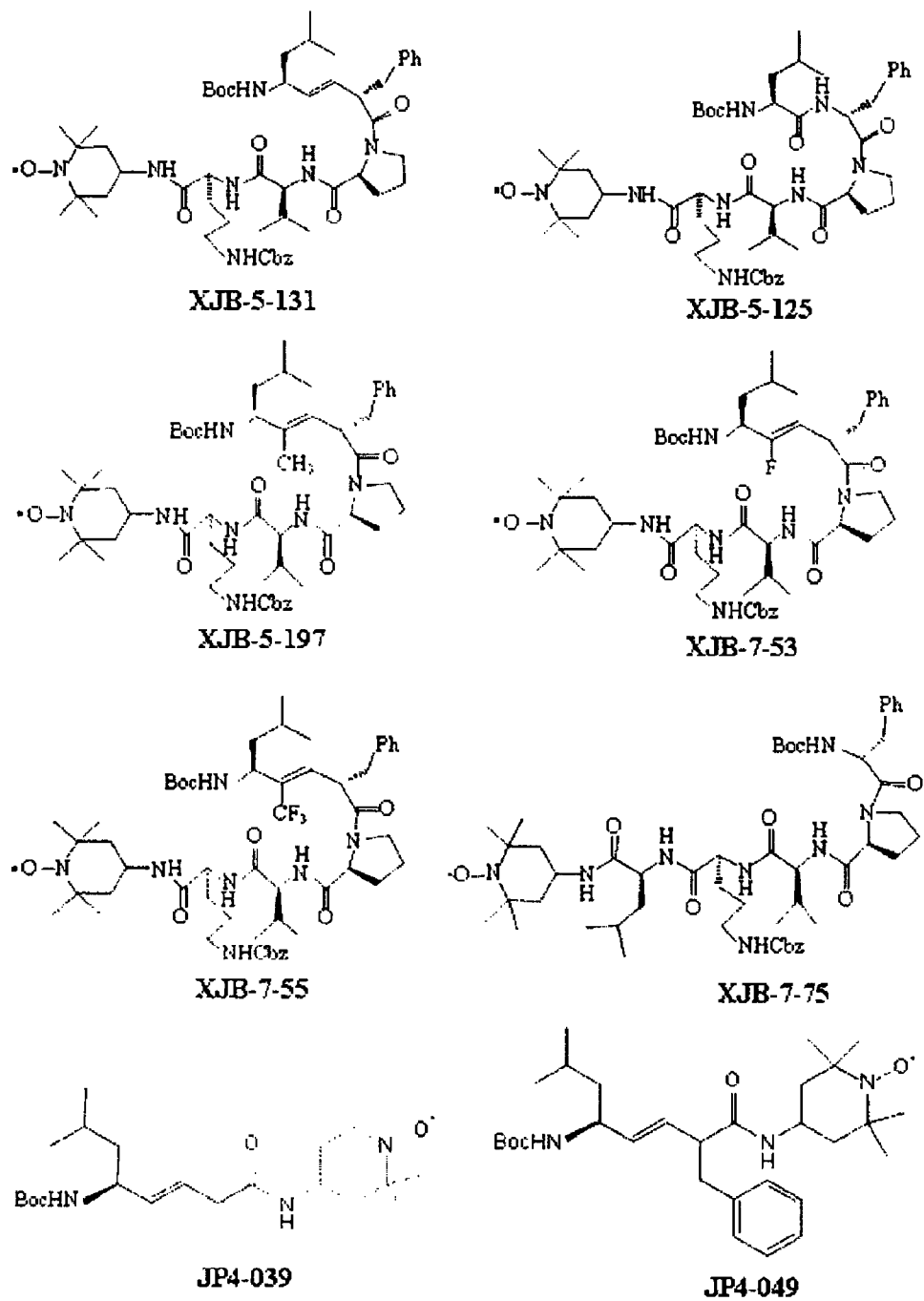
Figure 2:
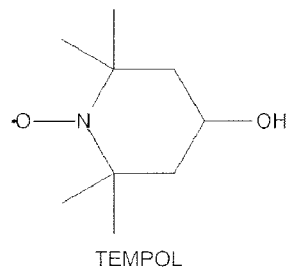
Figure 2:
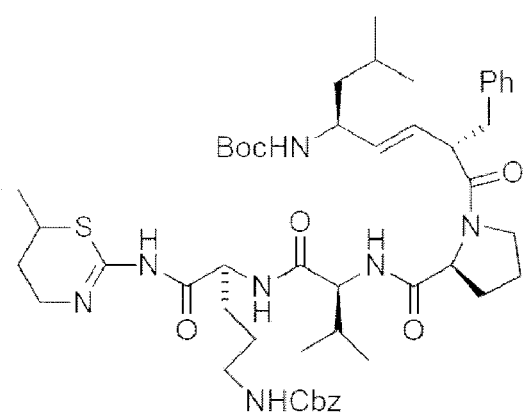
Figure 2:
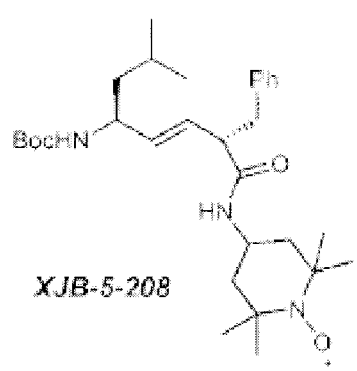
Figure 2:
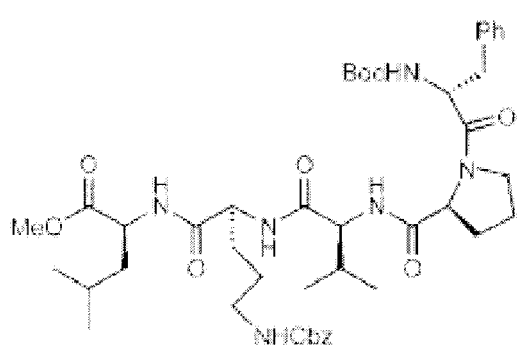
Figure 2:
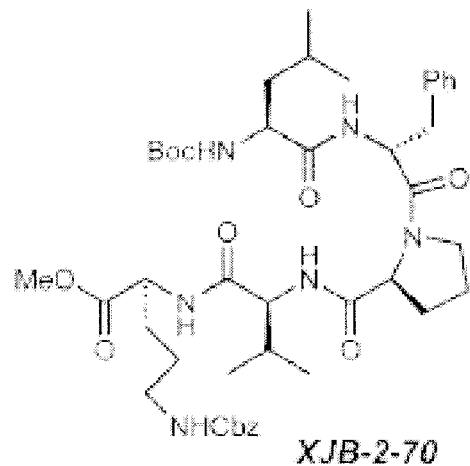
Figure 26A:
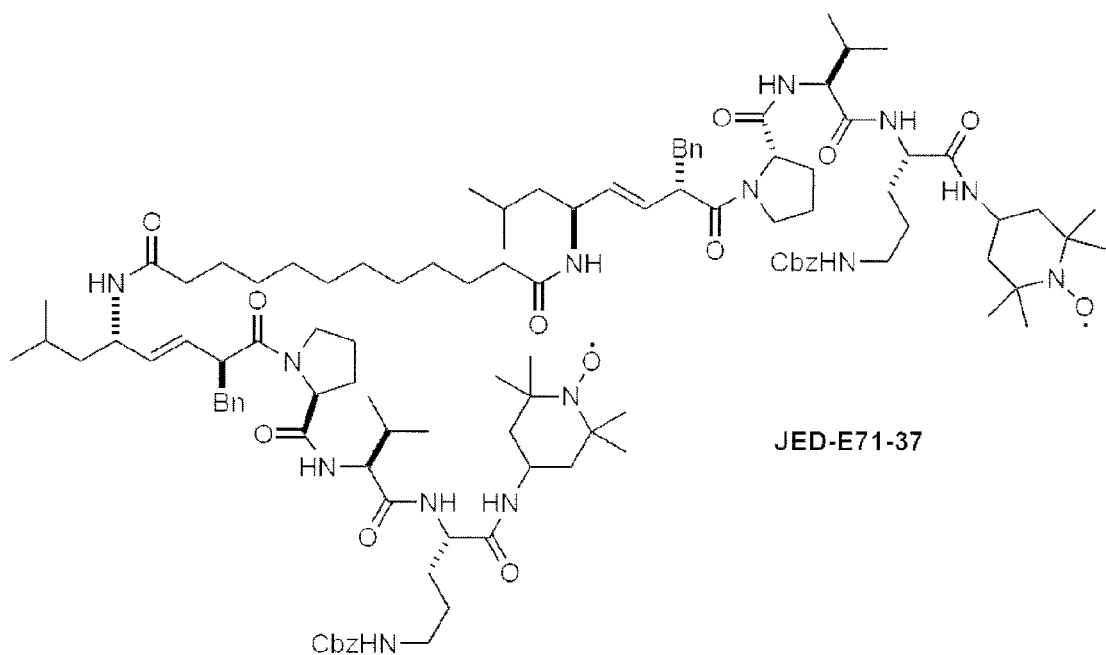
Figure 26B:
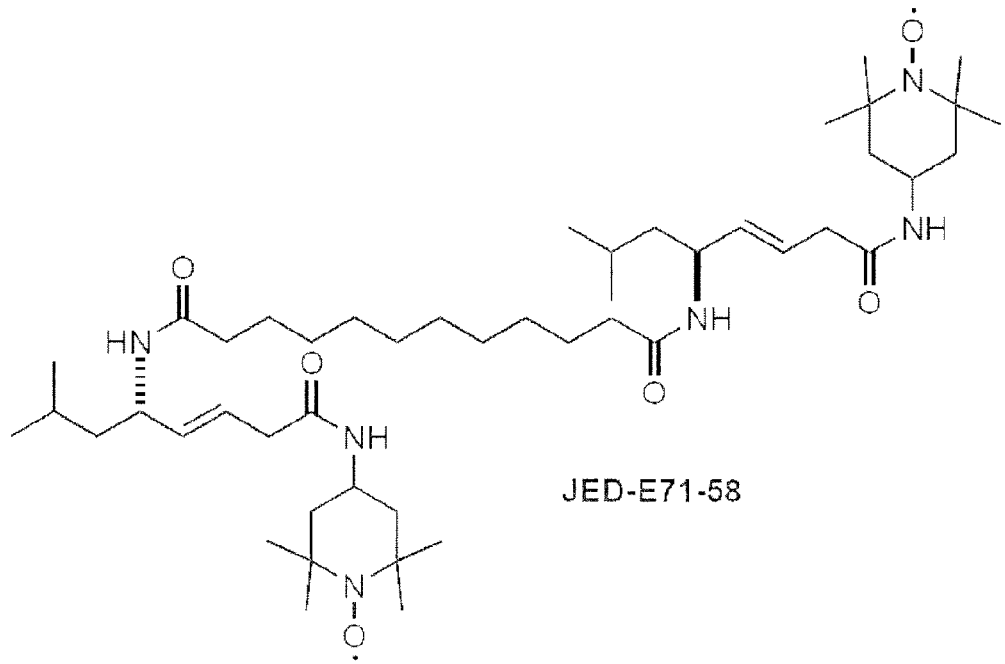
Figures 27, 28:
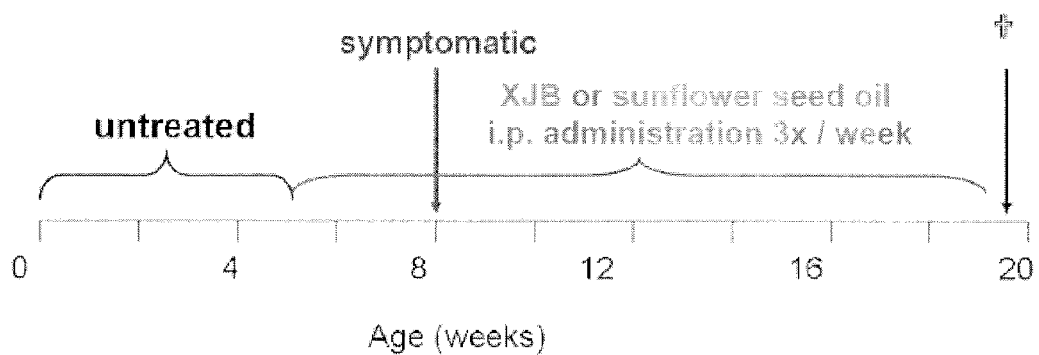
FIG. 27 shows a treatment paradigm for study to determine the impact of XJB-5-131 on the age at onset of signs of aging in progeroid $Ercc1^{-/\Delta}$ mice. XJB-5-131 was 2 mg/kg prepared from a 10 µg/µL stock in DMSO mixed with 50 µL of sunflower seed oil and injected intraperitoneally. As control littermate $Ercc1^{-/\Delta}$ mice were treated with an equal volume of sunflower seed oil only, in double-blind twin study.
FIG. 28 is a summary table showing effects of treatment with XJB-5-131 ("XJB" in this figure), relative to control (sunflower seed oil) on the age at onset (in weeks) of various indicia of aging in $Ercc1^{-/\Delta}$ mice, using the protocol of FIG. 27. The duration of treatment of mice in this figure was three times per week, beginning at 5 wks of age and continuing throughout their lifespan. Cells highlighted in the XJB column indicate a significant delay in onset of the age-related degenerative change in mice treated with XJB relative to isogenic controls treated with vehicle only.
Figure 29:
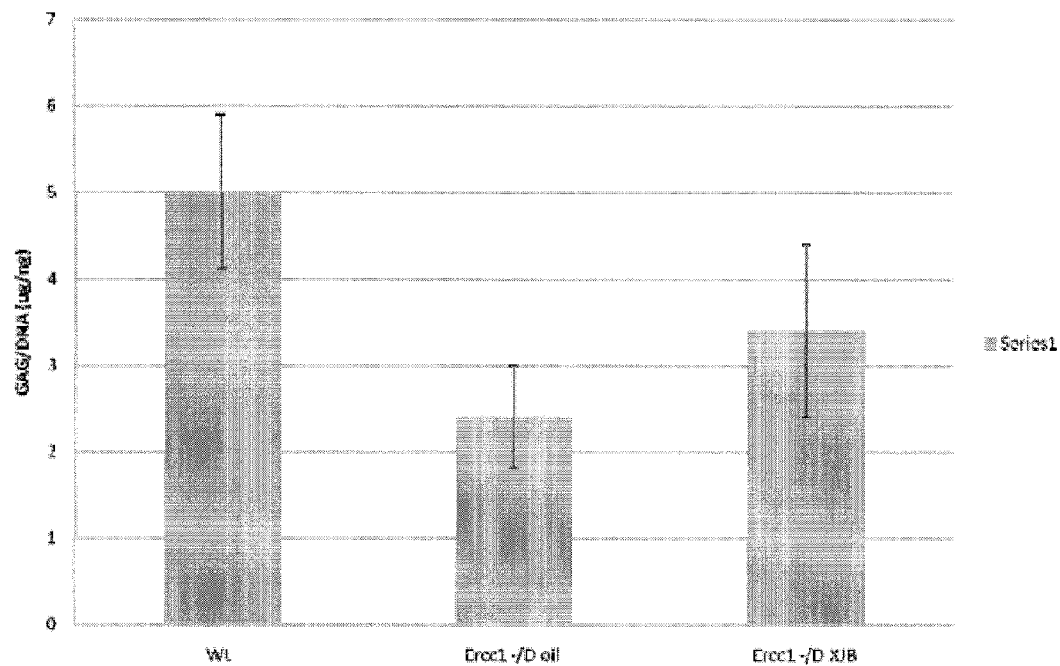
FIG. 29 is a bar graph showing glycosaminoglycan (an extracellular matrix protein that is essential for disc maintenance and flexibility) content of intervertebral discs of $Ercc1^{-/\Delta}$ mice either treated with XJB-5-131 ("XJB" in this figure) or vehicle (sunflower seed oil) according to the protocol shown in FIG. 27. The duration of treatment of mice in this figure was three times per week, beginning at 5 wks of age and continuing throughout their lifespan.
Figure 30:
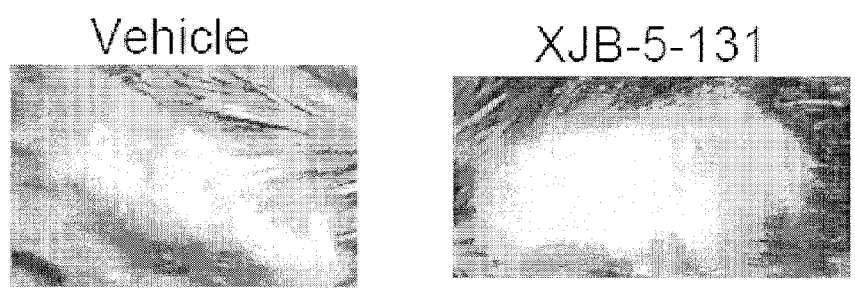
FIG. 30 provides photographs showing the effects of (photo)aging in Ercc1$^{-/\Delta}$ mice either treated with XJB-5-131 (80 μg emulsified in a topical cream) or cream only, according to the protocol shown in FIG. 27. The duration of treatment of mice in this figure was daily for five days post-UV irradiation.
Figure 31A:
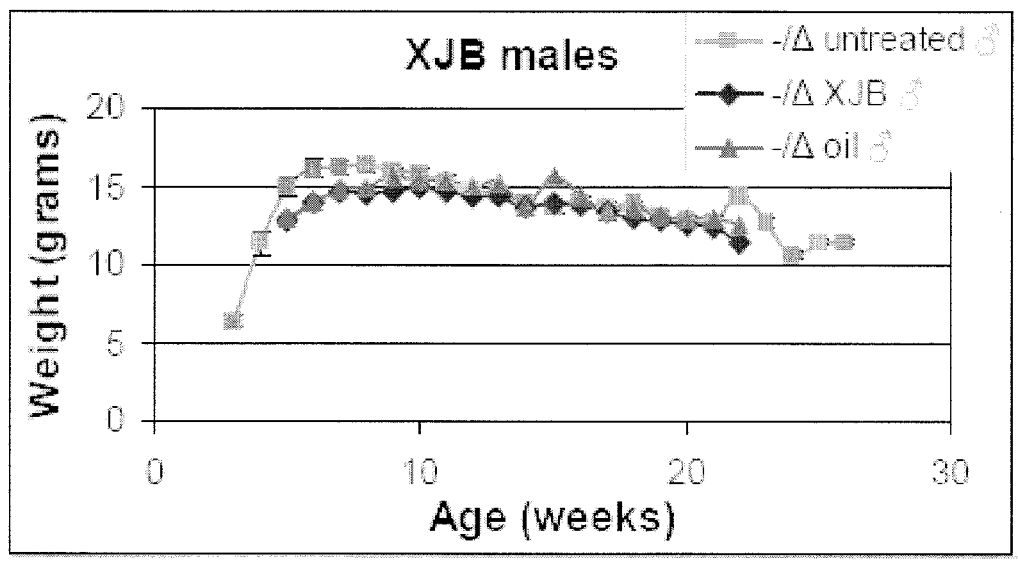
FIGS. 31A-B are graphs showing weights as a function of age of (A) male and (B) female Ercc1$^{-/\Delta}$ mice either treated with XJB-5-131 or vehicle (sunflower seed oil) according to the protocol shown in FIG. 27. XJB-5-131 does not cause weight loss as does the parental compound TEMPO.
Figure 31B:
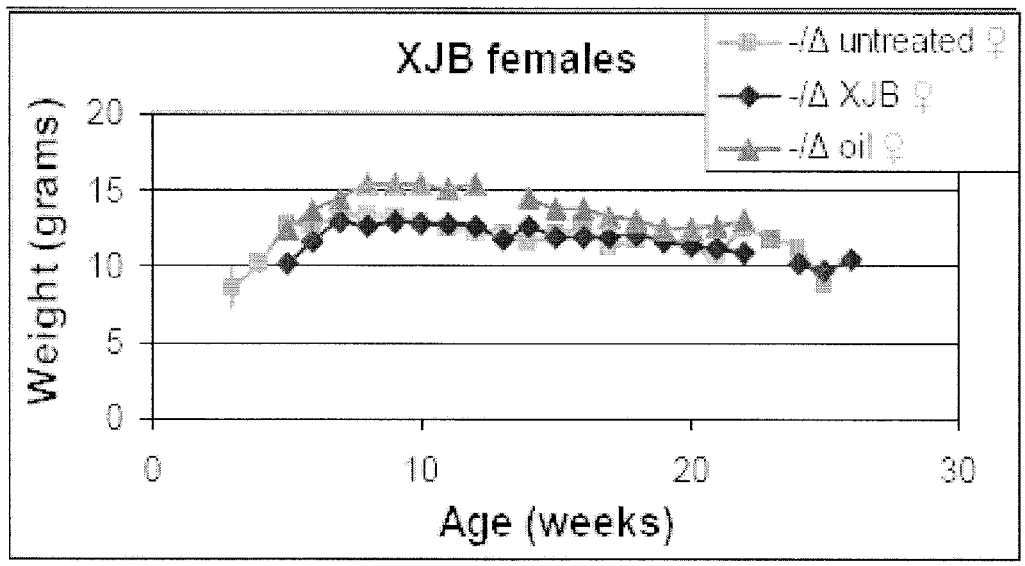

In another non-limiting embodiment, a compound is provided having the structure R1-R2-R3 in which R1 and R3 are a group having the structure -R4-R5, in which R4 is a mitochondria targeting group and R5 is —NH—R6, —O—R6 or —CH$_2$—R6, wherein R6 is an —N—O., —N—OH or N═O containing group, such as TEMPO. R1 and R2 may be the same or different. Likewise, R4 and R5 for each of R1 and R3 may be the same or different. R2 is a linker that, in one non-limiting embodiment, is symmetrical. FIGS. 26A and 26B depicts two examples of such compounds. In one embodiment, R1 and R2 have the structure shown in formulas 1, 2, or 3, above, with all groups as defined above, including structures A, A1, A2 A3, D, D1, D2 and D3, above, an example of which is compound JED-E71-58, shown in FIG. 26B. In another embodiment, R1 and R2 are, independently, a gramicidin derivative, for example, as in the compound JED-E71-37, shown in FIG. 26A. Examples of gramicidin derivatives are provided herein, such as XJB-5-131 and XJB-5-125 (see, FIG. 2), and are further described both structurally and functionally in United States Patent Publication Nos. 20070161573 and 20070161544 as well as in Jiang, J, et al. (Structural Requirements for Optimized Delivery, Inhibition of Oxidative Stress, and Antiapoptotic Activity of Targeted Nitroxides, J Pharmacol Exp Therap. 2007, 320(3): 1050-60, see also, Hoye, A T et al., Targeting Mitochondria, Acc Chem Res. 2008, 41(1):87-97, see also, Wipf, P, et al., Mitochondrial Targeting of Selective Electron Scavengers: Synthesis and Biological Analysis of Hemigramicidin-TEMPO Conjugates, (2005) J Am Chem Soc. 2005, 127:12460-12461). The XJB compounds can be linked into a dimer, for example and without limitation, by reaction with the nitrogen of the BocHN groups (e.g., as in XJB-5-131), or with an amine, if present, for instance, if one or more amine groups of the compound is not acylated to form an amide (such as NHBoc or NHCbx).

In Jiang, J, et al. (J Pharmacol Exp Therap. 2007, 320(3): 1050-60), using a model of ActD-induced apoptosis in mouse embryonic cells, the authors screened a library of nitroxides to explore structure-activity relationships between their antioxidant/antiapoptotic properties and chemical composition and three-dimensional (3D) structure. High hydrophobicity and effective mitochondrial integration were deemed necessary but not sufficient for high antiapoptotic/antioxidant activity of a nitroxide conjugate. By designing conformationally preorganized peptidyl nitroxide conjugates and characterizing their 3D structure experimentally (circular dichroism and NMR) and theoretically (molecular dynamics), they established that the presence of the β-turn/β-sheet secondary structure is essential for the desired activity. Monte Carlo simulations in model lipid membranes confirmed that the conservation of the D-Phe-Pro reverse turn in hemi-GS analogs ensures the specific positioning of the nitroxide moiety at the mitochondrial membrane interface and maximizes their protective effects. These insights into the structure-activity relationships of nitroxide-peptide and -peptide isostere conjugates are helpful in the development of new mechanism-based therapeutically effective agents, such as those described herein.

Targeting group R4 may be a membrane active peptide fragment derived from an antibiotic molecule that acts by targeting the bacterial cell wall. Examples of such antibiotics include: bacitracins, gramicidins, valinomycins, enniatins, alamethicins, beauvericin, serratomolide, sporidesmolide, tyrocidins, polymyxins, monamycins, and lissoclinum peptides. The membrane-active peptide fragment derived from an antibiotic may include the complete antibiotic polypeptide, or portions thereof having membrane, and preferably mitochondria-targeting abilities, which is readily determined, for example, by cellular partitioning experiments using radiolabeled peptides. Examples of useful gramicidin-derived membrane active peptide fragments are the Leu-D-Phe-Pro-Val-Orn and D-Phe-Pro-Val-Orn-Leu hemigramicidin fragments. As gramicidin is cyclic, any hemigramicidin 5-mer is expected to be useful as a membrane active peptide fragment, including Leu-D-Phe-Pro-Val-Orn, D-Phe-Pro-Val-Orn-Leu, Pro-Val-Orn-Leu-D-Phe, Val-Orn-Leu-D-Phe-Pro and Orn-Leu-D-Phe-Pro-Val (from Gramicidin S). Any larger or smaller fragment of gramicidin, or even larger fragments containing repeated gramicidin sequences (e.g., Leu-D-Phe-Pro-Val-Orn-Leu-D-Phe-Pro-Val-Orn-Leu-D-Phe-Pro) are expected to be useful for membrane targeting, and can readily tested for such activity. In one embodiment, the Gramicidin S-derived peptide comprises a β-turn, which appears to confer to the peptide a high affinity for mitochondria. Derivatives of Gramicidin, or other antibiotic fragments, include isosteres (molecules or ions with the same number of atoms and the same number of valence electrons—as a result, they can exhibit similar pharmacokinetic and pharmacodynamic properties), such as (E)-alkene isosteres (see, United States Patent Publication Nos. 20070161573 and 20070161544 for exemplary synthesis methods). As with Gramicidin, the structure (amino acid sequence) of bacitracins, other gramicidins, valinomycins, enniatins, alamethicins, beauvericin, serratomolide, sporidesmolide, tyrocidins, polymyxins, monamycins, and lissoclinum peptides are all known, and fragments of these can be readily prepared and their membrane-targeting abilities can easily be confirmed by a person of ordinary skill in the art.

Alkene isosteres such as (E)-alkene isosteres of Gramicidin S (i.e., hemigramicidin) were used as part of the targeting sequence. See FIG. 3 for a synthetic pathway for (E)-alkene isosteres and reference number 2 for the corresponding chemical structure. First, hydrozirconation of alkyne (FIG. 3, compound 1) with Cp$_2$ZrHCl is followed by transmetalation to Me$_2$Zn and the addition of N-Boc-isovaleraldimine. The resulting compound (not shown) was then worked up using a solution of tetrabutylammonium fluoride ("TBAF") and diethyl ether with a 74% yield. The resulting compound was then treated with acetic anhydride, triethylamine (TEA), and 4-N,N1-(dimethylamino) pyridine ("DMAP") to provide a mixture of diastereomeric allylic amides with a 94% yield which was separated by chromatography. Finally, the product was worked up with K$_2$CO$_3$ in methanol to yield the (E)-alkene, depicted as compound 2. The (E)-alkene, depicted as compound 2 of FIG. 3, was then oxidized in a multi-step process to yield the compound 3 (FIG. 3)—an example of the (E)-alkene isostere.

Figure 3:
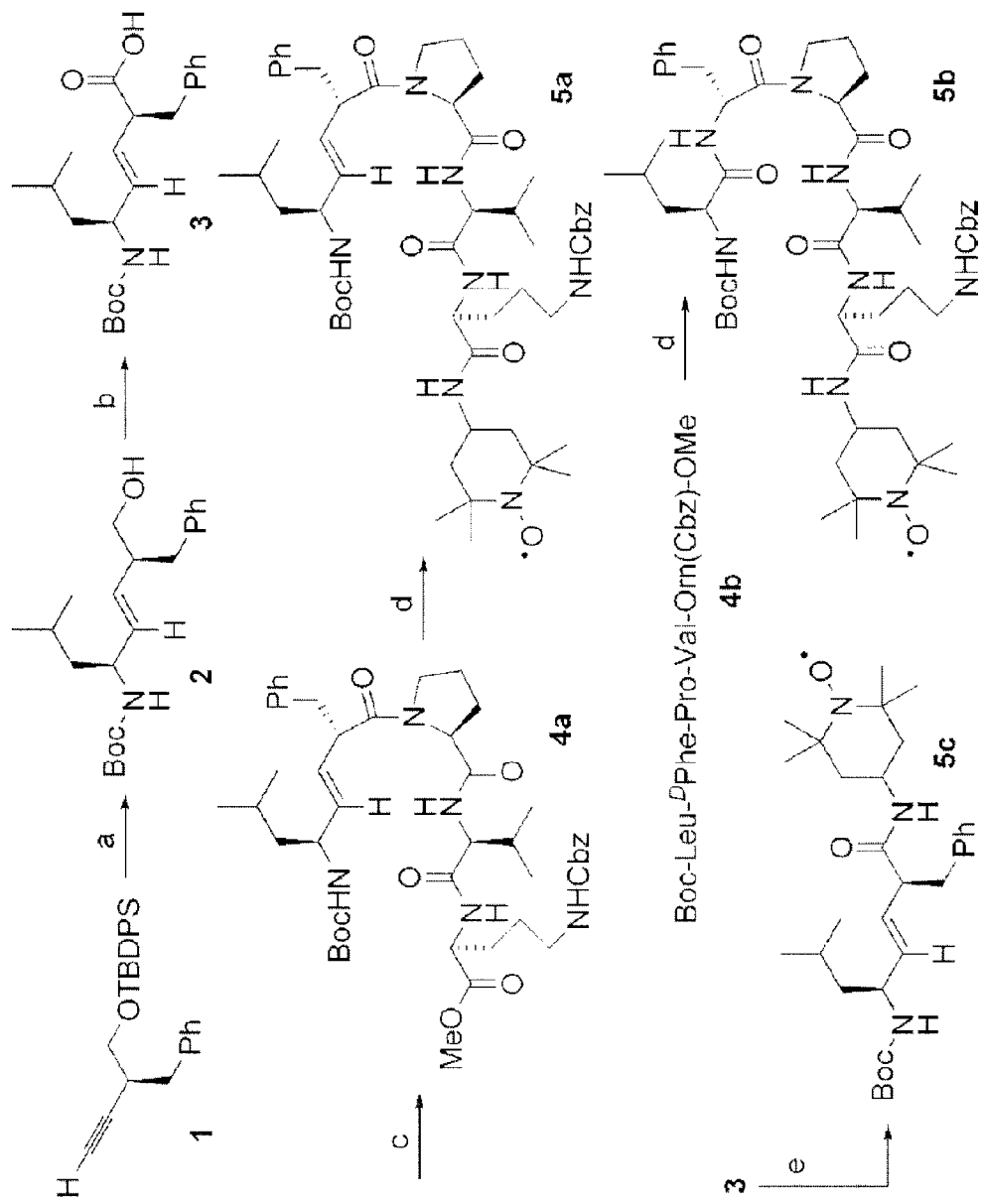
FIG. 3 depicts an example of a synthetic pathway for the TEMPO-hemigramicidin conjugates.

The compound 3 of FIG. 3 was then conjugated with the peptide H-Pro-Val-Orn(Cbz)-OMe using 1-ethyl-3-(3-dimethylaminopropyl carbodiimide hydrochloride) (EDC) as a coupling agent. The peptide is an example of a suitable targeting sequence having affinity for the mitochondria of a cell. The resulting product is shown as compound 4a in FIG. 3. Saponification of compound 4a followed by coupling with 4-amino-TEMPO (4-AT) afforded the resulting conjugate shown as compound 5a in FIG. 3, in which the Leu-DPhe peptide bond has been replaced with an (E)-alkene.

In an alternate embodiment, conjugates 5b in FIG. 3 was prepared by saponification and coupling of the peptide 4b (Boc-Leu-DPhe-Pro-Val-Orn(Cbz)-OMe) with 4-AT. Similarly, conjugate 5c in FIG. 3 was prepared by coupling the (E)-alkene isostere as indicated as compound 3 in FIG. 3 with 4-AT. These peptide and peptide analogs are additional examples of suitable targeting sequences having an affinity to the mitochondria of a cell.

In another embodiment, peptide isosteres may be employed as the conjugate. Among the suitable peptide isosteres are trisubstituted (E)-alkene peptide isosteres and cyclopropane peptide isosteres, as well as all imine addition products of hydro- or carbometalated internal and terminal alkynes for the synthesis of d-i and trisubstituted (E)-alkene and cyclopropane peptide isosteres. See Wipf et al. *Imine additions of internal alkynes for the synthesis of trisubstituted (E)-alkene and cyclopropane isosteres*, Adv Synth Catal. 2005, 347:1605-1613. These peptide mimetics have been found to act as β-turn promoters. See Wipf et al. *Convergent Approach to (E)-Alkene and Cyclopropane Peptide Isosteres*, Org Lett. 2005, 7(1):103-106.

The linker, R2, may be any useful linker, chosen for its active groups, e.g., carboxyl, alkoxyl, amino, sulfhydryl, amide, etc. Typically, aside from the active groups, the remainder is non-reactive (such as saturated alkyl or phenyl), and does not interfere, sterically or by any other physical or chemical attribute, such as polarity or hydrophobicity/hydrophilicity, in a negative (loss of function) capacity with the activity of the overall compound. In one embodiment, aside from the active groups, the linker comprises a linear or branched saturated C$_4$-C$_{20}$ alkyl. In one embodiment, the linker, R2 has the structure

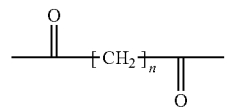

In which n is 4-18, including all integers therebetween, in one embodiment, 8-12, and in another embodiment, 10.

A person skilled in the organic synthesis arts can synthesize these compounds by crosslinking groups R1 and R3 by any of the many chemistries available. In one embodiment, R1 and R3 are to R2 by an amide linkage (peptide bond) formed by dehydration synthesis (condensation) of terminal carboxyl groups on the linker and an amine on R1 and R3 (or vice versa). In one embodiment, R1 and R3 are identical or different and are selected from the group consisting of: XJB-5-131, XJB-5-125, XJB-7-75, XJB-2-70, XJB-2-300, XJB-5-208, XJB-5-197, XJB-5-194, .JP4-039 and JP4-049, attached in the manner shown in FIGS. 26A and 26B.

In a therapeutic embodiment, a method of scavenging free-radicals in a subject (e.g., a patient in need of treatment with a free-radical scavenger) is provided, comprising administering to the subject an amount of one or more compound described herein and having a free-radical scavenging group, such as a nitroxide-containing group effective to scavenge free radicals. As described above, a number of diseases, conditions or injuries can be ameliorated or otherwise treated or prevented by administration of free radical scavenging compounds, such as those described herein.

In any case, as used herein, any agent or agents used for prevention, mitigation or treatment in a subject of injury caused by radiation exposure is administered in an amount effective to prevent, mitigate of treat such injury, namely in an amount and in a dosage regimen effective to prevent injury or to reduce the duration and/or severity of the injury resulting from radiation exposure. According to one non-limiting embodiment, an effective dose ranges from 0.1 or 1 mg/kg to 100 mg/kg, including any increment or range therebetween, including 1 mg/kg, 5 mg/kg, 10 mg/kg, 20 mg/kg, 25 mg/kg, 50 mg/kg, and 75 mg/kg. However, for each compound described herein, an effective dose or dose range is expected to vary from that of other compounds described herein for any number of reasons, including the molecular weight of the compound, bioavailability, specific activity, etc. For example and without limitation, where XJB-5-131 is the antioxidant, the dose may be between about 0.1 and 20 mg/kg, or between about 0.3 and 10 mg/kg, or between about 2 and 8 mg/kg, or about 2 mg/kg and where either JP4-039, JED-E71-37 or JED-E71-58 is the antioxidant, the dose may be between about 0.01 and 50 mg/kg, or between about 0.1 and 20 mg/kg, or between about 0.3 and 10 mg/kg, or between about 2 and 8 mg/kg, or about 2 mg/kg. The therapeutic window between the minimally-effective dose, and maximum tolerable dose in a subject can be determined empirically by a person of skill in the art, with end points being determinable by in vitro and in vivo assays, such as those described herein and/or are acceptable in the pharmaceutical and medical arts for obtaining such information regarding radioprotective agents. Different concentrations of the agents described herein are expected to achieve similar results, with the drug product administered, for example and without limitation, once prior to an expected radiation dose, such as prior to radiation therapy or diagnostic exposure to ionizing radiation, during exposure to radiation, or after exposure in any effective dosage regimen. The compounds can be administered continuously, such as intravenously, one or more times daily, once every two, three, four, five or more days, weekly, monthly, etc., including increments therebetween. A person of ordinary skill in the pharmaceutical and medical arts will appreciate that it will be a matter of simple design choice and optimization to identify a suitable dosage regimen for prevention, mitigation or treatment of injury due to exposure to radiation.

The compounds described herein also are useful in preventing, mitigating (to make less severe) and/or treating injury caused by radiation exposure. By radiation, in the context of this disclosure, it is meant types of radiation that result in the generation of free radicals, e.g., reactive oxygen species (ROS), as described herein. The free radicals are produced, for example and without limitation, by direct action of the radiation, as a physiological response to the radiation and/or as a consequence of damage/injury caused by the radiation. In one embodiment, the radiation is ionizing radiation. Ionizing radiation consists of highly-energetic particles or waves that can detach (ionize) at least one electron from an atom or molecule. Examples of ionizing radiation are energetic beta particles, neutrons, and alpha particles. The ability of light waves (photons) to ionize an atom or molecule varies across the electromagnetic spectrum. X-rays and gamma rays can ionize almost any molecule or atom; far ultraviolet light can ionize many atoms and molecules; near ultraviolet and visible light are ionizing to very few molecules. Microwaves and radio waves typically are considered to be non-ionizing radiation, though damage caused by, e.g., microwaves, may result in the production of free-radicals as part of the injury and/or physiological response to the injury.

The compounds typically are administered in an amount and dosage regimen to prevent, mitigate or treat the effects of exposure of a subject to radiation. The compounds may be administered in any manner that is effective to treat, mitigate or prevent damage caused by the radiation. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

In one embodiment, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a nonwoven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies. As is shown in Example 12, below, certain formulations that may be useful as permeation enhancers include, without limitation: DMSO; 95% Propylene Glycol+5% Linoleic Acid; and 50% EtOH+40% HSO+5% Propylene Glycol+5% Brij30.

Examples 1-7 are excerpts from United Stated patent application Ser. No. 11/565,779, and are recited herein to provide non-limiting illustrations of useful synthetic methods and efficacies of certain mitochondria-targeting free-radical scavenging compounds utilizing Gramicidin S-derived mitochondria-targeting groups.

EXAMPLE 1

Materials. All chemicals were from Sigma-Aldrich (St Louis, Mo.) unless otherwise noted. Heparin, ketamine HCl and sodium pentobarbital were from Abbott Laboratories (North Chicago, Ill.). Dulbecco's modified Eagle medium ("DMEM") was from BioWhittaker (Walkersville, Md.). Fetal bovine serum (FBS; <0.05 endotoxin units/ml) was from Hyclone (Logan, Utah). Pyrogen-free sterile normal saline solution was from Baxter (Deerfield, Ill.).

General. All moisture-sensitive reactions were performed using syringe-septum cap techniques under an N2 atmosphere and all glassware was dried in an oven at 150° C. for 2 h prior to use. Reactions carried out at −78° C. employed a $CO_2$-acetone bath. Tetrahydrofuran (THF) was distilled over sodium/benzophenone ketyl; $CH_2Cl_2$ (DCM), toluene and $Et_3N$ were distilled from $CaH_2$. $Me_2Zn$ was purchased from Aldrich Company.

Reactions were monitored by thin layer chromatography ("TLC") analysis (EM Science pre-coated silica gel 60 F254 plates, 250 µm layer thickness) and visualization was accomplished with a 254 nm UV light and by staining with a Vaughn's reagent (4.8 g $(NH_4)_6Mo7O_{24}$.$4H_2O$, 0.2 g $Ce(SO_4)_2$.$4H_2O$ in 10 mL conc. $H_2SO_4$ and 90 mL $H_2O$). Flash chromatography on $SiO_2$ was used to purify the crude reaction mixtures.

Melting points were determined using a Laboratory Devices Mel-Temp II. Infrared spectra were determined on a Nicolet Avatar 360 FT-IR spectrometer. Mass spectra were obtained on a Waters Autospec double focusing mass spectrometer ("EI") or a Waters Q-T of mass spectrometer ("ESI"). LC-MS data were obtained on an Agilent 1100 instrument, using a Waters Xterra MS CH 3.5 µm RP column (4.6×100 mm).

Synthesis, Example I. Prepared as a colorless oil (FIG. 3, compound 1) according to the literature procedure, see Edmonds, M. K. et al. *Design and Synthesis of a Conformationally Restricted Trans Peptide Isostere Based on the Bioactive Conformations of Saquinavir and Nelfinavir*, J Org Chem. 66:3747 (2001); see also Wipf P. et al., Org Lett. 7:103 (2005); see also Xiao, J. et al., *Electrostatic versus Steric Effects in Peptidomimicry: Synthesis and Secondary Structure Analysis of Gramicidin S Analogues with (E)-Alkene Peptide Isosteres*, J Am Chem Soc. 127:5742 (2005).

A solution of 2.20 g (5.52 mmol) of compound 1 (FIG. 3) in 20.0 mL of dry $CH_2Cl_2$ was treated at room temperature with 1.85 g (7.17 mmol) of $Cp_2ZrHCl$. The reaction mixture was stirred at room temperature for 5 min, $CH_2Cl_2$ was removed in vacuo and 20.0 mL of toluene was added. The resulting yellow solution was cooled to −78° C. and treated over a period of 30 min with 2.76 mL (5.52 mmol) of $Me_2Zn$ (2.0 M solution in toluene). The solution was stirred at −78° C. for 30 min, warmed to 0° C. over a period of 5 min and treated in one portion with 2.05 g (11.1 mmol) of N-Boc-isovaleraldimine, see Edmonds, M. K. et al. J Org Chem. 66:3747 (2001); see also Wipf P. et al., J Org Lett. 7:103 (2005); see also Xiao et al., J Am Chem Soc. 127:5742 (2005).

The resulting mixture was stirred at 0° C. for 2 h, quenched with saturated $NH_4Cl$, diluted with EtOAc, filtered through a thin pad of Celite, and extracted with EtOAc. The organic layer was dried ($MgSO_4$), concentrated in vacuo, and purified by chromatography on $SiO_2$ (20:1, hexane/EtOAc) to yield 3.13 g (97%) as a colorless, oily 1:1 mixture of diastereomers.

A solution of 4.19 g (7.15 mmol) of product in 100 mL of dry tetrahydrofuran ("THF") was treated at 0° C. with 9.30 mL (9.30 mmol) of tetrabutylammoniumfluoride (TBAF, 1.0 M solution in THF). The reaction mixture was stirred at room temperature for 20 h, diluted with EtOAc, and washed with brine. The organic layer was dried ($MgSO_4$), concentrated in vacuo, and purified by chromatography on $SiO_2$ (4:1, hexane/EtOAc) to yield 1.89 g (76%) as a light yellowish, foamy 1:1 mixture of diastereomers.

A solution of 1.86 g (5.23 mmol) of product in 40.0 mL of dry $CH_2Cl_2$ was treated at 0° C. with 1.46 mL (10.5 mmol) of triethylamine ("TEA"), 2.02 mL (21.4 mmol) of $Ac_2O$, and 63.9 mg (0.523 mmol) of 4-N,N'-(dimethylamino)pyridine ("DMAP"). The reaction mixture was stirred at 0° C. for 15 min and at room temperature for 3 h, diluted with EtOAc, and washed with brine. The organic layer was dried ($MgSO_4$), concentrated in vacuo, and purified by chromatography on $SiO_2$ (20:1, hexane/$Et_2O$) to yield 1.97 g (94%) of acetic acid (2S)-benzyl-(5R)-tert-butoxycarbonylamino-7-methyloct-(3E)-enyl ester (807 mg, 38.7%), acetic acid (2S)-benzyl-(5S)-tert-butoxycarbonylamino-7-methyloct-(3E)-enyl ester (826 mg, 39.6%), and a mixture of the aforementioned species (337 mg, 16.2%).

A solution of 350 mg (0.899 mmol) of acetic acid (2S)-benzyl-(5S)-tert-butoxycarbonylamino-7-methyloct-(3E)-enyl ester in 8.00 mL of MeOH was treated at 0° C. with 62.0 mg (0.449 mmol) of $K_2CO_3$. The reaction mixture was stirred at 0° C. for 1 h and at room temperature for an additional 4 h, diluted with EtOAc, and washed with $H_2O$. The organic layer was dried ($MgSO_4$), concentrated in vacuo, and purified by chromatography on $SiO_2$ (4:1, hexane/EtOAc) to yield 312 mg (quant.) of compound 2 (FIG. 3) as a colorless oil.

A solution of 23.0 mg (66.2 µmol) of compound 2 (FIG. 3) in 2.00 mL of dry $CH_2Cl_2$ was treated at 0° C. with 42.1 mg (99.3 µmol) of Dess-Martin Periodinane. The reaction mixture was stirred at 0° C. for 1 h and at room temperature for an additional 4 h, quenched with saturated $Na_2S_2O_3$ in a saturated $NaHCO_3$ solution, stirred for 30 min at room temperature, and extracted with $CH_2Cl_2$. The organic layer was dried ($Na_2SO_4$), concentrated in vacuo to give a colorless foam and subsequently dissolved in 3.00 mL of THF, and treated at 0° C. with 300 µL (600 µmol) of 2-methyl-2-butene (2.0 M solution in THF) followed by another solution of 18.0 mg (199 µmol) of $NaClO_2$ and 18.2 mg (132 µmol) of $NaH_2PO_4 \cdot H_2O$ in 3.00 mL of $H_2O$. The reaction mixture was stirred at 0° C. for 1 h and at room temperature for an additional 3 h, extracted with EtOAc, and washed with $H_2O$. The organic layer was dried ($Na_2SO_4$) and concentrated in vacuo to yield compound 3 (FIG. 3) as a crude colorless foam that was used for the next step without purification.

A solution of crude compound 3 (FIG. 3) (66.2 µmol) in 3.00 mL of $CHCl_3$ was treated at 0° C. with 10.7 mg (79.2 µmol) of 1-hydroxybenzotrizole ("HOBt") and 14.0 mg (73.0 µmol) of 1-ethyl-3-(3-dimethylaminopropyl) carbodiimide hydrochloride ("EDC"), followed by a solution of 62.9 mg (132 µmol) of H-Pro-Val-Orn(Cbz)-OMc, see Edmonds, M. K. et al J Org Chem 66:3747 (2001); see also Wipf P. et al., J Org Lett. 7:103 (2005); see also Xiao, J. et al., J Am Chem Soc. 127:5742 (2005), in 1.00 mL of $CHCl_3$ and 0.8 mg (6.6 µmol) of DMAP. The reaction mixture was stirred at room temperature for 2 d, diluted with $CHCl_3$, and washed with $H_2O$. The organic layer was dried ($Na_2SO_4$), concentrated in vacuo, and purified by chromatography on $SiO_2$ (from 2:1, hexanes/EtOAc to 20:1, $CHCl_3$/MeOH) to yield 51.3 mg (94%) of compound 4a (FIG. 3) as a colorless foam.

A solution of 53.7 mg (65.5 µmol) of compound 4a (FIG. 3) in 2.00 mL of MeOH was treated at 0° C. with 655 µL (655 µmol) of 1 N NaOH. The reaction mixture was stirred at room temperature for 6 h, and treated with 655 µL (655 µmol) of 1 N HCl. The solution was extracted with $CHCl_3$ and the organic layer was dried ($Na_2SO_4$) and concentrated in vacuo to give the crude acid as a colorless form. This acid was dissolved in 5.00 mL of $CHCl_3$ and treated at room temperature with 10.6 mg (78.4 µmol) of HOBt, 15.1 mg (78.8 µmol) of EDC, 20.2 mg (118 µmol) of 4-amino-TEMPO and 8.0 mg (65.5 µmol) of DMAP. The reaction mixture was stirred at room temperature for 36 h, diluted with $CHCl_3$, and washed with $H_2O$. The organic layer was dried ($Na_2SO_4$), concentrated in vacuo, and purified by chromatography on $SiO_2$ (from 1:1, hexane/EtOAc to 20:1, $CHCl_3$/MeOH) to yield 62.0 mg (99%) of compound 5a (FIG. 3) as a colorless solid. The following characterization data were obtained: LC-MS (Rt 8.81 min, linear gradient 70% to 95% $CH_3CN(H_2O)$ in 10 min, 0.4 mL/min; m/z=959.5 [M+H]$^+$, 981.5 [M+Na]$^+$) and HRMS (ESI) m/z calculated for $C_{53}H_{80}N_7O_9Na$ (M+Na) 981.5915, found 981.5956.

A solution of 60.0 mg (71.7 µmol) of compound 4b (FIG. 3), see Tamaki, M. et al. I. Bull Chem Soc Jpn., 66:3113 (1993), in 2.15 mL of MeOH was treated at room temperature with 717 µL (717 µmol) of 1 N NaOH. The reaction mixture was stirred at room temperature for 5 h, and treated at 0° C. with 717 µL (717 µmol) of 1 N HCl. The solution was extracted with $CHCl_3$ and the organic layer was dried ($Na_2SO_4$) and concentrated in vacuo to give the crude acid as colorless foam. The acid was dissolved in 6.04 mL of $CHCl_3$ and treated at room temperature with 11.6 mg (85.8 µmol) of HOBt, 16.5 mg (85.1 µmol) of EDC, 18.5 mg (108 µmol) of 4-amino-TEMPO and 8.8 mg (72.0 µmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 2:1, hexane/EtOAc; to 20:1, $CHCl_3$/MeOH) to yield 69.6 mg (99%) of compound 5b (FIG. 3) as a yellowish solid. The following characterization data were obtained: LC-MS (Rt 7.02 min, linear gradient 70% to 95% $CH_3CN$ ($H_2O$) in 10 min, 0.4 mL/min; m/z=976.5 $[M+H]^+$, 998.4 $[M+Na]^+$) and HRMS (ESI) m/z calculated for $C_{52}H_{79}N_8O_{10}Na$ (M+Na) 998.5817, found 998.5774.

A solution of crude compound 3 (FIG. 3) (40.3 μmol) in 3.00 mL of $CH_2Cl_2$ was treated at 0° C. with 10.4 mg (60.7 μmol) of 4-amino-TEMPO, 7.7 mg (40.2 μmol) of EDC, and 5.4 mg (44.2 μmol) of DMAP. The reaction mixture was stirred at room temperature for 20 h, diluted with $CHCl_3$, and washed with $H_2O$. The organic layer was dried ($Na_2SO_4$), concentrated in vacuo, and purified by chromatography on $SiO_2$ (from 4:1 to 1:1, hexane/EtOAc) to yield 18.8 mg (91%) of compound 5c (FIG. 3) as a yellowish solid. The following characterization data were obtained: LC-MS (Rt 7.01 min, linear gradient 70% to 95% $CH_3CN(H_2O)$ in 10 min, 0.4 mL/min; m/z=537.3 $[M+Na]^+$) and HRMS (ESI) m/z calculated for $C_{30}H_{48}N_3O_4Na$ (M+Na) 537.3543, found 537.3509.

Determination of intracellular superoxide radicals Oxidation-dependent fluorogenic dye, dihydroethidium ("DHE", Molecular Probes) was used to evaluate intracellular production of superoxide radicals. DHE is cell permeable and, in the presence of superoxide, is oxidized to fluorescent ethidium which intercalates into DNA. The fluorescence of ethidium was measured using a FACscan (Becton-Dickinson, Rutherford, N.J.) flow cytometer, equipped with a 488-nm argon ion laser and supplied with the Cell Quest software. Mean fluorescence intensity from 10,000 cells were acquired using a 585-nm bandpass filter (FL-2 channel).

Determination of intracellular ATP levels. Cells were incubated with 10 μm of compound 5a (FIG. 3) for indicated periods of time (2, 4, 6, 12, and 14 h). At the end of incubation, cells were collected and the content of intracellular ATP was determined using a bioluminescent somatic cell assay kit (Sigma, St. Louis, Mass.). As a positive control, cells were incubated with 2 mM of 2-dexy-glucose, a glucose analogue which competitively inhibits cellular uptake and utilization of glucose, for 12 and 14 h.

Cells. Caco-2BBe human enterocyte-like epithelial cells were obtained from the American Type Culture Collection (Manassas, Va.). Cells were routinely maintained at 37° C. in under a humidified atmosphere containing 8% $CO_2$ in air. The culture medium was DMEM supplemented with 10% FBS, non-essential amino acids supplement (Sigma-Aldrich catalogue #M7145), sodium pyruvate (2 mM), streptomycin (0.1 mg/ml), penicillin G (100 U/ml) and human transferrin (0.01 mg/ml). The culture medium was changed 3 times per week.

Surgical procedures to obtain vascular access. All study protocols using rats followed the guidelines for the use of experimental animals of the US National Institutes of Health and were approved by the Institutional Animal Care and Use Committee at the University of Pittsburgh.

Male specific pathogen-free Sprague Dawley rats (Charles River Laboratories, Wilmington, Mass.), weighing 150-250 g, were housed in a temperature-controlled environment with a 12-h light/dark cycle. The rats had free access to food and water. For experiments, rats were anesthetized with intramuscular ketamine HCl (30 mg/kg) and intraperitoneal sodium pentobarbital (35 mg/kg). Animals were kept in a supine position during the experiments. Lidocaine (0.5 ml of a 0.5% solution) was injected subcutaneously to provide local anesthesia at surgical cut-down sites. In order to secure the airway, a tracheotomy was performed and polyethylene tubing (PE 240; Becton Dickinson, Sparks, Md.) was introduced into the trachea. Animals were allowed to breathe spontaneously.

The right femoral artery was cannulated with polyethylene tubing (PE 10). This catheter was attached to a pressure transducer that allowed instantaneous measurement of mean arterial pressure (M A P) during the experiment. For experiments using the pressure-controlled hemorrhagic shock (HS) model, the right jugular vein was exposed, ligated distally, and cannulated with polyethylene tubing (PE 10) in order to withdraw blood. For experiments using the volume-controlled hemorrhagic shock (HS) model, the jugular catheter was used to infuse the resuscitation solution and the right femoral vein, which was cannulated with a silicon catheter (Chronic-Cath, Norfolk Medical, Skokie, Ill.), was used to withdraw blood.

All animals were instrumented within 30 min. Heparin (500 U/kg) was administered immediately after instrumentation through the femoral vein. Animals were placed in a thermal blanket to maintain their body temperature at 37° C. The positioning of the different devices aforementioned was checked postmortem.

Intestinal mucosal permeability assay. Animals were allowed access to water but not food for 24 h prior to the experiment in order to decrease the volume of intestinal contents. The rats were instrumented as described above. A midline laparotomy was performed and the small intestine was exteriorized from the duodenojejunal junction to the ileocecal valve. A small incision was made on the antimesenteric aspect of the proximal small intestine and saline solution (1.5 ml) was injected. The bowel was ligated proximally and distally to the incision with 4-0 silk (Look, Reading, Pa.).

The small intestine was compressed gently in aboral direction along its length to displace intestinal contents into the colon. Starting 5 cm from the ileocecal valve, the ileum was partitioned into six contiguous water-tight segments. Each segment was 3 cm long and was bounded proximally and distally by constricting circumferential 4-0 silk sutures. Care was taken to ensure that the vascular supply to intestine was not compromised, and each segment was well-perfused.

Two randomly selected segments in each rat were injected with 0.3 ml of vehicle and served as "no treatment" controls. In order to fill the segments, a small incision was made and the solution was injected using a Teflon catheter (Abbocath 16Ga, Abbot Laboratories).

The remaining four other segments were injected with solutions containing either 4-hydroxy-2,2,6,6-tetramethylpiperidine-N-oxyl (TEMPOL) or one of the Gramicidin S-based compounds. Four different final concentrations of TEMPOL in normal saline were evaluated: 0.1, 1, 5 and 20 mM. The hemigramicidin-based compounds were dissolved in a mixture of dimethylsulfoxide (DMSO) and normal saline (1:99 v/v) and injected at final concentrations of 0.1, 1, 10 or 100 μM.

After the segments were loaded with saline or the test compounds, the bowel was replaced inside the peritoneal cavity and the abdominal incision was temporarily closed using Backhaus forceps.

After a 5 min stabilization period, hemorrhagic shock was induced by withdrawing blood via the jugular catheter. MAP was maintained at 30±3 mm Hg for 2 hours. The shed blood was re-infused as needed to maintain MAP within the desired range.

After 2 h of shock, the animals were euthanized with an intracardiac KCl bolus injection. The ileum was rapidly excised from the ileocecal valve to the most proximal gut segment. The tips of each segment were discarded. In order to assay caspases 3 and 7 activity and phospholipids peroxidation, mucosa samples were collected from gut segments immediately after hemorrhage and stored at −80° C. For permeability measurements, each segment was converted into an everted gut sac, as previously described by Wattanasirichaigoon et al., see Wattanasirichaigoon, S. et al., *Effect of*

*mesenteric ischemia and reperfusion or hemorrhagic shock on intestinal mucosal permeability and ATP content in rats*, Shock. 12:127-133 (1999).

Briefly, as per the Wattanasirichaigoon protocol referenced above, the sacs were prepared in ice-cold modified Krebs-Henseleit bicarbonate buffer ("KHBB"), pH 7.4. One end of the gut segment was ligated with a 4-0 silk suture; the segment was then everted onto a thin plastic rod. The resulting gut sac was mounted on a Teflon catheter (Abbocath 16GA, Abbot Laboratories) connected to a 3 ml plastic syringe containing 1.5 ml of KHBB. The sac was suspended in a beaker containing KHBB plus fluorescein-isothiocyanate labeled dextran (average molecular mass 4 kDa; FD4; 0.1 mg/ml). This solution was maintained at 37° C., and oxygenated by bubbling with a gas mixture ($O_2$ 95%/$CO_2$ 5%). After 30 min, the fluid within the gut sac was collected. The samples were cleared by centrifugation at 2000 g for 5 min.

Fluorescence of FD4 in the solution inside the beaker and within each gut sac was measured using a fluorescence spectrophotometer (LS-50, Perkin-Elmer, Palo Alto, Calif.) at an excitation wavelength of 492 nm and an emission wavelength of 515 nm. Mucosal permeability was expressed as a clearance normalized by the length of the gut sac with units of $nL \cdot min^{-1} \cdot cm^2$, as previously described, see Yang, R. et al., *Ethyl pyruvate modulates inflammatory gene expression in mice subjected to hemorrhagic shock*, Am J Physiol Gastrointest Liver Physiol 283:G212-G22 (2002).

Results for a specific experimental condition (i.e., specific test compound at a single concentration) were expressed as relative change in permeability calculated according to this equation: Relative change in permeability (%)=$(C_{Hs\ exp} - C_{normal})/(C_{HS\ cont} - C_{normal}) \times 100$, where $C_{HS\ exp}$ is the clearance of FD4 measured for a gut segment loaded with the experimental compound, $C_{normal}$ is the clearance of FD4 measured in 6 gut segments from 3 normal animals not subjected to hemorrhagic shock, and $C_{HS\ cont}$ is the mean clearance of FD4 measured in 2 gut segments filled with vehicle from the same animal used to measure $C_{HS\ exp}$.

Measurement of permeability of Caco-2 monolayers. Caco-$2_{BBc}$ cells were plated at a density of $5 \times 10^4$ cells/well on permeable filters (0.4 μm pore size) in 12-well bicameral chambers (Transwell, Costar, Corning, N.Y.). After 21 to 24 days, paracellular permeability was determined by measuring the apical-to-basolateral clearance of FD4.

Briefly, the medium on the basolateral side was replaced with control medium or medium containing menadione (50 μM final). Medium containing FD4 (25 mg/ml) was applied to the apical chamber. In some cases, one of the gramicidin S-based compounds, XJB-5-131, also was added to the apical side at final concentrations of 0.1, 1, 10 or 100 μM. After 6 hours of incubation, the medium was aspirated from both compartments. Permeability of the monolayers was expressed as a clearance ($pL \cdot h^{-1} \cdot cm^{-2}$), see Han, X. et al., *Proinflammatory cytokines cause NO dependent and independent changes in expression and localization of tight junction proteins in intestinal epithelial cells*, Shock. 19:229-237 (2003).

Caspases 3 and 7 activity assay. Caspases 3 and 7 activity was measured using a commercially available assay kit, Caspase Glo™ 3/7 assay kit (Promega, Madison, Wis.). Briefly, 50 μl of rat gut mucosa homogenate (20 jug protein) was mixed with 50 μl of Caspase-Glo™ reagent and incubated at room temperature for 1 hour. At the end of incubation period, the luminescence of each sample was measured using a plate reading chemiluminometer (ML1000, Dynatech Laboratories, Horsham, Pa.). Activity of caspases 3 and 7 was expressed as luminescence intensity (arbitrary units per mg protein). Protein concentrations were determined using the BioRad assay (Bio-Rad Laboratories, Inc., Hercules, Calif.).

Assay for peroxidation of phospholipids. Gut mucosal samples were homogenized. Lipids were extracted from homogenates using the Folch procedure, see M. Lees and G. H. Sloan-Stanley, *A simple method for isolation and purification of total lipids from animal tissue*, J. BIOL. CHEM. 226:497-509 (1957), and resolved by 2D HPTLC (High Performance Thin Layer Chromatography) as previously described, see Kagan, V. E. et al., *A role for oxidative stress in apoptosis: Oxidation and externalization of phosphatidylserine is required for macrophage clearance of cell undergoing Fas-mediated apoptosis*, J. Immunol. 169:487-489 (2002). Spots of phospholipids were scraped from HPTLC plates and phospholipids were extracted from silica. Lipid phosphorus was determined by a micro-method, see Bottcher, C. J. F. et al., *A rapid and sensitive sub-micro phosphorus determination*, Anal Chim Acta. 24: 203-204 (1961).

Oxidized phospholipids were hydrolyzed by pancreatic phospholipase A2 (2 U/μl) in 25 mM phosphate buffer containing 1 mM $CaCl_2$, 0.5 mM EDTA and 0.5 mM sodium dodecyl sulfate (SDS) (pH 8.0, at room temperature for 30 min). Fatty acid hydroperoxides formed were determined by fluorescence HPLC of resorufin stoichiometrically formed during their microperoxidase 11-catalyzed reduction in presence of Amplex Red (for 40 min at 4° C.) (8). Fluorescence HPLC (Eclipse XDB-C18 column, 5 μm, 150×4.6 mm, mobile phase was composed of 25 mM disodium phosphate buffer (pH 7.0)/methanol (60:40 v/v); excitation wavelength 560 nm, emission wavelength 590 nm) was performed on a Shimadzu LC-100AT HPLC system equipped with fluorescence detector (RF-10Ax1) and autosampler (SIL-10AD).

Survival of rats subjected to volume-controlled hemorrhagic shock. Following surgical preparation and a 5-min stabilization period to obtain baseline readings, rats were subjected to hemorrhagic shock. Bleeding was carried out in 2 phases.

Initially, 21 ml/kg of blood was withdrawn over 20 min. Immediately thereafter, an additional 12.5 ml/kg of blood was withdrawn over 40 min. Thus, hemorrhage occurred over a total period of 60 min and the total blood loss was 33.5 ml/kg or approximately 55% of the total blood volume. Rats were randomly assigned to receive XJB-5-131 (2 μmol/kg) or its vehicle, a 33:67 (v/v) mixture of DMSO and normal saline. XJB-5-131 solution or vehicle alone was administered as a continuous infusion during the last 20 min of the hemorrhage period. The total volume of fluid infused was 2.8 ml/kg and it was administered intravenously using a syringe pump (KD100, KD Scientific, New Hope, Pa.). Rats were observed for 6 hours or until expiration (defined by apnea for >1 min). At the end of the 6 hour observation period, animals that were still alive were euthanized with an overdose of KCl.

Blood pressure was recorded continuously using a commercial strain-gauge transducer, amplifier, and monitor (S90603a, SpaceLabs, Redmond, Wash.). Blood samples (0.5 ml) were collected from the jugular vein at the beginning of hemorrhage (baseline), at the end of hemorrhage (shock) and at the end of resuscitation (resuscitation). Hemoglobin concentration [Hb], lactate and glucose concentration were determined using an auto-analyzer (Model ABL 725, Radiometer Copenhagen, Westlake, Ohio).

Data presentation and statistics. All variables are presented as means±Standard Error Mean (SEM). Statistical significance of differences among groups was determined using ANOVA (analysis of variance) and LSD (Least Significant Difference) tests, or Kruskal-Wallis and Mann-Whitney tests as appropriate. Survival data were analyzed using the log-rank test. Significance was declared for p values less than 0.05.

EXAMPLE 2

Selective delivery of TEMPO to mitochondria could lead to therapeutically beneficial reduction of ROS; therefore, investigation of the use of conjugates of 4-amino-TEMPO ("4-AT") was explored. In order to selective target the mitochondria, a targeting sequence using the membrane active antibiotic Gramicidin S ("GS") as well as corresponding alkene isosteres, shown in FIGS. 2 and 3. Accordingly, using the Gramicidin S peptidyl fragments and alkene isosteres as "anchors," the TEMPO "payload" could be guided into the mitochondria.

The Leu-$^D$Phe-Pro-Val-Orn fragment of hemigramicidin was used as a targeting sequence. Alkene isosteres such as (E)-alkene isosteres of Gramicidin S (i.e., hemigramicidin) were used as part of the targeting sequence. See FIG. 3 for the synthetic pathway for (E)-alkene isosteres and compound 3 for the corresponding chemical structure. The (E)-alkene as depicted in compound 2 of FIG. 3 was then oxidized in a multi-step process to yield the compound as depicted in compound 3 an example of the (E)-alkene isostere.

Then, the compound depicted as compound 3 of FIG. 3 was conjugated with the tripeptide H-Pro-Val-Orn(Cbz)-OMe using 1-ethyl-3-(3-dimethylaminopropyl) carbodiimide hydrochloride ("EDC") as a coupling agent. The tripeptide is an example of a suitable targeting sequence having affinity for the mitochondria of a cell. The resulting product is shown as compound 4a in FIG. 3. Saponification of compound 4a followed by coupling with 4-amino-TEMPO ("4-AT") afforded the resulting conjugates shown as compound 5a in FIG. 3, in which the Leu-$^D$Phe peptide bond has been replaced with an (E)-alkene.

Figure 4:
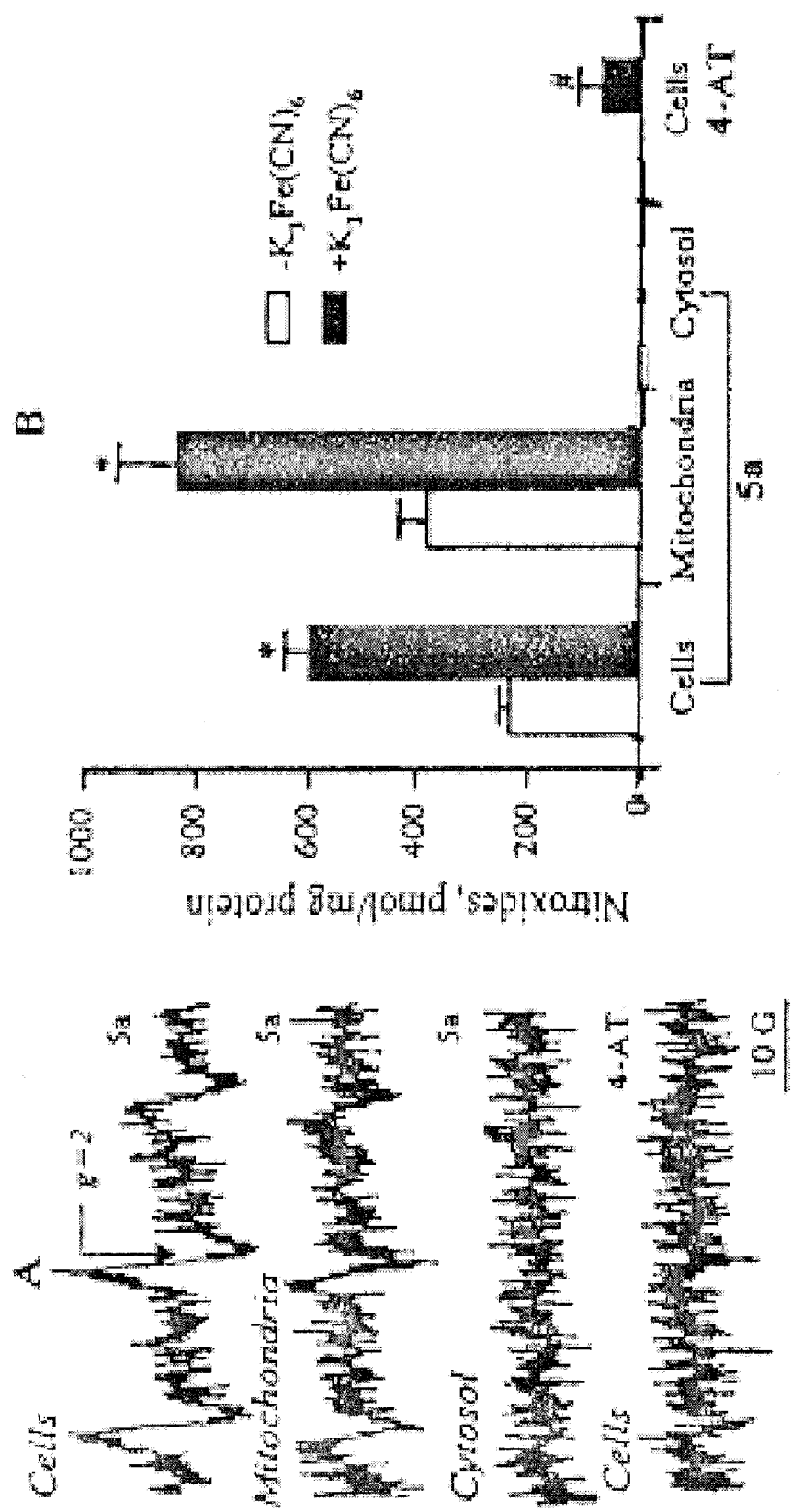
FIG. 4 shows an EPR-based analysis of integration and reduction of nitroxide Gramicidin S peptidyl-TEMPO conjugates in MECs.

In an alternate embodiment, conjugates 5b and 5c in FIG. 3 by coupling the peptide 4b (Boc-Leu-$^D$Phe-Pro-Val-Orn (Cbz)-OMe) and the (E)-alkene isostere as indicated as compound 3 in FIG. 3 to 4-AT. The peptide is another example of a suitable targeting sequence having an affinity with the mitochondria of a cell.

Electron paramagnetic resonance ("EPR") spectroscopy was used to monitor the cellular delivery of compounds 5a and 5b shown in FIG. 3 in mouse embryonic cells ("MEC").

The following conditions were used during the EPR-based analysis of the integration and reduction of nitroxide Gramicidin S-peptidyl conjugates in MECs. The MECs at a concentration of 10 million MECs per mL were incubated with 10 µM of 4-AT and compound 5a, respectively. Recovered nitroxide radicals in whole cells, mitochondria, and cytosol fractions were resuspended in phosphate buffer saline ("PBS") in the presence and absence, respectively, of 2 µM $K_3Fe(CN)_6$. In brief, FIG. 4A shows a representative EPR spectra of compound 5a in different fractions of MECs in the presence of $K_3Fe(CN)_6$. Further, FIG. 4B shows an assessment of integrated nitroxides.

Distinctive characteristic triplet signals of nitroxide radicals were detected in MECs incubated with 10 µM of compound 5a (FIG. 3) as well as in mitochondria isolated from these cells. The cytosolic function did not elicit EPR signals of nitroxide radicals; similar results were observed with conjugate 5b (FIG. 3) (data not shown).

Incubation of MECs with compound 5a (FIG. 3) resulted in integration and one-electron reduction of compound 5a, as evidenced by a significant increase in magnitude of the EPR signal intensity upon addition of a one-electron oxidant, ferricyanide (FIG. 4B). (Note: EPR results for incubation of MECs with 5b are not shown in FIG. 4; however, EPR results for 5b were similar when compared to 5a). In contrast to 5a and 5b, however, 4-amino-TEMPO (4-AT) did not effectively permeate cells or the mitochondria, as shown by the absence of significant amplitude change in the EPR results for 4-AT.

The ability of 5a, 5b (FIG. 3), and 4-AT to prevent intracellular superoxide generation by flow cytometric monitoring of oxidation of dihydroethidium ("DHE") to a fluorescent ethidium was tested. The ability of 5a, 5b, and 4-AT to protect cells against apoptosis triggered by actinomycin D ("ActD") was also tested. MECs were pretreated with 10 µM 4-AT, 5a, or 5b then incubated with ActD at a concentration of 100 ng/mL. It was found that 5a and 5b completely inhibited nearly two-fold intracellular superoxide generation in MECs (sec FIG. 6A). 4-AT had no effect on the superoxide production in MECs.

Apoptotic cell responses were documented using three biomarkers: (1) externalization of phosphatidylserine ("PS") on the cell surface (by flow cytometry using an FITC-labeled PS-binding protein, annexin V, see FIGS. 6B and 6E); (2) activation of caspase-3 by cleavage of the Z-DEVD-AMC substrate (see FIG. 6C), and, (3) DNA fragmentation by flow cytometry of propidium iodide stained DNA (see FIG. 6D).

Phosphatidylserine ("PS") is an acidic phospholipid located exclusively on the inner leaflet of the plasma membrane; exposure of PS on the cell surface is characteristic of cell apoptosis. Externalization of PS was analyzed by flow cytometry using an annexin V kit. Cells were harvested by trypsinization at the end of incubation and then stained with annexin V-FITC and propidium iodide ("PS"). Ten thousand cell events were collected on a FACScan flow cytometer. Annexin V-positive and PI-negative cells were considered apoptotic.

Activation of capase-3, a cysteine protease only activated in the execution phase of apoptosis, was determined using an EnzChek capsase-3 assay kit.

Further, calcium and magnesium dependent nucleases are activated that degrade DNA during apoptosis. These DNA fragments are eluted, stained with propidium iodide and analyzed using flow cytometry. A cell population with decreased DNA content was considered a fraction of apoptotic cells.

Figure 6:
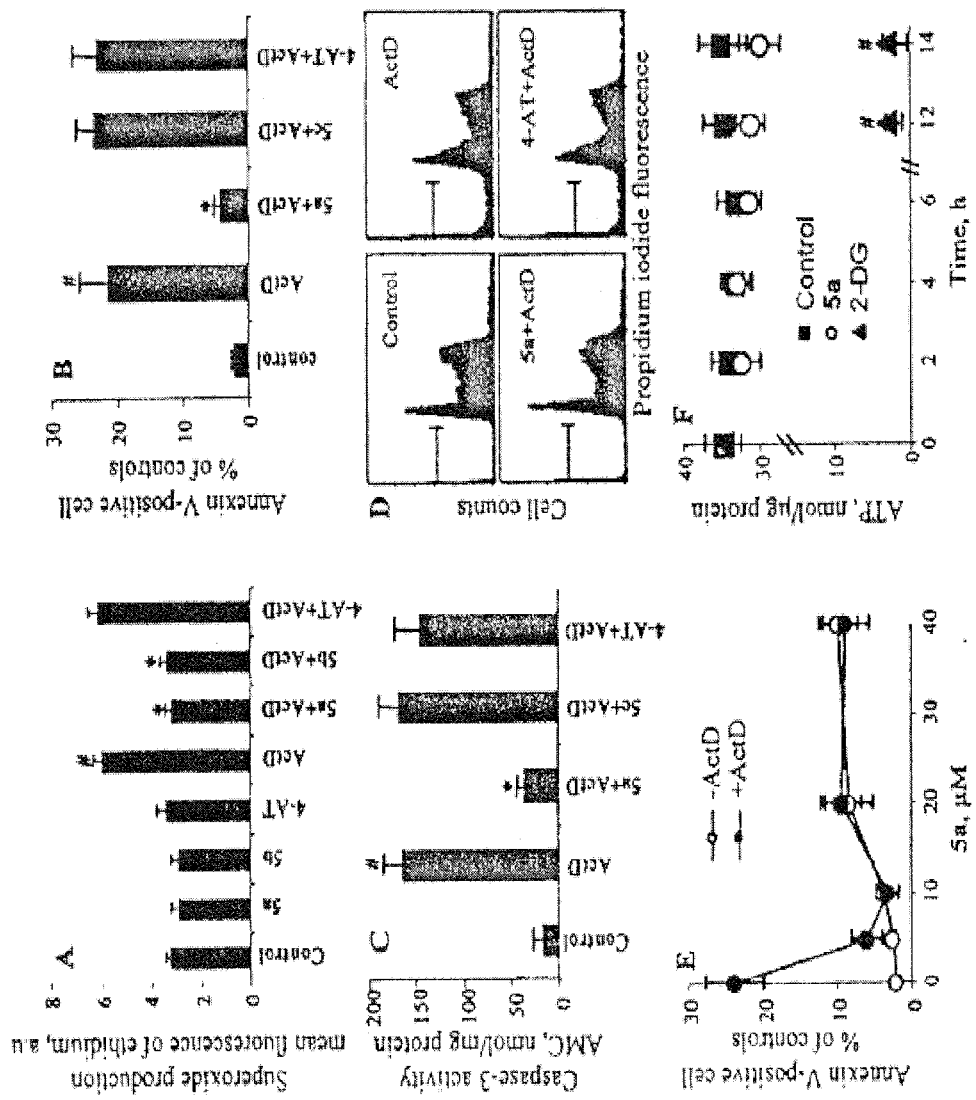
FIG. 6 shows graphical representations of the effect of nitroxide conjugates on ActD-induced apoptosis.
Figure 7A:
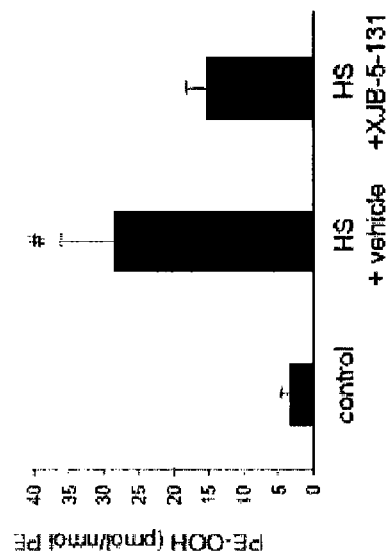
FIG. 7A is a graphical representation of the peroxidation of phosphatidylcholine ("PC").
Figure 7B:
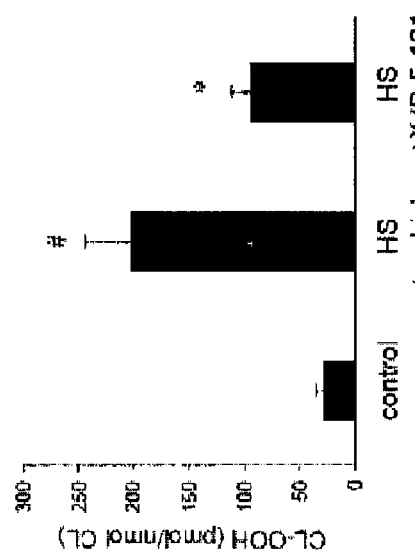
FIG. 7B is a graphical representation of peroxidation activity with respect to phosphatidylethanolamine ("PE").
Figure 7C:
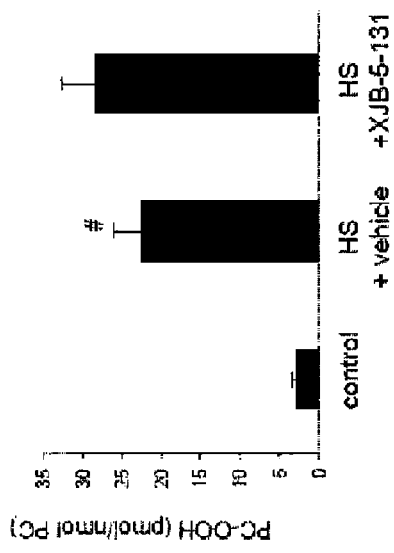
FIG. 7C is a graphical representation of peroxidation activity with respect to phosphatidylserine ("PS").
Figure 7D:
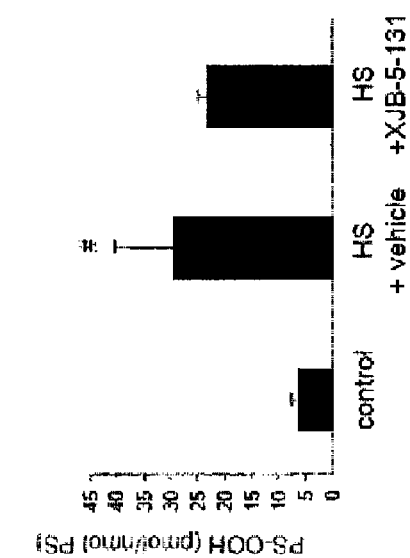
FIG. 7D is a graphical representation of peroxidation activity with respect to cardiolipin ("CL").

Anti-apoptotic effects of compounds 5a and 5b were observed at relatively low concentrations of 10 µM. Compounds 5a and 5b (FIG. 3) reduced the number of annexin V-positive cells as shown in FIG. 6B, prevented caspase-3 activation as shown in FIG. 6C, and prevented DNA fragmentation as shown in FIG. 6D. At concentrations in excess of 10 µM, both 5a and 5b were either less protective or exhibited cytotoxicity (FIG. 6E). In contrast, 4-AT afforded no protection.

In contrast, compound 5c, which does not have a complete targeting moiety, was ineffective in protecting MECs against ActD-induced apoptosis (FIGS. 6B and 6C) at low concentrations. Accordingly, the hemigramicidin peptidyl targeting sequence is essential for anti-apoptotic activity of nitroxide conjugates such as those containing TEMPO.

Finally, the reduction of compounds 5a and 5b could also cause inhibition of mitochondrial oxidative phosphorylation, so the ATP levels of MECs treated with these compounds were tested. As is known to one ordinarily skilled in the art, ATP serves as the primary energy source in biological organisms; reduction of ATP levels would greatly impair normal cell function. ATP levels in MECs in the presence or absence of 5a or 2-deoxyglucose ("2-DG") were used as a positive control (see FIG. 6F). At concentrations at which anti-apoptotic effects were maximal (~10 µM, FIG. 6E), nitroxide conjugates did not cause significant changes in the cellular ATP level. Therefore, synthetic GS-peptidyl conjugates migrate into cells and mitochondria where they are reduced without affecting the ability of the mitochondria to produce ATP.

EXAMPLE 3

In an in vivo assay, the ileum of rats was divided into a series of well-vascularized components in a manner akin to links of sausage. The lumen of each ileal compartment was filled with a 3 µL aliquot of test solution. Two of the ileal compartments were filled with vehicle alone (i.e., a solution containing at least in part the TEMPO derivative). These two components served as internal controls to account for individualistic variations in the severity of shock or the response of the mucosa to the shock.

Figure 5:
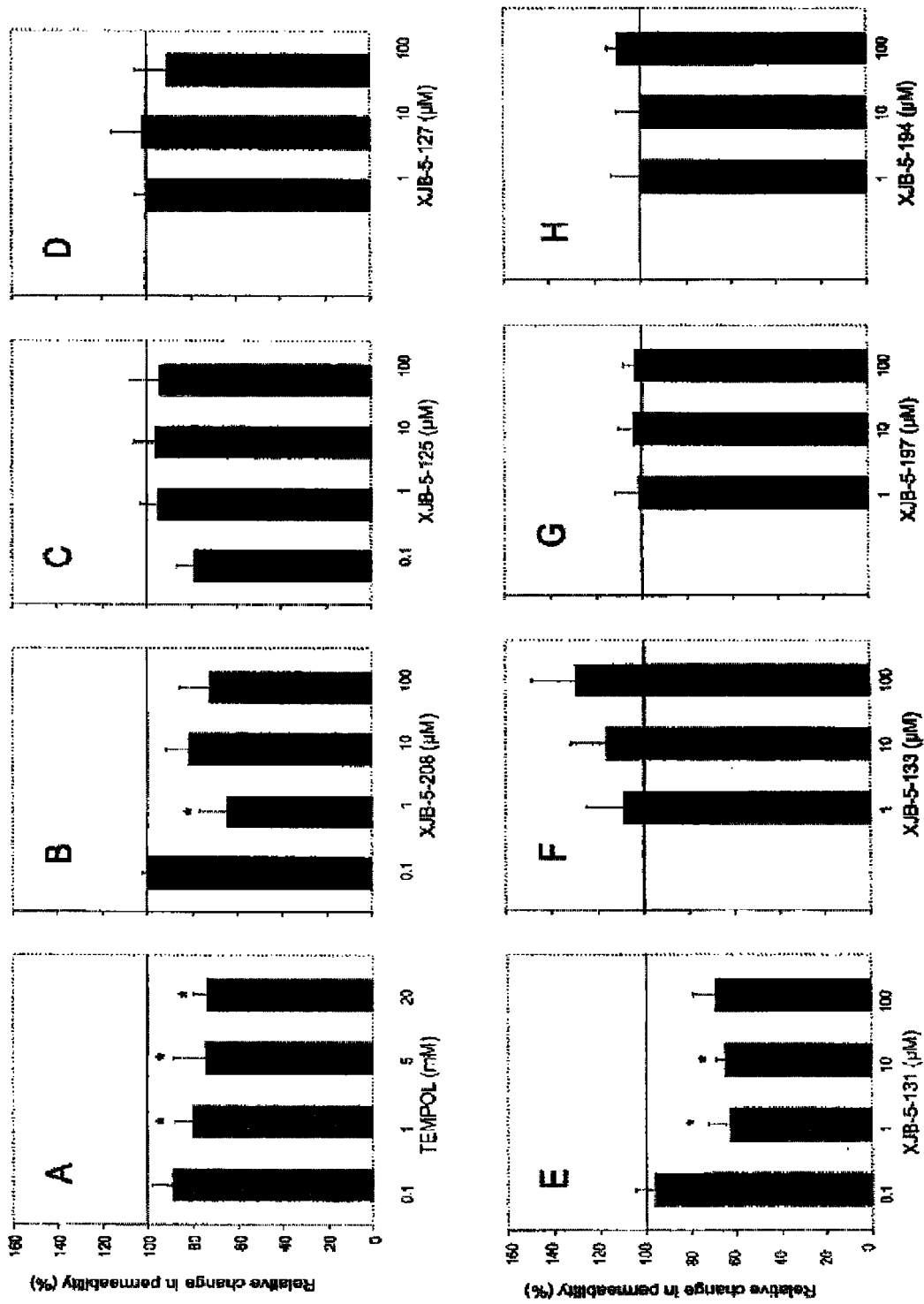
FIG. 5 shows a fluorescein isothiocyanate-dextran (FD4) read-out which reflects the effect of Gramicidin-S TEMPO conjugates on rat ileal mucosal permeability following profound hemorrhagic shock. Data are expressed as a percentage of the change permeability relative to that observed in simultaneously assayed control segments loaded during shock with normal saline solution.

Using this assay system, eight compounds were evaluated as shown in FIG. 5: TEMPOL (FIG. 5A), one dipeptidic TEMPO analog (FIG. 5B—XJB-5-208), 3 hemigramicidin-TEMPO conjugates (FIGS. 5C XJB-5-125, 5E XJB-5-131, and 5G XJB-5-197), and 3 hemigramicidin compounds that do not have the TEMPO moiety (FIGS. 5D—XJB-5-127, 5F—XJB-5-133, and 5H—XJB-5-194).

Hemorrhagic shock in rats leads to marked derangements in intestinal mucosal barrier function—in other words, the mucosal permeability of shocked intestinal segments was significantly greater than the permeability of segments from normal rats (52.3+0.5 versus 6.9+0.1 nL·min$^{-1}$·cm$^{-2}$, respectively; p<0.01), see Tuominen, E. K. J., *Phospholipid cytochrome c interaction: evidence for the extended lipid anchorage*, J. BIOL. CHEM., 277:8822-8826 (2002); also Wipf P. et al., *Mitochondria targeting of selective electron scavengers: synthesis and biological analysis of hemigramicidin-TEMPO conjugates*, J. AM. CHEM. SOC. 127:12460-12461. Accordingly, mice were subjected to 2 hours of shock (Mean Arterial Pressure ("MAP")=30 f 3 mm Hg), the gut segments were harvested and mucosal permeability to fluorescein isothiocyanate-dextran ("FD4") measured ex vivo. Data in FIG. 5 are expressed as a percentage of the change permeability relative to that observed in simultaneously assayed control segments loaded during shock with normal saline solution.

Accordingly, intraluminal TEMPOL was used as a "positive control" for gut mucosal protection assay. TEMPOL concentrations >1 mM in the gut lumen ameliorated hemorrhagic shock-induced ileal mucosal hyperpermeability (FIG. 5A). Two of the TEMPO conjugates, namely XJB-5-208 (FIG. 5B) and XJB-5-131 (FIG. 5C), also significantly ameliorated hemorrhagic shock-induced ileal mucosal hyperpermeability. The lowest effective concentration for XJB-5-208 (FIG. 5B) and XJB-5-131 (FIG. 5E) was 1 µM; i.e., both of these compounds were ~1000-fold more potent than TEMPOL. Two other compounds carrying the TEMPO payload, XJB-5-125 (FIG. 5C) and XJB-5-197 (FIG. 5G) failed to provide protection against gut barrier dysfunction induced by hemorrhage. XJB-5-133 (FIG. 5F) has the same (hemigramicidin-based) mitochondrial targeting moiety as XJB-5-131 (FIG. 5E) but lacks the TEMPO payload. It is noteworthy, therefore, that XJB-5-133 (FIG. 5F) did not afford protection from the development of ileal mucosal hyperpermeability.

Ineffective as well were the two other hemigramicidin-based compounds that also lacked the TEMPO payload, XJB-5-127 (FIG. 5D) and XJB-5-194 (FIG. 5H). Of the compounds screened, XJB-5-131 (FIG. 5E) appeared to be the most effective, reducing hemorrhagic shock-induced mucosal hyperpermeability to approximately 60% of the control value.

Based upon the results as reflected in FIGS. 5A-5H, both the TEMPO payload and the "anchoring" hemigramicidin fragment are requisite moieties that should be present in order for effective electron scavenging activity by the XJB-5-131 compound. Accordingly, it was found that XJB-5-131 ameliorates peroxidation of mitochondrial phospholipids (i.e., ROS activity) in gut mucosa from rats subject to hemorrhagic shock.

In the subsequent series of in vivo studies, the affect of intraluminal XJB-5-131 on hemorrhage-induced peroxidation of phospholipids in intestinal mucosa was examined. Isolated segments of the ileum of rats were divided into a series of well-vascularized components in a manner akin to sausage and the lumen of each ileal compartment was filled with the same volume of test solution containing either vehicle or a 10 µM solution of XJB-5-131, which was previously indicated to be the most active of the hemigramicidin-TEMPO conjugates. In a preferred embodiment, 0.3 mL of test solution filled the lumen of each ileal compartment.

After two hours of HS, samples of ileal mucosa from the gut sacs filled with the vehicle and XJB-5-131 were obtained and compared with ileal mucosa of normal MECs. All samples were assayed with caspase 3 or caspase 7 activity as well as the peroxidation of phosphatidylcholine ("PC"), phosphatidylethanolamine ("PE"), phosphatidylserine ("PS"), and cardiolipin ("CL"), summarized in FIG. 7.

As can be seen in FIGS. 7A-7D, treatment with XJB-5-131 significantly ameliorated hemorrhage-induced peroxidation of CL, the only phospholipid tested found in mitochondria. However, treatment with XJB-5-131 only had a small effect on PE peroxidation and no effect on peroxidation of PC and PS. Based upon these trends, hemorrhagic shock is associated with substantial oxidative stress even in the absence of resuscitation. Further, this data also establishes that XJB-5-131 is an effective ROS scavenger as it localizes predominantly in mitochondria and protects CL from peroxidation.

Relative to the activity measured in samples from normal animals, the activity of caspases 3 and 7 was markedly increased in vehicle-treated mucosal samples from hemorrhaged rats (FIG. 8). However, when the ileal segments were filled with XJB-5-131 solution instead of its vehicle, the level of caspase 3 and 7 activity after hemorrhagic shock was significantly decreased. Accordingly, hemorrhagic shock is associated with activation of pro-apoptotic pathways in gut mucosal cells. Moreover, the data support the view that this process is significantly ameliorated following mitochondrial treatment with XJB-5-131.

EXAMPLE 4

In another series of experiments, monolayers of enterocyte-like cells, Caco-2$_{BBc}$, were studied for physiological and pathophysiological purposes for determining intestinal barrier function. Just as with the prior Examples with respect to ROS exposure, the permeability of Caco-2$_{BBc}$ monolayers increases when the cells are incubated with the ROS, hydrogen peroxide, or menadione (a redox-cycling quinine that promotes the formation of superoxide anion radicals), see Baker, R. D. et al, *Polarized Caco-2 cells, Effect of reactive oxygen metabolites on enterocyte barrier function*, DIGESTIVE DIS. SCI. 40:510-518 (1995); also Banan, A. et al., *Activation of delta-isoform of protein kinase C is required for oxidant-induced disruption of both the microtubule cytoskeleton and permeability barrier of intestinal epithelia*, J. PHARMACOL. EXP. THER. 303:17-28 (2002).

Due to the results with respect to XJB-5-131 and its amelioration of hemorrhage-induced CL peroxidation in mucosal cells in vivo (see aforementioned Examples 1 and 2), a possible treatment using XJB-5-131 was investigated to determine if menadione-induced epithelial hyperpermeability could be ameliorated in vitro. Consistent with the prior in vivo observations, Caco-2$_{BBc}$ monolayers were incubated in the absence and in the presence of menadione, respectively. After 6 hours, incubation of Caco-2$_{BBc}$ monolayers with menadione caused a marked increase in the apical-basolateral clearance of FD4 (FIG. 9). Treatment with 10 µM XJB-5-131 provided significant protection against menadione-induced hyperpermeability.

EXAMPLE 5

As reflected by the above in vivo and in vitro studies, XJB-5-131 had significantly beneficial effects on several biochemical and physiological read-outs. Accordingly, systemic administration of XJB-5-131 was investigated with respect to whether it would prolong survival of patients subjected to profound periods of hemorrhagic shock with massive blood loss in the absence of standard resuscitation with blood and crystalloid solution. As in the above studies, rats were utilized as test patients.

A total of sixteen rats were tested in this study. Rats were treated with 2.8 ml/kg of vehicle or the same volume of XJB-5-131 solution during the final 20 min of the bleeding protocol. The total dose of XJB-5-131 infused was 2 µmol/kg. Following profound hemorrhagic shock consistent with the protocol described above for the prior studies, thirteen survived for at least 60 min and received the full dose of either XJB-5-131 solution or the vehicle, a 33:67 (v/v) mixture of DMSO and normal saline. As shown in Table 2, blood glucose, lactate and hemoglobin concentrations were similar in both groups at baseline and before and immediately after treatment. None of the between-group differences were statistically significant.

TABLE 2

| Parameter | Compound | Baseline | End of first phase of hemorrhage | End of second phase of hemorrhage |
|---|---|---|---|---|
| Blood glucose concentration (mg/dL) | Vehicle | 143 ± 5 | 255 ± 30 | 219 ± 26 |
| | XJB-5-131 | 134 ± 4 | 228 ± 24 | 201 ± 38 |
| Blood lactate concentration (mEq/L) | Vehicle | 1.8 ± 0.4 | 606 ± 0.8 | 5.9 ± 1.3 |
| | XJB-5-131 | 1.8 ± 0.2 | 5.7 ± 0.8 | 5.6 ± 1.2 |
| Blood Hb concentration (g/dL) | Vehicle | 12.7 ± 0.5 | 11.1 ± 0.3 | 9.4 ± 0.2 |
| | XJB-5-131 | 12.7 ± 0.3 | 10.7 ± 0.3 | 9.4 ± 0.3 |

Figure 10A:
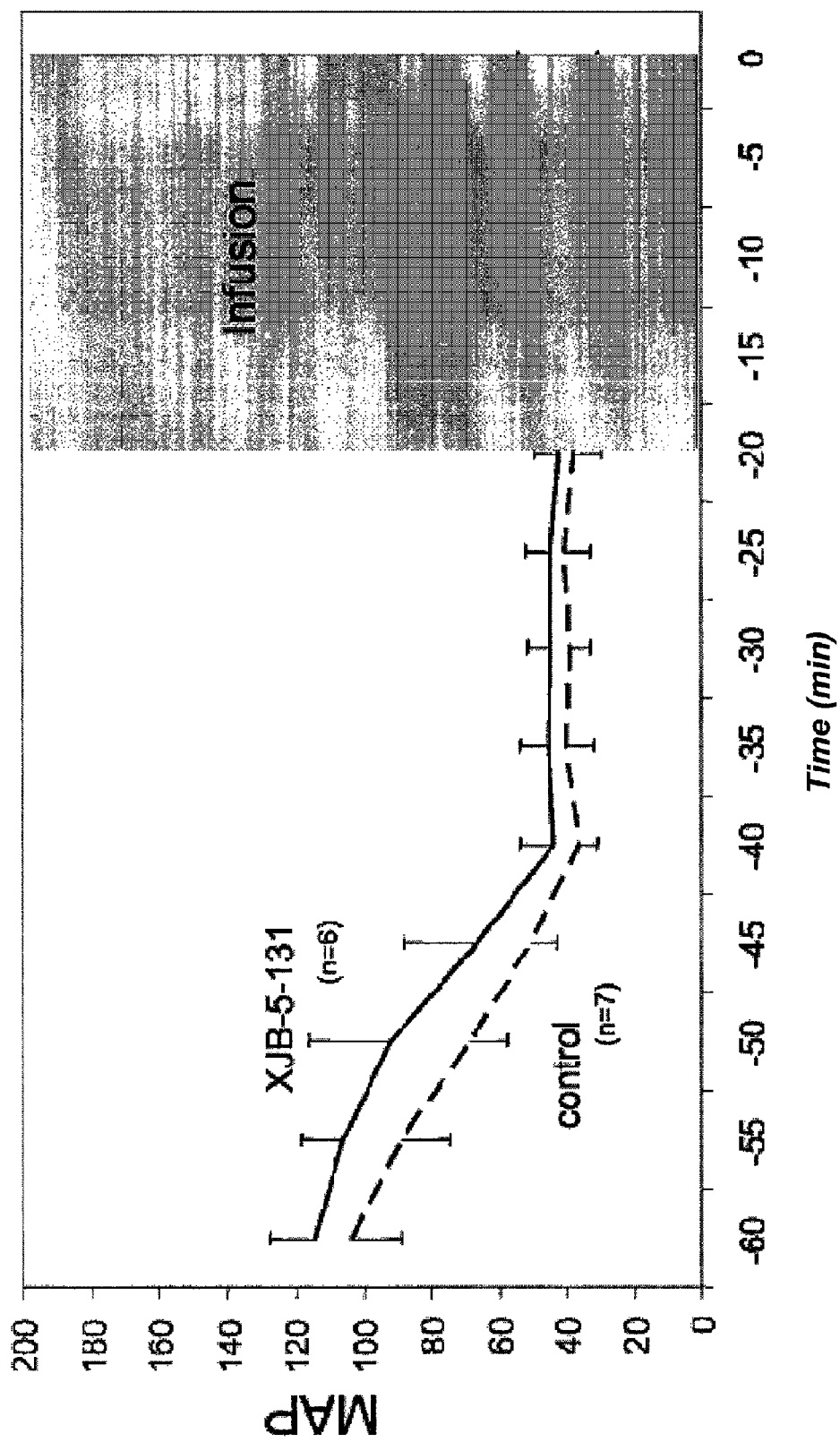
FIG. 10A is a graphical representation of the effects of intravenous treatment with XJB-5-131 on MAP (mean arterial pressure, mm Hg) of rates subjected to volume controlled hemorrhagic shock.
Figure 10B:
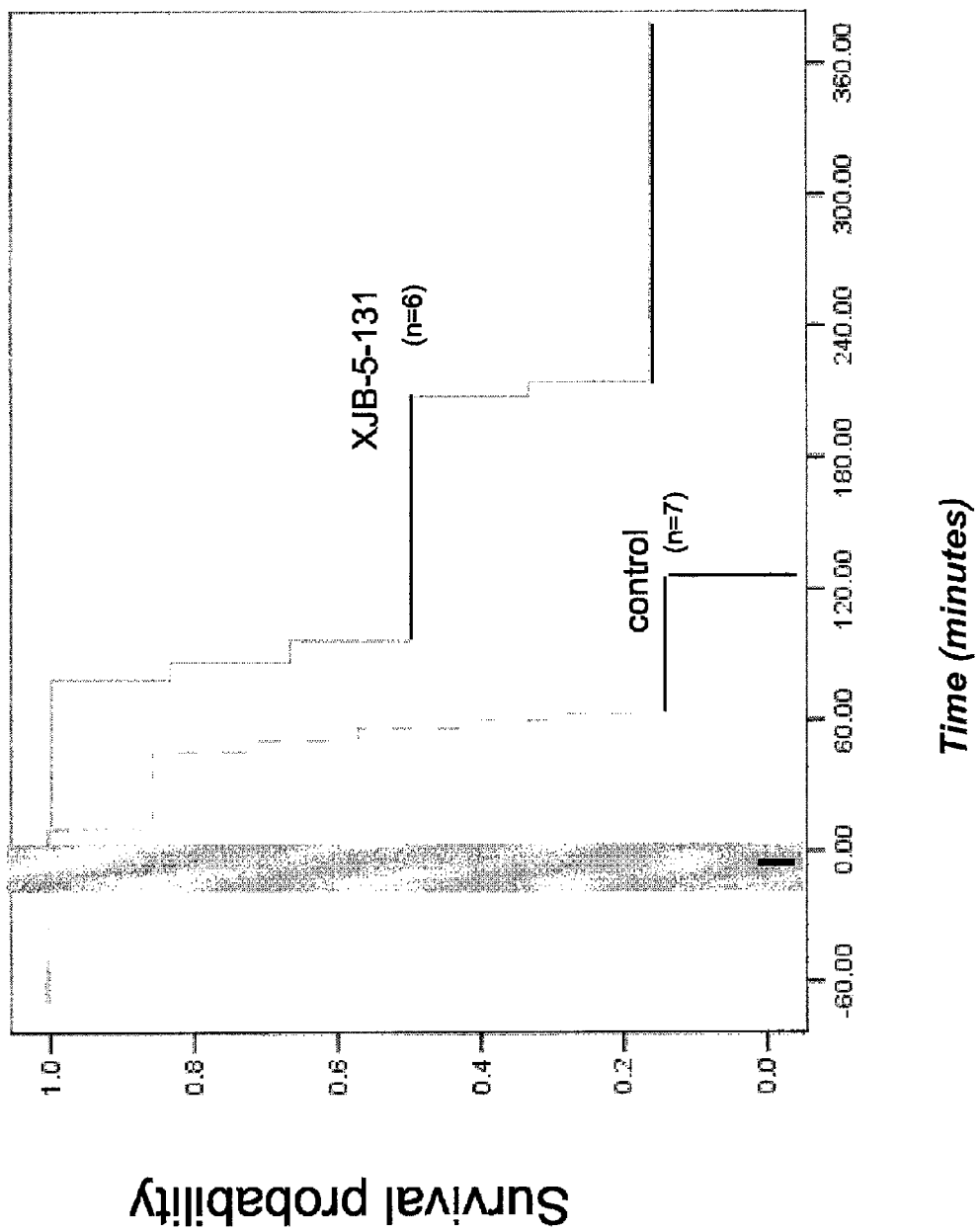
FIG. 10B is a graphical representation of the effects of intravenous treatment with XJB-5-131 on survival probability of rates subjected to volume controlled hemorrhagic shock.

Shortly after treatment was started, mean arterial pressure ("MAP") increased slightly in both groups (see FIG. 10A). In both groups, mean arterial pressure ("MAP") decreased precipitously during the first phase of the hemorrhage protocol and remained nearly constant at 40 mm Hg during the beginning of the second phase. Six of the seven animals in the vehicle-treated (control) group died within one hour of the end of the bleeding protocol and all were dead within 125 minutes (FIG. 10B). Rats treated with intravenous XJB-5-131 survived significantly longer than those treated with the vehicle. Three of the six rats survived longer than 3 hours after completion of the hemorrhage protocol; one rat survived the whole 6 hour post-bleeding observation period (FIG. 10B).

Accordingly, analysis of the XJB-5-131 studies indicate that exposure of the patient to the compound prolongs the period of time that patients can survive after losing large quantities of blood due to traumatic injuries or other catastrophes (e.g., rupture of an abdominal aortic aneurysm).

By extending the treatment window before irreversible shock develops, treatment in the field with XJB-5-131 might "buy" enough time to allow transport of more badly injured patients to locations where definitive care, including control of bleeding and resuscitation with blood products and non-sanguineous fluids, can be provided. The results using a rodent model of hemorrhagic shock also open up the possibility that drugs like XJB-5-131 might be beneficial in other conditions associated with marked tissue hypoperfusion, such as stroke and myocardial infarction.

The results presented here also support the general concept that mitochondrial targeting of ROS scavengers is a reasonable therapeutic strategy. Although previous studies have shown that treatment with TEMPOL is beneficial in rodent HS situations, a relatively large dose of the compound was required (30 mg/kg bolus+30 mg/kg per h). In contrast, treatment with a dose of XJB-5-131 that was about 300 fold smaller (~0.1 mg/kg) was clearly beneficial. The greater potency of XJB-5-131 as compared to TEMPOL presumably reflects the tendency of XJB-5-131 to localize in mitochondrial membranes, a key embodiment of the invention. As indicated above, two hemigramicidin-4-amino-TEMPO conjugates (namely XJB-5-208 and XJB-5-131, see FIG. 2) are concentrated in the mitochondria of cultures mouse embryonic cells following incubation with solutions of the compounds.

Further, the use of XJB-5-131 significantly prolonged the survival of the rats subjected to massive blood loss, even though the animals were not resuscitated with either blood or other non-sanguineous fluids and they remained profoundly hypotensive.

In light of the above, synthetic hemigramicidin peptidyl-TEMPO conjugates permeate through the cell membrane and also the mitochondrial membrane where they act as free radical scavengers for ROS such as, but not limited to, superoxide anion radicals. The conjugates are then reduced within the mitochondria by electron-transport proteins which are involved with the cellular respiration pathway, thereby coupling the decoupled ROS species. These conjugates also have the advantage, as discussed above, of being anti-apoptotic, especially in the case of compounds such as 5a and 5b.

By effectively reducing the amount of ROS species, a patient's condition, including an illness or other medical condition, may be ameliorated and, in some cases, survival may be prolonged as described in the Example IV study. Examples of such conditions, including diseases and other medical conditions, include (but are not limited to) the following medical conditions which include diseases and conditions: myocardial ischemia and reperfusion (e.g., after angioplasty and stenting for management of unstable angina or myocardial infarction), solid organ (lung liver, kidney, pancreas, intestine, heart) transplantation, hemorrhagic shock, septic shock, stroke, tissue damage due to ionizing radiation, lung injury, acute respiratory distress syndrome (ARDS), necrotizing pancreatitis, and necrotizing enterocolitis.

EXAMPLE 6

In a further embodiment, in support of the inter-changeability of cargoes of the mitochondria-targeting groups, a composition for scavenging radicals in a mitochondrial membrane comprises a radical scavenging agent or an NOS inhibitor and a membrane active peptidyl fragment having a high affinity with the mitochondrial membrane. The membrane active peptidyl fragment preferably has a property selected from the group consisting of antioxidant, radioprotective, protective, anti-apoptotic, therapeutic, ameliorative, NOS antagonist and combinations thereof. In a related embodiment, with respect to compounds with antibiotic properties, it is generally preferable to employ compounds whose mode of action includes bacterial wall targets.

In another embodiment, the membrane active compound is preferably selected from the group consisting of bacitracins, gramicidins, valinomycins, enniatins, alamethicins, beauvericin, serratomolide, sporidesmolide, tyrocidins, polymyxins, monamycins, and lissoclinum peptides.

In a related embodiment, the NOS antagonist is selected from the group consisting of XJB-5-234 (a), XJB-5-133 (b), XJB-5-241 (c), and XJB-5-127 (d), comprising AMT NOS antagonist cargos:

(a)
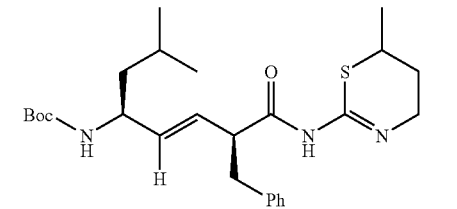

(b)
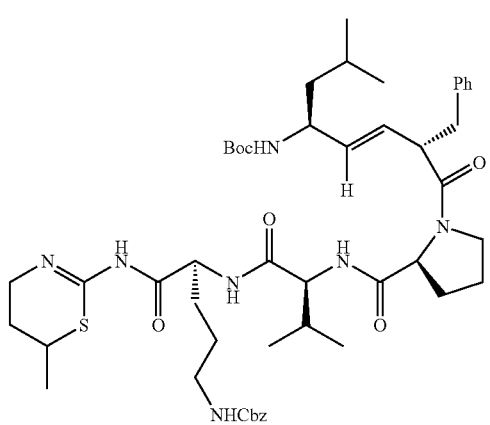

(c)
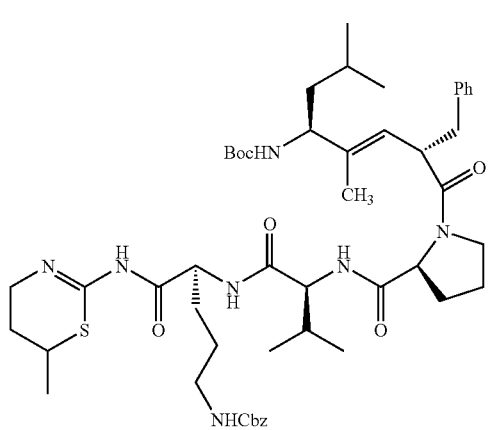

(d)
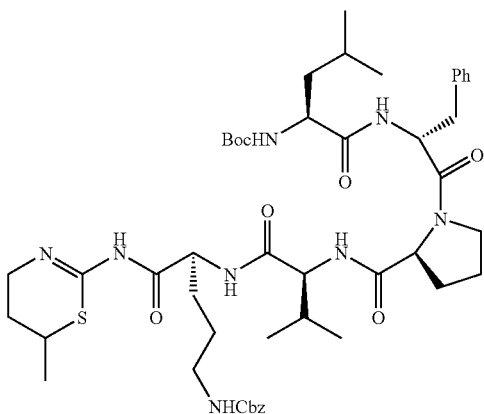

EXAMPLE 7

The following examples provide protocols for additional cargo usable in compounds described herein which serve as NOS antagonists.

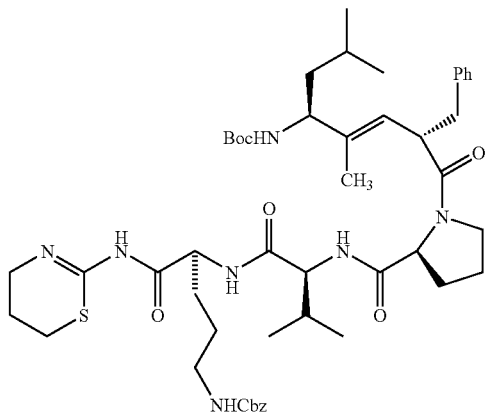

Compound (1) is Boc-Leu-ψ[(E)-C(CH$_3$)=CH]-$^D$Phe-Pro-Val-Orn(Cbz)-AMT (XJB-5-241) and was prepared according to the following protocol. A solution of 11.0 mg (13.2 μmol) of Boc-Leu-ψ[(E)-C(CH$_3$)=CH]-$^D$Phe-Pro-Val-Orn(Cbz)-OMe (2-48) in 400 μL of MeOH was treated at 0° C. with 132 μL (132 μmol) of 1 N NaOH. The reaction mixture was stirred at room temperature for 8 h, and treated with 132 μL (132 μmol) of 1 N HCl. The solution was extracted with CHCl$_3$ and the organic layer was dried (Na$_2$SO$_4$) and concentrated in vacuo to give the crude acid as a colorless form. This acid was dissolved in 2.00 mL of CHCl$_3$ and treated at room temperature with 2.1 mg (16 μmol) of HOBt, 3.0 mg (16 μmol) of EDC, 3.3 mg (20 μmol) of 2-amino-5,6-dihydro-6-methyl-4H-1,3-thiazine.HCl and 3.5 mg (27 μmol) of DMAP. The reaction mixture was stirred at room temperature for 48 h, diluted with CHCl$_3$, and washed with H$_2$O. The organic layer was dried (Na$_2$SO$_4$), concentrated in vacuo, and purified by chromatography on SiO$_2$ (1:1, hexanes/EtOAc followed by 20:1, CHCl$_3$/MeOH) to yield 11 mg (89%) of XJB-5-241 as a colorless powder. The following characterization data were obtained: LC-MS (R$_t$ 8.37 min, linear gradient 70% to 95% CH$_3$CN(H$_2$O) in 10 min, 0.4 mL/min; m/z=932.4 [M+H]$^+$, 954.3 [M+Na]$^+$) and HRMS (ESI) m/z calculated for C$_{50}$H$_{74}$N$_7$O$_8$S (M+H) 932.5320, found 932.5318.

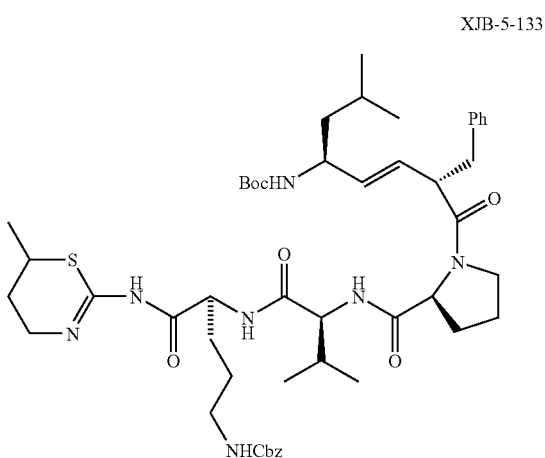

XJB-5-133

Compound (2) is Boc-Leu-ψ[(E)-CH=CH]-ᴰPhe-Pro-Val-Orn(Cbz)-AMT (XJB-5-133) and was prepared according to the following protocol. A solution of 20.0 mg (24.3 μmol) of 2-85 (XJB-5-194) in 800 μL of MeOH was treated at 0° C. with 243 μL (243 μmol) of 1 N NaOH. The reaction mixture was stirred at room temperature for 6 h, and treated with 243 μL (243 μmol) of 1 N HCl. The solution was extracted with CHCl₃ and the organic layer was dried (Na₂SO₄) and concentrated in vacuo to give the crude acid as a colorless form. This acid was dissolved in 1.00 mL of CHCl₃ and treated at room temperature with 3.9 mg (29 μmol) of HOBt, 5.6 mg (29 μmol) of EDC, 6.1 mg (37 μmol) of 2-amino-5,6-dihydro-6-methyl-4H-1,3-thiazine.HCl and 7.4 mg (61 μmol) of DMAP. The reaction mixture was stirred at room temperature for 20 h, diluted with CHCl₃, and washed with H₂O. The organic layer was dried (Na₂SO₄), concentrated in vacuo, and purified by chromatography on SiO₂ (1:1, hexanes/EtOAc followed by 20:1, CHCl₃/MeOH) and an additional preparative C₁₈ reverse phase HPLC purification was performed: 80% to 100% CH₃CN(H₂O) in 20 min, 5.0 mL/min) to afford 12.9 mg (58%) of XJB-5-133 as a colorless powder. The following characterization data were obtained: LC-MS (R$_t$ 7.89 min, linear gradient 70% to 95% CH₃CN (H₂O) in 10 min, 0.4 mL/min; m/z=918.3 [M+H]⁺, 940.3 [M+Na]⁺) and HRMS (ESI) m/z calculated for C₄₉H₇₂N₇O₈S (M+H) 918.5163, found 918.5185.

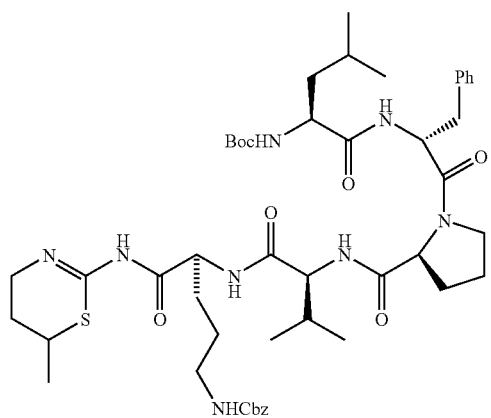

Compound (3) is Boc-Leu-ᴰPhe-Pro-Val-Orn(Cbz)-AMT (XJB-5-127) and was prepared according to the following protocol. A solution of 24.0 mg (28.7 μmol) of Boc-Leu-ᴰPhe-Pro-Val-Orn(Cbz)-OMe in 800 μL of MeOH was treated at room temperature with 287 μL (287 μmol) of 1 N NaOH. The reaction mixture was stirred at room temperature for 5 h, and treated at 0° C. with 287 μL (287 μmol) of 1 N HCl. The solution was extracted with CHCl₃ and the organic layer was dried (Na₂SO₄) and concentrated in vacuo to give the crude acid as a colorless foam. The crude acid was dissolved in 2.00 mL of CHCl₃ and treated at room temperature with 4.6 mg (34 μmol) of HOBt, 6.6 mg (34 μmol) of EDC, 5.7 mg (34 μmol) of 2-amino-5,6-dihydro-6-methyl-4H-1,3-thiazine.HCl and 8.8 mg (72.0 μmol) of DMAP. The reaction mixture was stirred at room temperature for 24 h, diluted with CHCl₃, and washed with H₂O. The organic layer was dried (Na₂SO₄), concentrated in vacuo, and purified by chromatography on SiO₂ (2:1, hexanes/EtOAc followed by 20:1, CHCl₃/MeOH) to yield 17.0 mg (63%) of XJB-5-127 as a colorless powder. The following characterization data were obtained: LC-MS (R$_t$ 6.32 min, linear gradient 70% to 95% CH₃CN(H₂O) in 10 min, 0.4 mL/min; m/z=935.3 [M+H]⁺, 957.3 [M+Na]⁺) and HRMS (ESI) m/z calculated for C₄₈H₇₁N₈O₉S (M+H) 935.5065, found 935.5044.

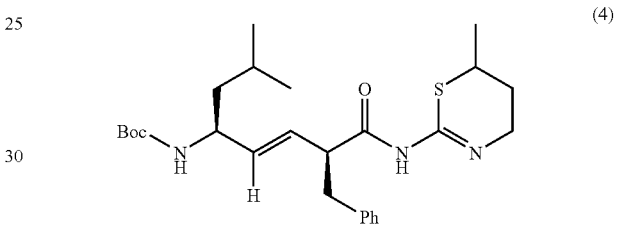

(4)

Compound (4) is Boc-Leu-ψ[(E)-CH=CH]-ᴰPhe-AMT (XJB-5-234). A solution of crude Boc-Leu-ψ[(E)-CH=CH]-ᴰPhe-OH (2-84) (30.5 μmol) in 2.00 mL of CH₂Cl₂ was treated at 0° C. with 6.1 mg (37 μmol) of 2-amino-5,6-dihydro-6-methyl-4H-1,3-thiazine.HCl, 7.0 mg (37 μmol) of EDC, 4.9 mg (37 μmol) of HOBt, and 9.3 mg (76 μmol) of DMAP. The reaction mixture was stirred at room temperature overnight, concentrated in vacuo, and purified by chromatography on SiO₂ (2:1, CH₂Cl₂/EtOAc) to yield 9.1 mg (63%) of XJB-5-234 as a colorless foam. The following characterization data were obtained: LC-MS (R$_t$ 8.42 min, linear gradient 70% to 95% CH₃CN(H₂O) in 10 min, 0.4 mL/min; m/z=474.5 [M+H]⁺) and HRMS (ESI) m/z calculated for C₂₆H₄₀N₃O₃S (M+H) 474.2790, found 474.2781.

(5)

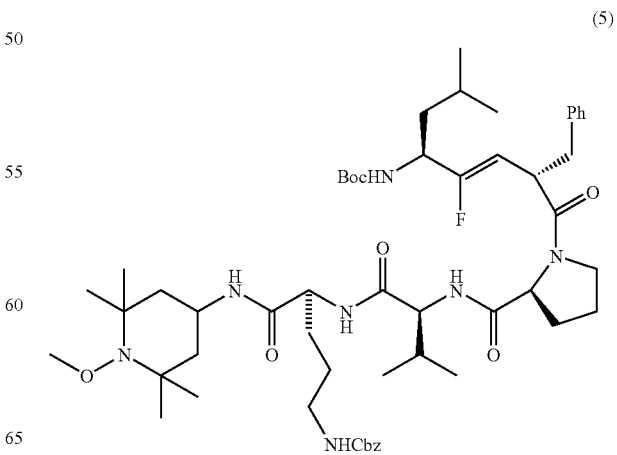

Compound (5) is Boc-Leu-ψ[(Z)-CF=CH]-DPhe-Pro-Val-Orn(Cbz)-TEMPO (XJB-7-53). A solution of 3.4 mg (4.1 µmol) of Boc-Leu-ψ[(Z)-CF=CH]-DPhe-Pro-Val-Orn(Cbz)-OMe XJB-5-66) in 400 µL of MeOH was treated at 0° C. with 41 µL (41 µmol) of 1 N NaOH. The reaction mixture was stirred at room temperature for 12 h, and treated with 41 µL (41 µmol) of 1 N HCl. The solution was extracted with CHCl$_3$ and the organic layer was dried (Na$_2$SO$_4$) and concentrated in vacuo to give the crude acid as a colorless form. This acid was dissolved in 400 µL of CHCl$_3$ and treated at room temperature with 0.7 mg (5 µmol) of HOBt, 0.9 mg (5 µmol) of EDC, 0.5 mg (4 µmol) of 4-amino-TEMPO and 1.1 mg (6 µmol) of DMAP. The reaction mixture was stirred at room temperature for 12 h, diluted with CHCl$_3$, and washed with H$_2$O. The organic layer was dried (Na$_2$SO$_4$), concentrated in vacuo, and purified by chromatography on SiO$_2$ (1:1, hexanes/EtOAc followed by 20:1, CHCl$_3$/MeOH) to yield 3.6 mg (91%) of XJB-7-53 as a colorless powder. The following characterization data were obtained: LC-MS (R$_t$ 8.45 min, linear gradient 70% to 95% CH$_3$CN(H$_2$O) in 10 min, 0.4 mL/min; m/z=977.5 [M+H]$^+$, 999.5 [M+Na]$^+$) and HRMS (ESI) m/z calculated for C$_{53}$H$_{79}$FN$_7$O$_9$Na (M+Na) 999.5821.

(6)

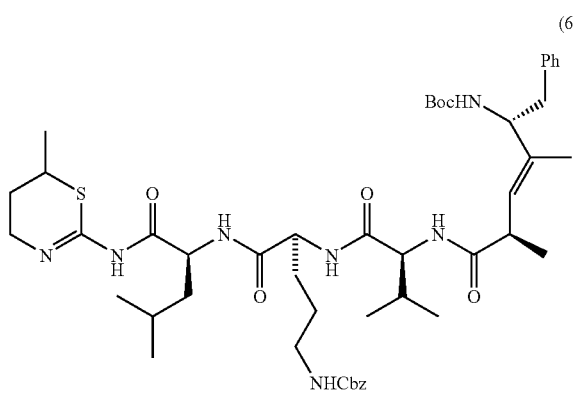

Compound (6) is Boc-DPhe-ψ[(E)-C(CH$_3$)=CH]-Ala-Val-Orn(Cbz)-Leu-AMT (XJB-7-42) and was prepared according to the following protocol. A solution of 4.5 mg (5.6 µmol) of Boc-DPhe-ψ[(E)-C(CH$_3$)=CH]-Ala-Val-Orn(Cbz)-Leu-OMe (2-119) in 0.35 mL of MeOH was treated at 0° C. with 56 µL (56 µmol) of 1 N NaOH. The reaction mixture was stirred at room temperature for 12 h, and treated with 56 µL (56 µmol) of 1 N HCl. The solution was extracted with CHCl$_3$ and the organic layer was dried (Na$_2$SO$_4$) and concentrated in vacuo to give the crude acid as a colorless form. This acid was dissolved in 0.80 mL of CHCl$_3$ and treated at room temperature with 0.9 mg (6.7 µmol) of HOBt, 1.3 mg (6.7 µmol) of EDC, 1.4 mg (8.4 µmol) of 2-amino-5,6-dihydro-6-methyl-4H-1,3-thiazine.HCl and 1.7 mg (14 µmol) of DMAP. The reaction mixture was stirred at room temperature for 36 h, concentrated in vacuo, and purified by chromatography on SiO$_2$ (20:1, CHCl$_3$/MeOH) to yield 5.0 mg (99%) of XJB-7-42 as a colorless foam. The following characterization data were obtained: LC-MS (R$_t$ 6.61 min, linear gradient 70% to 95% CH$_3$CN(H$_2$O) in 10 min, 0.4 mL/min; m/z=907.3 [M+H]$^+$, 929.4 [M+Na]$^+$) and HRMS (ESI) m/z calculated for C$_{48}$H$_{72}$N$_7$O$_8$S (M+H) 906.5163, found 906.5190.

(7)

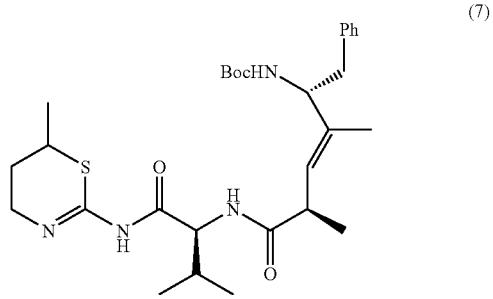

Compound (7) is Boc-DPhe-ψL[(E)-C(CH$_3$)=CH]-Ala-Val-AMT (XJB-7-43). A solution of 14.3 µmol of crude Boc-DPhe-ψ[(E)-C(CH$_3$)=CH]-Ala-Val-OMe (2-111) in 1.00 mL of CHCl$_3$ was treated at room temperature with 2.3 mg (17 µmol) of HOBt, 3.3 mg (17 µmol) of EDC, 3.6 mg (22 µmol) of 2-amino-5,6-dihydro-6-methyl-4H-1,3-thiazine.HCl and 4.4 mg (36 µmol) of DMAP. The reaction mixture was stirred at room temperature for 36 h, concentrated in vacuo, and purified by chromatography on SiO$_2$ (20:1, CHCl$_3$/MeOH) to yield 7.5 mg (96%) of XJB-7-43 as a colorless foam. The following characterization data were obtained: LC-MS (R$_t$ 5.41 min, linear gradient 70% to 95% CH$_3$CN(H$_2$O) in 10 min, 0.4 mL/min; m/z=545.3 [M+H]$^+$, 567.3 [M+Na]$^+$) and HRMS (ESI) m/z calculated for C$_{29}$H$_{44}$N$_4$O$_4$S (M+Na) 567.2981, found 567.2971.

Among the preferred radical scavenging agents are a material selected from the group consisting of a ubiquinone analog, a ubiquinone analog fragment moiety, a ubiquinone analog fragment moiety lacking a hydrophilic tail, a superoxide dismutase mimetic, a superoxide dismutase biomimetic or a salen-manganese compound.

As is known to one ordinarily skilled in the art, ionizing radiation activates a mitochondrial nitric oxide synthase ("mtNOS"), leading to inhibition of the respiratory chain, generation of excess superoxide radicals, peroxynitrite production and nitrosative damage. The damage done by ionizing radiation is believed to be alleviated [See Kanai, A. J. et al., Am J. Physiol. 383: F1304-F1312 (2002); and Kanai, A. J. et al., Am J. Physiol. 286: H13-H21 (2004)]. The composition of this embodiment is characterized by the property of inhibiting mtNOS, thereby resisting generation of excess superoxide radicals, peroxynitrite and nitrosative damage.

Protection again irradiation damage using systemic drug delivery can result in unwanted side effects. One approach to limit or prevent these adverse side effects is to target drug delivery to the mitochondria using a peptide carrier strategy.

In one embodiment, a potent NOS inhibitor, the non-arginine analog of 2-amino-6-methyl-thiazine ("AMT"), was selected as a cargo. Irradiation of the ureopithelium results in increased production of superoxide and nitric oxide ("NO"), mouse bladders were instilled with AMT or 4-amino-TEMPO to determine if inhibition of NO or scavenging free radicals is more radioprotective.

An unconjugated and conjugated NOS antagonist, (AMT, 100 µM) and an unconjugated and conjugated nitroxide derivative (4-amino-TEMPO, 100 µM) were incubated for two hours at 37° C. with 32D c13 hemopoietic cells.

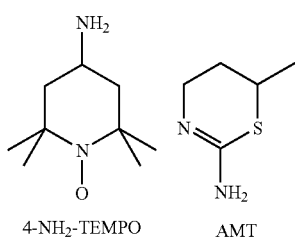

4-NH₂-TEMPO   AMT

Following incubation, the cells were lysed and the mitochondria isolated for a mass spectrometry analysis where compounds isolated from mitochondria were identified as Na+ adducts. The resulting spectra (not shown) demonstrate that 4-amino-TEMPO only permeate the mitochondrial membrane with the assistance of the attached GS-derived targeting sequence. Further spectra (not shown) indicate that unconjugated AMT do not enter the mitochondria membrane in substantial quantities. Thus, the targeting peptides successfully direct a NOS antagonist and a nitroxide to the mitochondria.

Further physiological studies were conducted to determine the effects of peptide-targeted AMT and 4-amino-TEMPO on NO and peroxynitrite production in irradiated uroepithelial cells. The cells were cultured in an 8-well slide chamber for 3 days and then microsensor measurements were taken 24 hours after irradiation.

In untreated irradiated cells and cells treated with unconjugated 4-amino-TEMPO (100 µM) or unconjugated AMT (10 µM), capsaicin evoked NO production and resulted in the formation of comparable amount of peroxynitrite. In cells treated with high-dose conjugated 4-amino-TEMPO (100 µM), peroxynitrite production was decreased by approximately 4-fold. In non-radiated cells or cells treated with conjugated AMT (10 µM), NO induced peroxynitrite formation was nearly completely inhibited. This suggested that peptides conjugates couple or covalently link with membrane impermeant 4-amino-TEMPO or AMT and facilitate the transport of 4-amino-TEMPO across the mitochondrial membrane. Furthermore, this data suggests that the peptide conjugates do not interfere with the NOS inhibitory activity of AMT or the free radical scavenging activity of 4-amino-TEMPO and that AMT is a more effective radioprotectant [Kanai, A. J. et al., Mitochondrial Targeting of Radioprotectants Using Peptidyl Conjugates, ORGANIC AND BIOMOLECULAR CHEMISTRY (in press)].

Quantitative mass spectrometry studies were used to compare the effectiveness of several AMT peptide conjugates in permeating the mitochondrial membrane, specifically XJB-5-234, XJB-5-133, XJB-5-241, and XJB-5-127. The fmole/10 µM mitochondrial protein ratio provides a relative quantification of conjugate concentration at the target site. Table 3 indicates that the most efficacious conjugate was compound XJB-5-241.

TABLE 3

| Compound | fmole/10 µM mitochondrial protein |
|---|---|
| XJB-5-234 | 1.45 |
| XJB-5-133 | 89.8 |
| XJB-5-241 | 103.3 |
| XJB-5-127 | 50.8 |

The trisubstituted (E)-alkene moiety embedded in XJB-5-241 has a stronger conformational effect that the less biologically active disubstituted (E)-alkene XJB-5-133 or the GS peptidyl fragment XJB-5-127, see Wipf P. et al., *Methyl-and (Triluoromethyl)alkene Peptide Isosteres: Synthesis and Evaluation of Their Potential as β-Turn Promoters and Peptide Mimetics* J ORG. CHEM. 63:6088-6089 (1998); also Wipf P. et al., *Imine Additions of Internal Alkynes for the Synthesis of Trisubstituted (E)-Alkene and Cyclopropane Peptide Isosteres* ADV. SYNTH. CAT. 347:1605-1613 (2005). The data indicates that a defined secondary structure and an appropriate conformational preorganization is important in accomplishing mitochondrial permeation of compounds that reduce nitrosative and oxidative effects.

The presence of a non-hydrolyzable alkene isostere functions in place of labile peptide bonds and is significant for a prolonged mechanism of action. The relatively rigid (E)-alkenes (ψL[(E)-C(R)=CH]) represent useful, conformationally preorganized structural mimetics and have been used as surrogates of hydrolytically labile amide bonds in a number of enzyme inhibitors. The primary objective of this strategy is the accurate mimicry of the geometry of the peptide bond; however, (E)-alkenes also modulate the physicochemical properties, solubility, and lipophilicity, number of hydrogen donors and acceptors, etc, of the parent structures, and therefore generally have a different metabolic fate than simple peptides.

A targeted delivery strategy employed in this invention is advantageous since some neuronal NOS (nNOS) antagonists and most antioxidants, including nitroxide derivatives, are poorly cell-permeable and require therapeutically effective concentrations greater than 100 µM if used without a conjugate.

The method related to this embodiment of the invention delivers a composition to mitochondria comprising transporting to said mitochondria a desired cargo which may, for example, be (a) a radical scavenging agent by use of a membrane active peptidyl fragment preferably having has a β-turn motif having a high affinity for the mitochondrial membrane or (b) a nitric oxide synthase antagonist bonded to the membrane active peptidyl fragment.

EXAMPLE 8

Figure 11A:
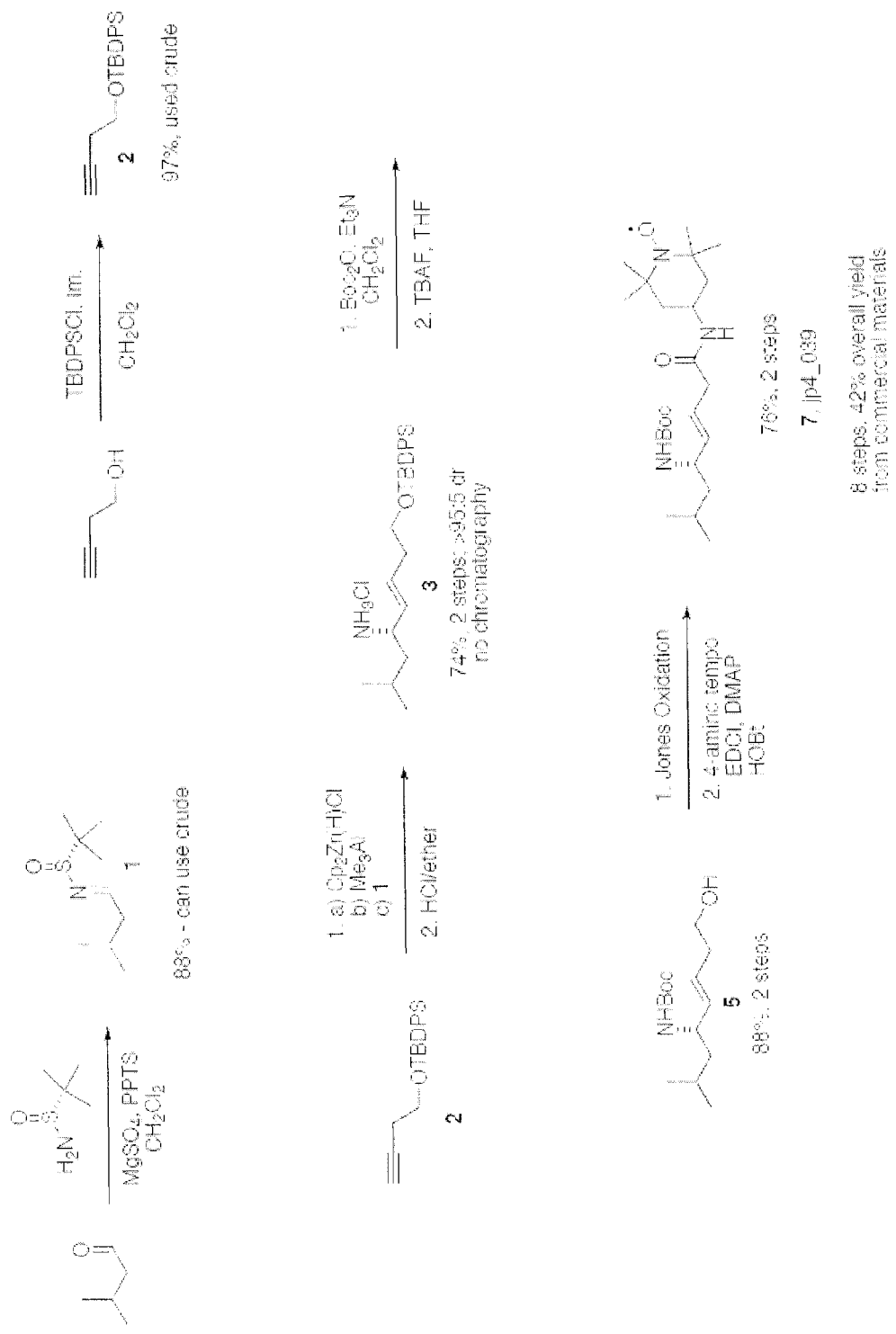
FIG. 11A is a schematic of a synthesis protocol for JP4-039.

Synthesis of JP4-039 (See FIG. 11)

Synthesis of JP4-039 was accomplished according to the following.

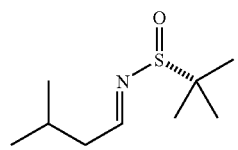

1

(R,E)-2-Methyl-N-(3-methylbutylidene)propane-2-sulfinamide (1) (Staas, D. D.; Savage, K. L.; Homnick, C. F.; Tsou, N.; Ball, R. G. *J. Org. Chem.*, 2002, 67, 8276)—To a solution of isovaleraldehyde (3-Methylbutyraldehyde, 5.41 mL, 48.5 mmol) in $CH_2Cl_2$ (250 mL) was added (R)-2-methylpropane-2-sulfinamide (5.00 g, 40.4 mmol), $MgSO_4$ (5.0 eq, 24.3 g, 202 mmol) and PPTS (10 mol %, 1.05 g, 4.04 mol) and the resulting suspension was stirred at RT (room temperature, approximately 25° C.) for 24 h. The reaction was filtered through a pad of Celite® and the crude residue was purified by chromatography on $SiO_2$ (3:7, EtOAc:hexanes) to yield 6.75 g (88%) as a colorless oil. $^1$H NMR δ 8.07 (t, 1 H, J=5.2 Hz), 2.47-2.38 (m, 2 H), 2.18-1.90 (m, 1 H), 1.21 (s, 9 H), 1.00 (d, 6 H, J=6.7 Hz). As an alternative, filtration through a pad of SiO$_2$ provides crude imine that functions equally well in subsequent reactions.

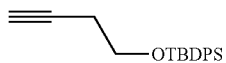

(But-3-ynyloxy)(tert-butyl)diphenylsilane (2) (Nicolaou, K. C. et al. *J. Am. Chem. Soc.* 2006, 128, 4460)—To a solution of 3-butyn-1-ol (5.00 g, 71.3 mmol) in CH$_2$Cl$_2$ (400 mL) was added imidazole (5.40 g, 78.5 mmol) and TBDPSCl ((tert-butyl)diphenylsilane chloride) (22.0 g, 78.5 mmol) and the reaction was stirred at RT for 22 h. The reaction was filtered through a pad a SiO$_2$, the RT for 14 h.The reaction was quenched with sat.aq. NH$_4$Cl, the organic layers seperated, dried (MgSO$_4$), filtered and concentrated.The crude residue was carried onto the next step without further purification.

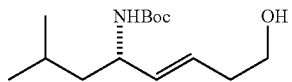

(S,E)-tert-Butyl 8-hydroxy-2-methyloct-5-en-4-ylcarbamate (5)—To a solution of crude (4) (12.0 g, 24.3 mmol) in THF (200 mL) at 0° C. was added TBAF (1.0 M in THF, 1.25 eq, 30.4 mL, 30.4 mmol) and the reaction was warmed to RT and stirred for 2 h. The reaction was quenched with sat. aq. NH$_4$Cl, organic layer washed with brine, dried (MgSO$_4$), filtered and concentrated. The crude residue was purified by chromatography on SiO$_2$ (3:7, EtOAc:hexanes) to yield 5.51 g (88%, 2 steps) as a colorless oil. [α]$_D$ −12.7 (c 1.0, CH$_2$Cl$_2$); $^1$H NMR δ 5.56 (dt, 1 H, J=15.3, 6.9 Hz), 5.41 (dd, 1 H, J=15.4, 6.4 Hz), 4.41 (bs, 1 H), 4.06 (bm, 1 H), 3.65 (appbq, 2 H, J=5.7 Hz), 2.29 (q, 2 H, J=6.3 Hz), 1.76 (bs, 1 H), 1.68 (m, 1 H), 1.44 (s, 9 H), 1.33 (m, 2 H), 0.92 (m, 6 H); $^{13}$C NMR δ 155.4, 134.3, 126.9, 79.2, 61.5, 50.9, 44.5, 35.6, 28.3, 24.6, 22.5; EIMS m/z 257 ([M]$^+$, 10), 227 (55), 171 (65); HRMS (EI) m/z calcd for C$_{14}$H$_{27}$NO$_3$ 257.1991, found 257.1994.

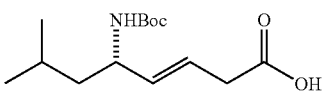

(S,E)-5-(tert-Butoxycarbonylamino)-7-methyloct-3-enoic acid (6)—To a solution of (5) (1.00 g, 3.89 mmol) in acetone (40 mL) at 0° C. was added a freshly prepared solution of Jones Reagent (2.5 M, 3.89 mL, 9.71 mmol) and the reaction was stirred at 0° C. for 1 h. The dark solution was extracted with Et$_2$O (3×50 mL), the organic layers washed with water (2×75 mL), brine (1×50 mL), dried (Na$_2$SO$_4$), filtered and concentrated to yield 990 mg (94% crude) of acid (6) as a yellow oil that was used without further purification.

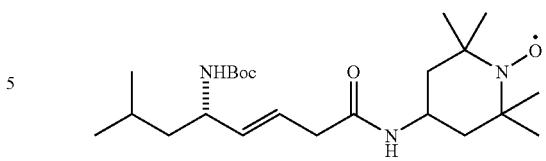

TEMPO-4-yl-(S,E)-5-(tert-butoxycarbonylamino)-7-methyloct-3-enamide (7)—To a solution of (6) (678 mg, 2.50 mmol, crude) in CH$_2$Cl$_2$ (35 mL) at 0° C. was added 4-amino tempo (1.5 eq, 662 mg, 3.75 mmol), EDCI (1.2 eq, 575 mg, 3.00 mmol), DMAP (1.1 eq, 339 mg, 2.75 mmol) and HOBt-hydrate (1.1 eq, 377 mg, 2.75 mmol) and the resulting orange solution was stirred at RT for 14 h. The reaction was diluted with CH$_2$Cl$_2$, washed with sat. aq. NH$_4$Cl and the organic layer dried (Na$_2$SO$_4$), filtered and concentrated. The crude residue was purified by chromatography on SiO$_2$ (1:1 to 2:1, EtOAc/hexanes) to yield 857 mg (76%, 2 steps) as a peach colored solid. mp 61° C. (softening point: 51° C.); [α]$_D^{23}$ +35.6 (c 0.5, DCM); ESIMS m/z 365 (40), 391 (50), 447 ([M+Na]$^+$, 100), 257 (20); HRMS (ESI) m/z calcd for C$_{23}$H$_{42}$N$_3$O$_4$Na 447.3073, found 447.3109.

Figure 11B:
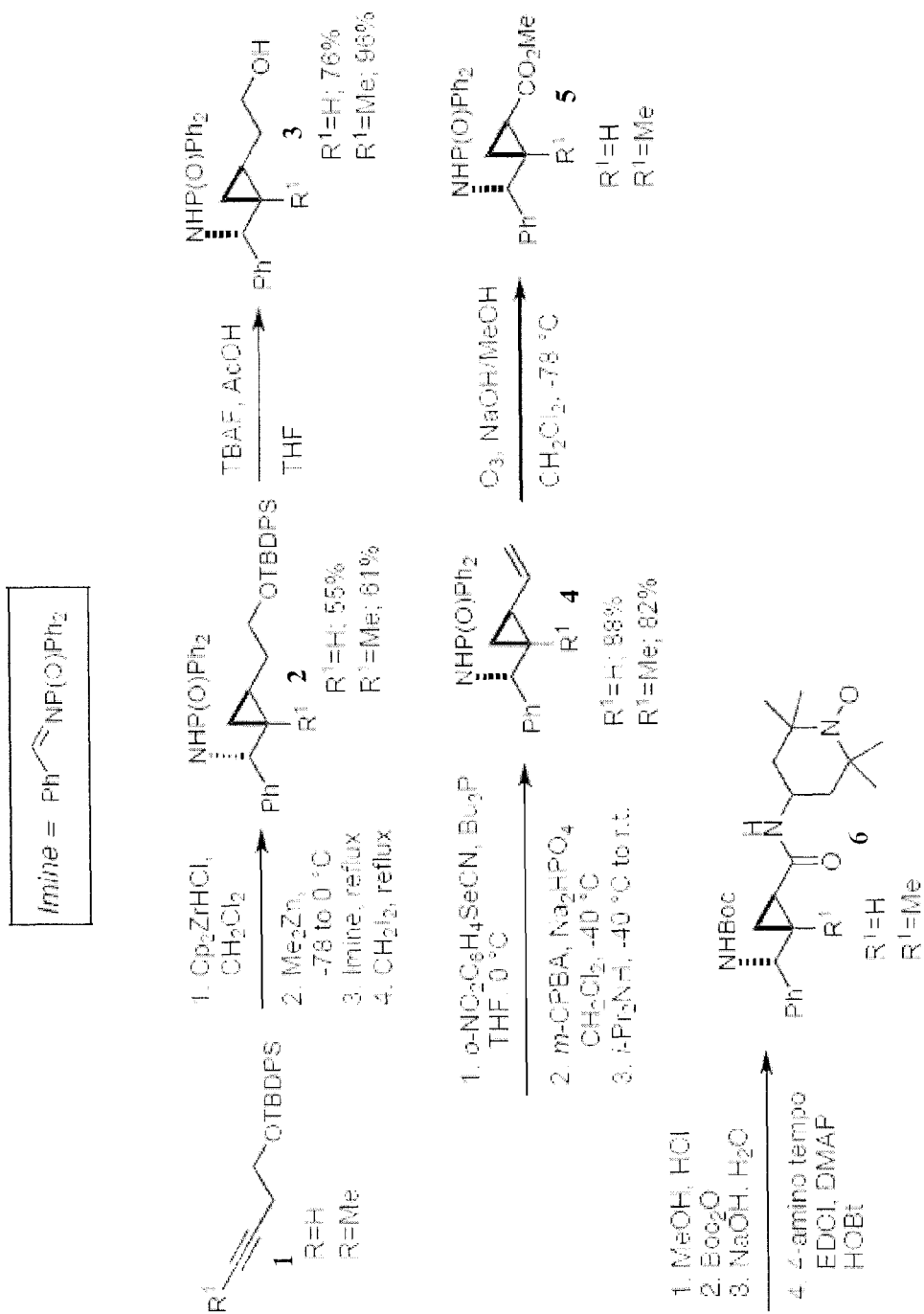
FIG. 11B provides a synthesis route for a compound of Formula 4, below.

The compounds shown as Formula 4, above can be synthesized as shown in FIG. 11B. Briefly, synthesis was accomplished as follows: To a solution of compound (1) in CH$_2$Cl$_2$ was added zirconocene hydrochloride, followed by addition of Me$_2$Zn, then a solution of N-diphenylphosphoryl-1-phenylmethanimine (Imine). The reaction mixture was refluxed, filtered, washed, and dried to afford (2). Cleavage of the TBDPS protecting group was achieved by treating (2) with TBAF, which resulted in the formation of (3). The terminal alcohol (3) was dehydrated to alkene (4), which was further treated by ozonolysis to afford ester (5). Protocols similar to that given for the synthesis of JP4-039, above, were used to acylate the amino group with the Boc protecting group and to react the terminal carboxylic acid with 4-amino-TEMPO to afford (6).

EXAMPLE 9

A mitochondria-targeted nitroxide/hemigramicidin S conjugate protects mouse embryonic cells against gamma irradiation (see, Jiang, J, et al., *Int. J. Radiation Oncology Biol. Phys.*, Vol. 70, No. 3, pp. 816-825, 2008)

EPR-based analysis of integration and distribution of nitroxides. To compare the integration efficiency, mouse embryonic cells (1×10$^7$/mL) were incubated with 10 μM nitroxides for 10 min. ESR spectra of nitroxide radicals in the incubation medium, cell suspension or mitochondrial suspension were recorded after mixing with acetonitrile (1:1 v/v) after 5-min incubation with 2 mM K$_3$Fe(CN)$_6$ using JEOL-RE1X EPR spectrometer under the following conditions: 3350 G center field; 25 G scan range; 0.79 G field modulation, 20 mW microwave power; 0.1 s time constant; 4 min scan time. Integration efficiency was calculated as (E$_{initial}$−E$_{medium}$)/E$_{initial}$×100%. Mitochondria were isolated using a mitochondria isolation kit (Pierce, Rockford, Ill.) according to the manufacturer's instruction. Amounts of nitroxide radicals integrated into mitochondria were normalized to the content of cytochrome c oxidase subunit IV.

Superoxide generation. Oxidation-dependent fluorogenic dye, DHE was used to evaluate intracellular production of superoxide radicals. DHE is cell permeable and, in the presence of superoxide, is oxidized to fluorescent ethidium which intercalates into DNA. Briefly, cells were treated with 5 μM DHE for 30 min at the end of incubation. Cells were then collected by trypsinization and resuspended in PBS. The fluorescence of ethidium was measured using a FACScan flow cytometer (Becton-Dickinson, Rutherford, N.J.) supplied with the CellQuest software. Mean fluorescence intensity from 10,000 cells was acquired using a $585/42$ nm bandpass filter.

CL oxidation. CL hydroperoxides were determined by fluorescence HPLC of products formed in MP-11-catalyzed reaction with a fluorogenic substrate, Amplex Red. Oxidized phospholipids were hydrolyzed by pancreatic phospholipase $A_2$ (2 U/ml) in 25 mM phosphate buffer containing 1 mM $CaCl_2$, 0.5 mM EDTA and 0.5 mM SDS (pH 8.0 at RT for 30 min). After that Amplex Red and MP-11 were added and samples were incubated for 40 min at 4° C. Shimadzu LC-100AT vp HPLC system equipped with fluorescence detector (RF-10Ax1, Ex/Em=560/590 nm) and autosampler (SIL-10AD vp) were used for the analysis of products separated by HPLC (Eclipse XDB-C18 column, 5 μm, 150×4.6 mm). Mobile phase was composed of $NaH_2PO_4$ (25 mM, pH 7.0)/methanol (60:40 v/v).

Phosphatidylserine (PS) externalization. Externalization of PS was analyzed by flow cytometry using annexin-V kit. Briefly, harvested cells were stained with annexin-V-FITC and PI for 5 min in dark prior to flow cytometry analysis. Ten thousand events were collected on a FACScan flow cytometer (Becton-Dickinson) supplied with CellQuest software.

Gamma-irradiation dose survival curves of mouse embryonic cells. Cells were plated in 35-mm Petri dishes with 2 ml culture medium at a density between 100 and 1000 cells per dish. Cells were treated with GS-nitroxide (XJB-5-125) either before (10-min) or after (1-h) γ-irradiation. XJB-5-125 was removed from the medium 4-h post-irradiation. Colonies were fixed and stained with 0.25% crystal violet and 10% formalin (35% v/v) in 80% methanol for 30 min after a 9-day incubation period, and those of ≧50 cells were counted as survivors. The surviving fraction was calculated as the plating efficiency of the samples relative to that of the control.

Figure 12:
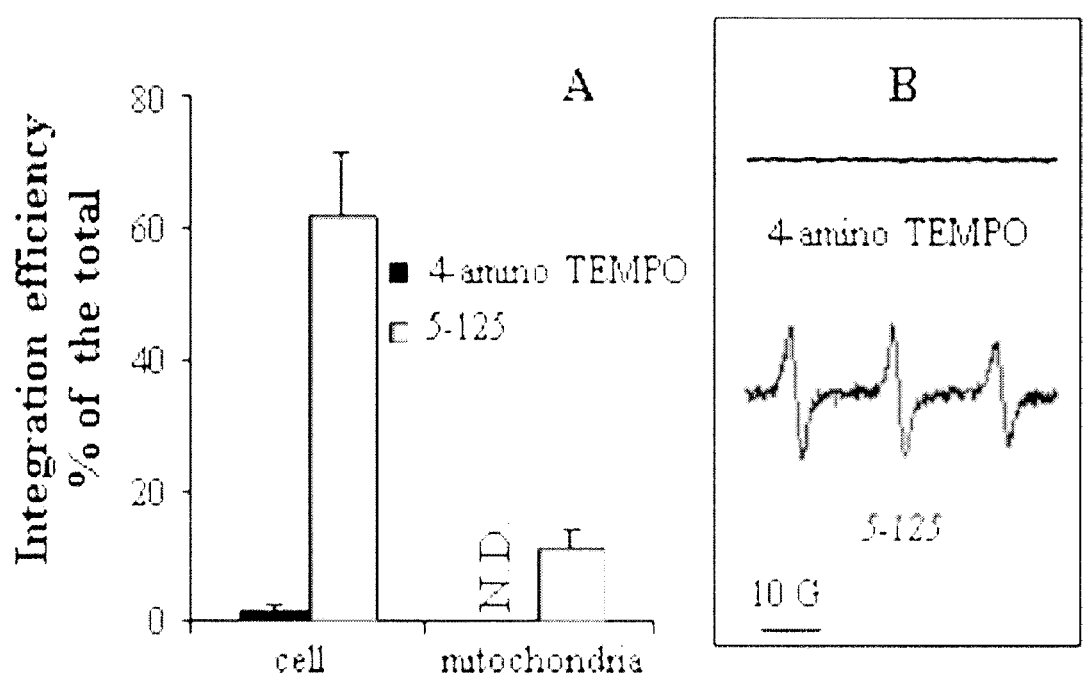
FIG. 12 shows that nitroxide conjugate XJB-5-125 integrates into cells and mitochondria much more efficiently than their parent non-conjugated 4-amino-TEMPO in mouse embryonic cells. (A) shows their cellular and mitochondrial integration efficiencies in mouse embryonic cells, and (B) shows representative EPR spectrum of nitroxides recovered from mitochondria.

FIG. 12 shows that nitroxide conjugate XJB-5-125 integrates into cells and mitochondria much more efficiently than their parent non-conjugated 4-amino-TEMPO in mouse embryonic cells. (A) shows their cellular and mitochondrial integration efficiencies in mouse embryonic cells, and (B) shows representative EPR spectrum of nitroxides recovered from mitochondria.

Figure 13:
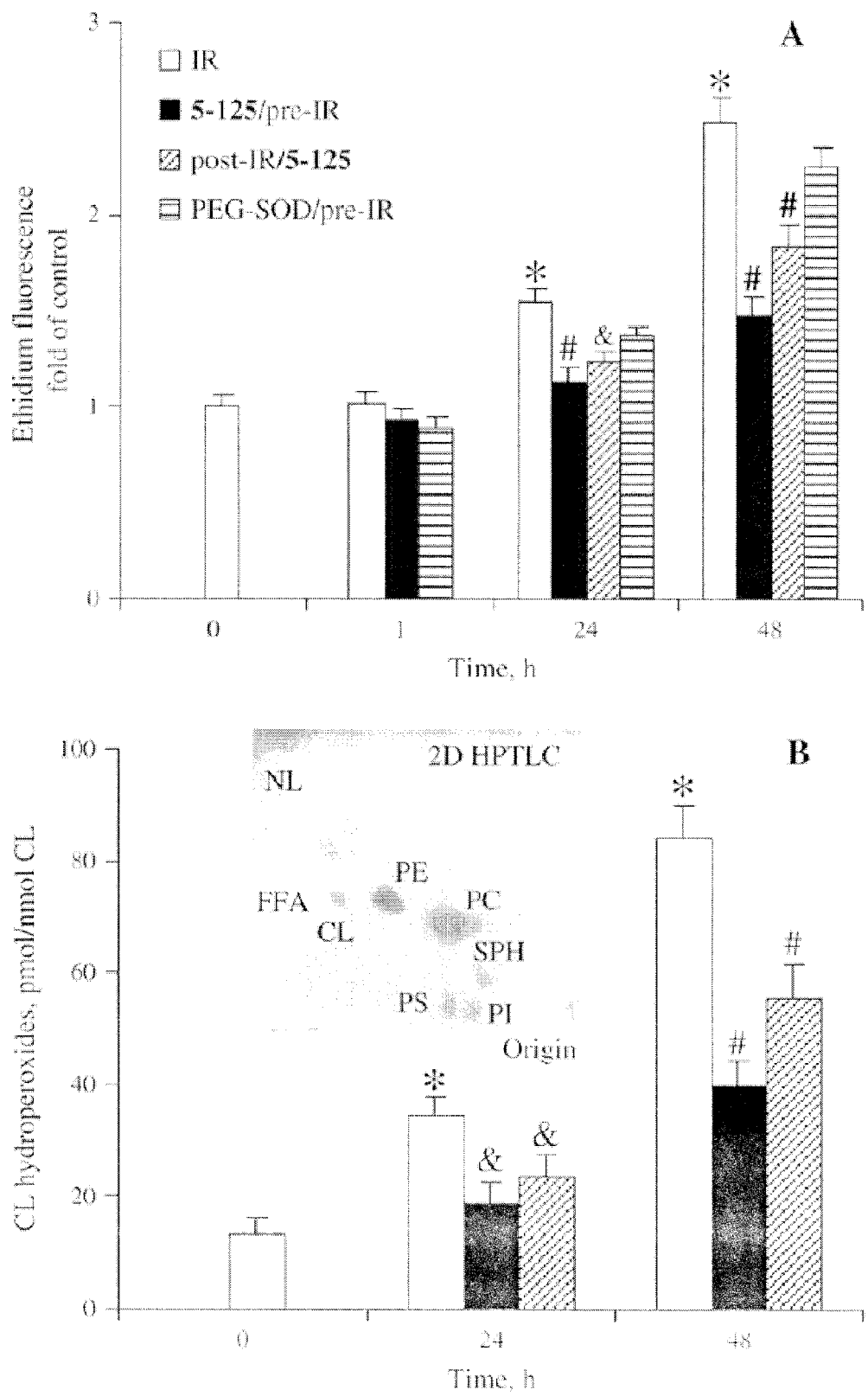
FIG. 13 reveals that nitroxide conjugate XJB-5-125 protects mouse embryonic cells against gamma irradiation induced superoxide generation and cardiolipin peroxidation. (A) superoxide generation. Cells were exposed to 10 Gy of γ-irradiation. XJB-5-125 (20 µM) was added to cells either 10-min before or 1-h after irradiation and removed after 5-h incubation. Cells were incubated with 5 µM DHE for 30 min at the indicated time points. Ethidium fluorescence was analyzed using a FACScan flow cytometer supplied with CellQuest software. Mean fluorescence intensity from 10,000 cells was acquired using a 585-nm bandpass filter. (B) Cardiolipin oxidation. Cardiolipin hydroperoxides were determined using a fluorescent HPLC-based Amplex Red assay. Data presented are means±S.E. (n=3). *p<0.01 vs non-irradiated cells; *p<0.01(0.05) vs irradiated cells without XJB-5-125 treatment under the same condition. Insert is a typical 2D-HPTLC profile of phospholipids from cells.

FIG. 13 reveals that nitroxide conjugate XJB-5-125 protects mouse embryonic cells against gamma irradiation induced superoxide generation and cardiolipin peroxidation. (A) superoxide generation. Cells were exposed to 10 Gy of γ-irradiation. XJB-5-125 (20 μM) was added to cells either 10-min before or 1-h after irradiation and removed after 5-h incubation. Cells were incubated with 5 μM DHE for 30 min at the indicated time points. Ethidium fluorescence was analyzed using a FACScan flow cytometer supplied with CellQuest software. Mean fluorescence intensity from 10,000 cells was acquired using a 585-nm bandpass filter. (B) Cardiolipin oxidation. Cardiolipin hydroperoxides were determined using a fluorescent HPLC-based Amplex Red assay. Data presented are means±S.E. (n=3). *p<0.01 vs non-irradiated cells; *p<0.01(0.05) vs irradiated cells without XJB-5-125 treatment under the same condition. Insert is a typical 2D-HPTLC profile of phospholipids from cells.

Figure 14:
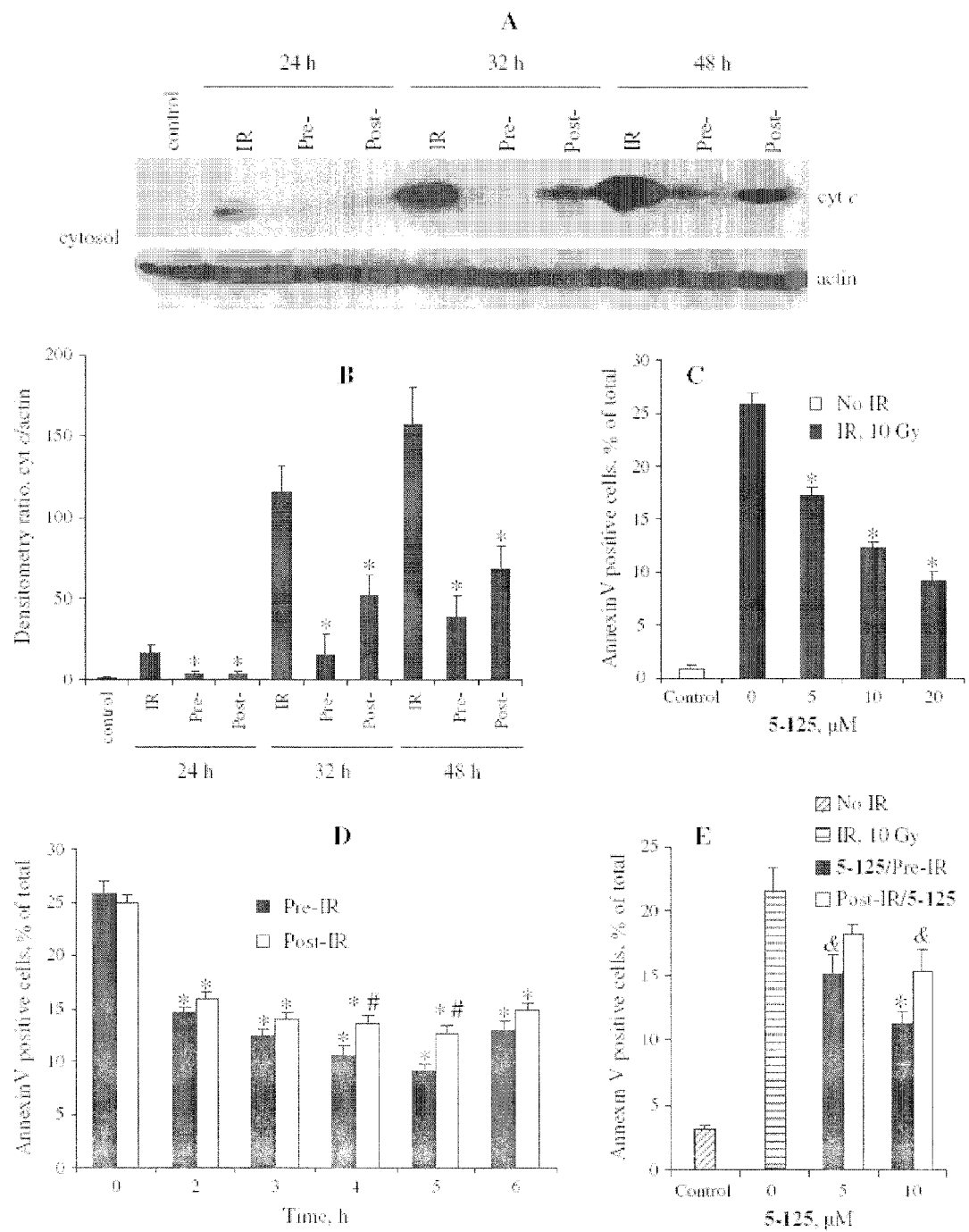
FIG. 14 reveals that nitroxide conjugate XJB-5-125 protects cells against gamma irradiation induced apoptosis. (A) XJB-5-125 blocks γ-irradiation induced accumulation of cytochrome c in the cytosol of mouse embryonic cells. (B) Densitometry ratio of cytochrome c/actin. Semi-quantitation of the bands was carried out by densitometry using Labworks Image Acquisition and Analysis Software (UVP, Upland, Calif.). The level of cytochrome c release was expressed as the mean densitometry ratio of cytochrome c over actin. (C) Dose (5, 10 and 20 µM) dependent radioprotective effect of XJB-5-125 (pre-treatment) on γ-irradiation (10 Gy) induced phosphatidylserine (PS) externalization. After 48 h post-irradiation incubation, cells were harvested and stained with annexin-V-FITC and propodium iodide (PI) prior to flow cytometry analysis. (D) Time (2, 3, 4, 5, and 6 h) dependent radioprotective effect of XJB-5-125 (20 µM) on γ-irradiation (10 Gy) induced PS externalization (48 h post irradiation) in mouse embryonic cells. (E) Effect of XJB-5-125 on γ-irradiation (10 Gy) induced PS externalization in human bronchial epithelial cell line BEAS-2B cells. Cells were treated with 5-125 (5 or 10 µM) before (10-min) or after (1-h) irradiation. Externalization of PS was analyzed 72 h post-irradiation exposure. Data shown are means±S.E. (n=3). *(&) p<0.01(0.05) vs irradiated cells without 5-125 treatment, #p<0.05 vs cells pre-treated with 5-125.

FIG. 14 reveals that nitroxide conjugate XJB-5-125 protects cells against gamma irradiation induced apoptosis. (A) XJB-5-125 blocks γ-irradiation induced accumulation of cytochrome c in the cytosol of mouse embryonic cells. (B) Densitometry ratio of cytochrome c/actin. Semi-quantitation of the bands was carried out by densitometry using Labworks Image Acquisition and Analysis Software (UVP, Upland, Calif.). The level of cytochrome c release was expressed as the mean densitometry ratio of cytochrome c over actin. (C) Dose (5, 10 and 20 μM) dependent radioprotective effect of XJB-5-125 (pre-treatment) on γ-irradiation (10 Gy) induced phosphatidylserine (PS) externalization. After 48 h post-irradiation incubation, cells were harvested and stained with annexin-V-FITC and propodium iodide (PI) prior to flow cytometry analysis. (D) Time (2, 3, 4, 5, and 6 h) dependent radioprotective effect of XJB-5-125 (20 μM) on γ-irradiation (10 Gy) induced PS externalization (48 h post irradiation) in mouse embryonic cells. (E) Effect of XJB-5-125 on γ-irradiation (10 Gy) induced PS externalization in human bronchial epithelial cell line BEAS-2B cells. Cells were treated with 5-125 (5 or 10 μM) before (10-min) or after (1-h) irradiation. Externalization of PS was analyzed 72 h post-irradiation exposure. Data shown are means±S.E. (n=3). *(&) p<0.01(0.05) vs irradiated cells without 5-125 treatment, #p<0.05 vs cells pre-treated with 5-125.

Figure 15:
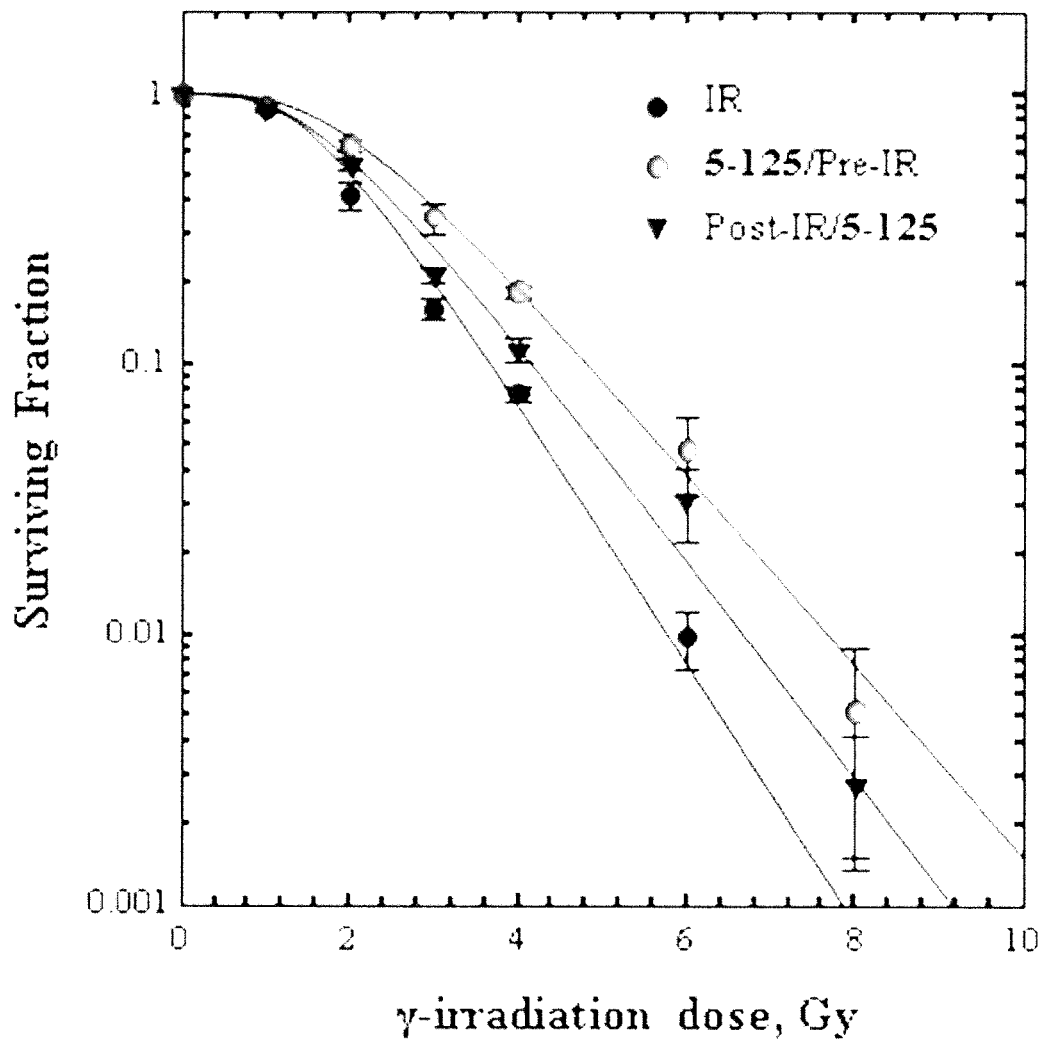
FIG. 15 shows the effect of nitroxide conjugate XJB-5-125 on gamma-irradiation dose survival curves of mouse embryonic cells. Cells were pre-(10-min) or post-treated (1-h) with XJB-5-125 (20 µM), which was removed after 4-h incubation period. The surviving fraction was calculated as the plating efficiency of the samples relative to that of the control. The data was fitted to a single-hit multitarget model using SigmaPlot 9.0 (Systat Software). Data presented are the mean±S.E. (n=3).

FIG. 15 shows the effect of nitroxide conjugate XJB-5-125 on gamma-irradiation dose survival curves of mouse embryonic cells. Cells were pre-(10-min) or post-treated (1-h) with XJB-5-125 (20 μM), which was removed after 4-h incubation period. The surviving fraction was calculated as the plating efficiency of the samples relative to that of the control. The data was fitted to a single-hit multitarget model using Sigma-Plot 9.0 (Systat Software). Data presented are the mean±S.E. (n=3).

Figure 16:
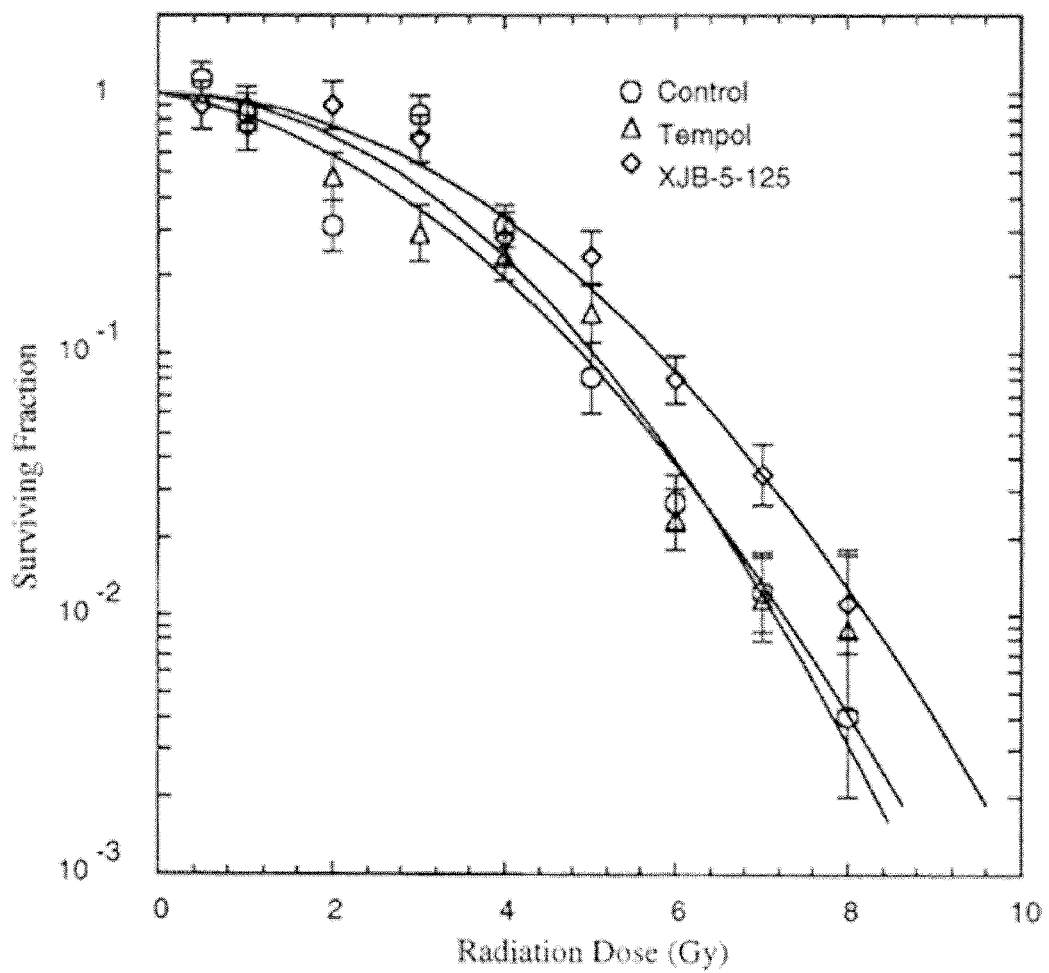
FIG. 16 illustrates the effect of GS conjugated nitroxide, XJB-5-125, on gamma-irradiation dose survival curves of 32D cl 3 murine hematopoietic cells. The cells incubated in XJB-5-125 or Tempol had an increased Do (1.138 or 1.209 Gy, respectively) compared to the 32D cl 3 cells (0.797 Gy). The cells incubated in XJB-5-125 had an increased shoulder on the survival curve with an n of 18.24 compared to 5.82 for the cells incubated in tempol.

FIG. 16 illustrates the effect of GS conjugated nitroxide, XJB-5-125, on gamma-irradiation dose survival curves of 32D cl 3 murine hematopoietic cells. The cells incubated in XJB-5-125 or Tempol had an increased Do (1.138 or 1.209 Gy, respectively) compared to the 32D cl 3 cells (0.797 Gy). The cells incubated in XJB-5-125 had an increased shoulder on the survival curve with an n of 18.24 compared to 5.82 for the cells incubated in tempol.

EXAMPLE 10

Testing of the Radioprotective Abilities of JP4-039

Figure 17A:
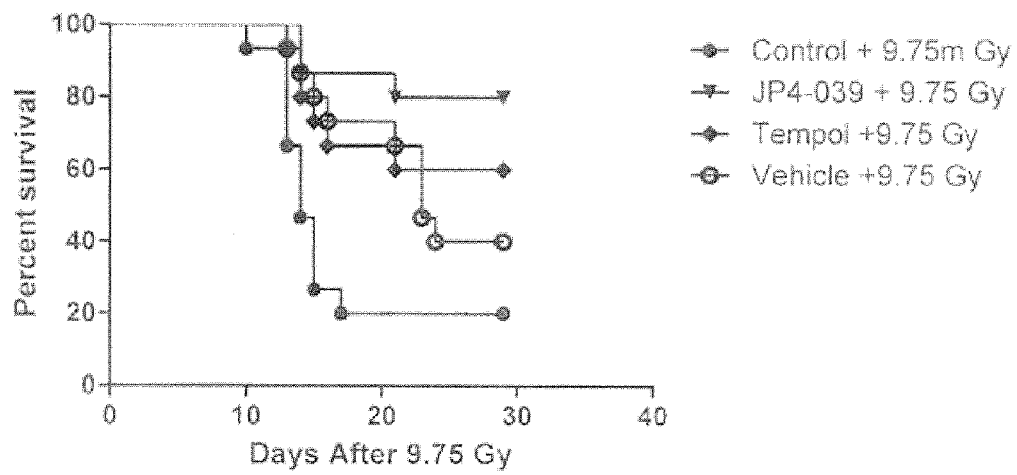
FIGS. 17A and 17B are graphs showing GS-nitroxide compound JP4-039 increases survival of mice exposed to 9.75 Gy total body irradiation.
Figure 17B:
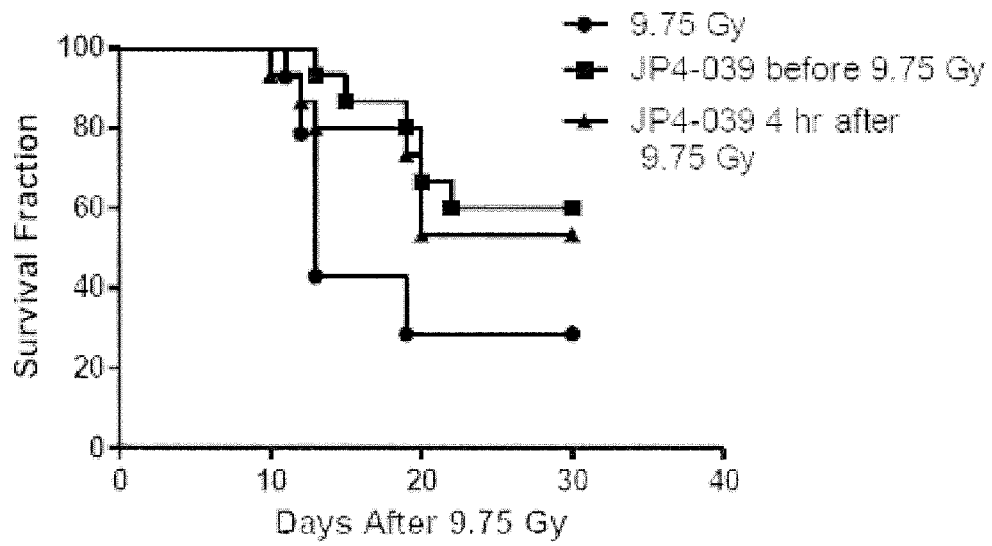

FIGS. 17A and 17B are graphs showing GS-nitroxide compound JP4-039 increases survival of mice exposed to 9.75 Gy total body irradiation. In FIG. 17A, mice received intraperitoneal injection of 10 mg per kilogram of each of the chemicals indicated in FIG. 5, then 24 hours later received 9.75 Gy total body irradiation according to published methods. Mice were followed for survival according to IACUC regulations. There was a significant increase in survival of mice receiving JP4-039 compared to irradiated control mice. (P=0.0008). In FIG. 17B, mice received intraperitoneal injection of JP4-039 either 10 minutes before (square symbols) or 4 hours after (triangle symbols) irradiation with 9.75 Gy.

Figure 18:
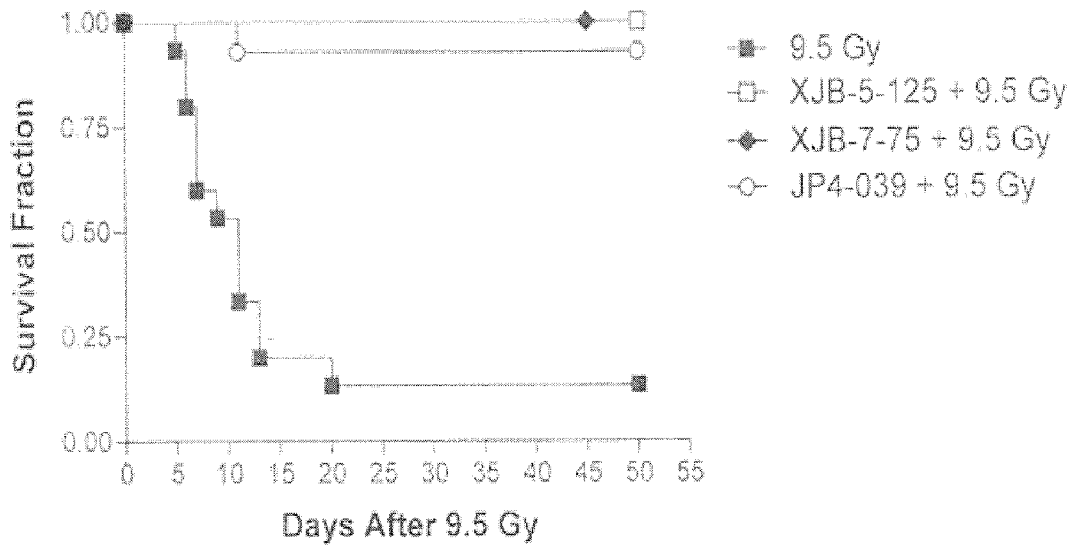
FIG. 18 is a graph showing that GS-nitroxide compound JP4-039 increases survival of mice exposed to 9.5 Gy total body irradiation.

FIG. 18 is a graph showing that GS-nitroxide compound JP4-039 increases survival of mice exposed to 9.5 Gy total body irradiation. Groups of 15 mice received intraperitoneal injection of 10 mg. per kilogram of each indicated GS-nitroxide compound or carrier (Cremphora plus alcohol at 1 to 1 ratio, then diluted 1 to 10 in distilled water). Mice received 10 mg per kilogram intra-peritoneal injection 24 hours prior to total body irradiation. Control mice received radiation alone. There was a statistically significant increase in survival in mice receiving GS-nitroxide compounds. (P=0.0005)

Figure 19:
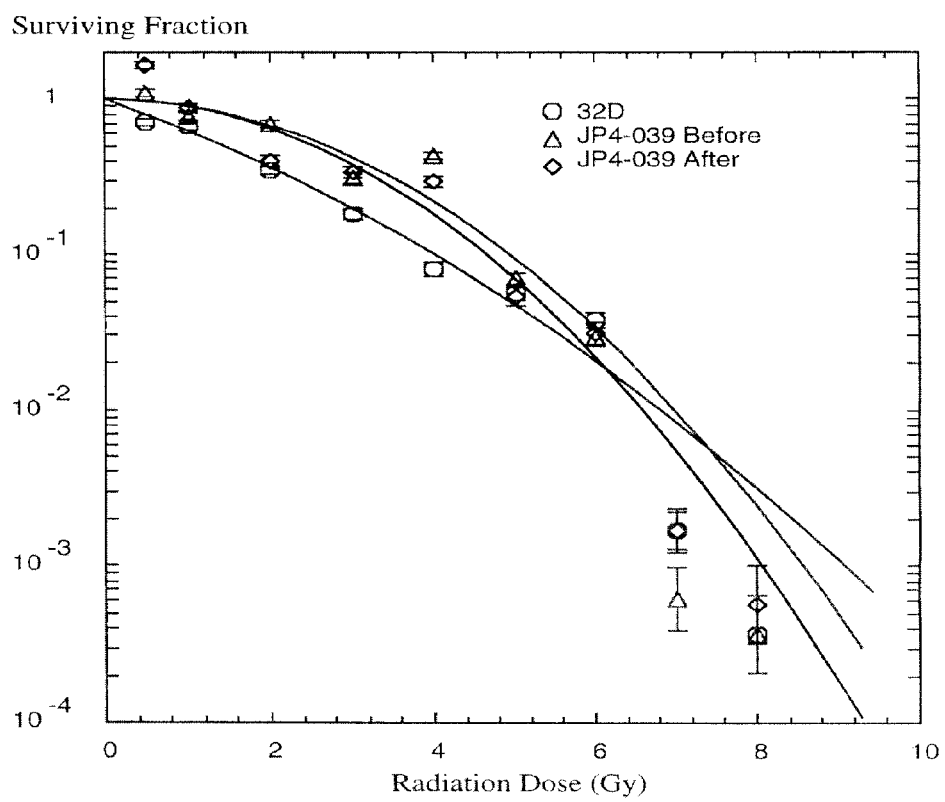
FIG. 19 is a graph showing that GS-nitroxide JP4-039 is an effective hematopoietic cell radiation mitigator when delivered 24 hr after irradiation.

FIG. 19 is a graph showing that GS-nitroxide JP4-039 is an effective hematopoietic cell radiation mitigator when delivered 24 hr after irradiation. Irradiation survival curves were performed on cells from the 32D cl 3 mouse hematopoietic progenitor cell line, incubated in 10 µM JP4-039 for 1 hour before irradiation, or plated in methylcellulose containing 10 µM JP4-030 after irradiation. Cells were irradiated from 0 to 8 Gy, plated in 0.8% methylcellulose containing media, and incubated for 7 days at 37° C. Colonies of greater than 50 cells were counted and data analyzed by linear quadratic and single-hit, multi-target models. Cells incubated in JP4-039 were more resistant as demonstrated by an increased shoulder on the survival curve with an ñ of 5.25±0.84 if drug was added before irradiation or 4.55±0.47 if drug was added after irradiation compared to 1.29+0.13 for 32D cl 3 cells alone (p=0.0109 or 0.0022, respectively).

Figure 20:
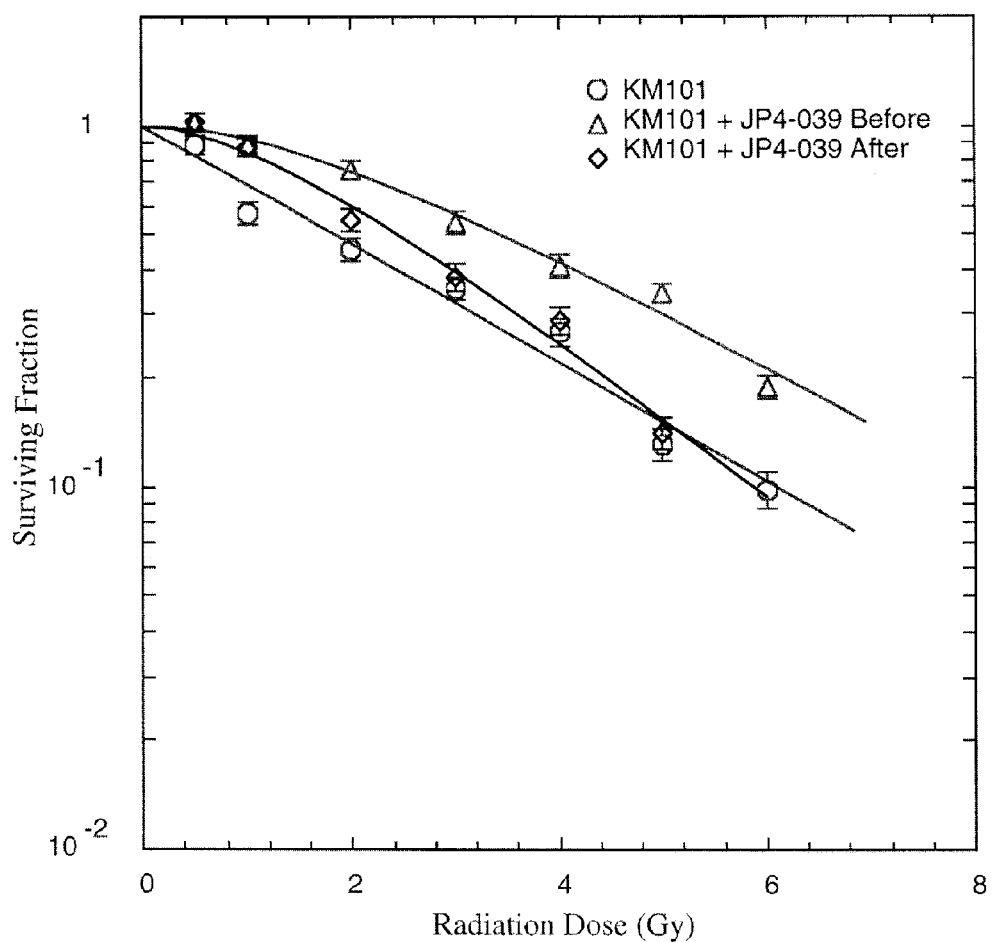
FIG. 20 is a graph showing that JP4-039 is an effective mitigator of irradiation damage to KM101 human marrow stromal cells.

FIG. 20 is a graph showing that JP4-039 is an effective mitigator of irradiation damage to KM101 human marrow stromal cells. KM101 cells were incubated in media alone or in JP4-039 (10 µM) for one hour before irradiation or 24 hours after irradiation. The cells were irradiated to doses ranging from 0 to 6 Gy and plated in 4 well plates. Seven days later the cells were stained with crystal violet and colonies of greater than 50 cells counted. Cells incubated in JP4-039 either before or after irradiation were more radioresistant as shown by an increased shoulder of n=2.3±0.2 or 2.2±0.2, respectively compared to n of 1.1±0.1 for the KM101 cells (p=0.0309 or 0.0386, respectively). There was no significant change in the Do for the different conditions.

EXAMPLE 11

NOD/SCID Mouse Model to Optimize JP4-039 for a Clinical Trial

Figure 21A:
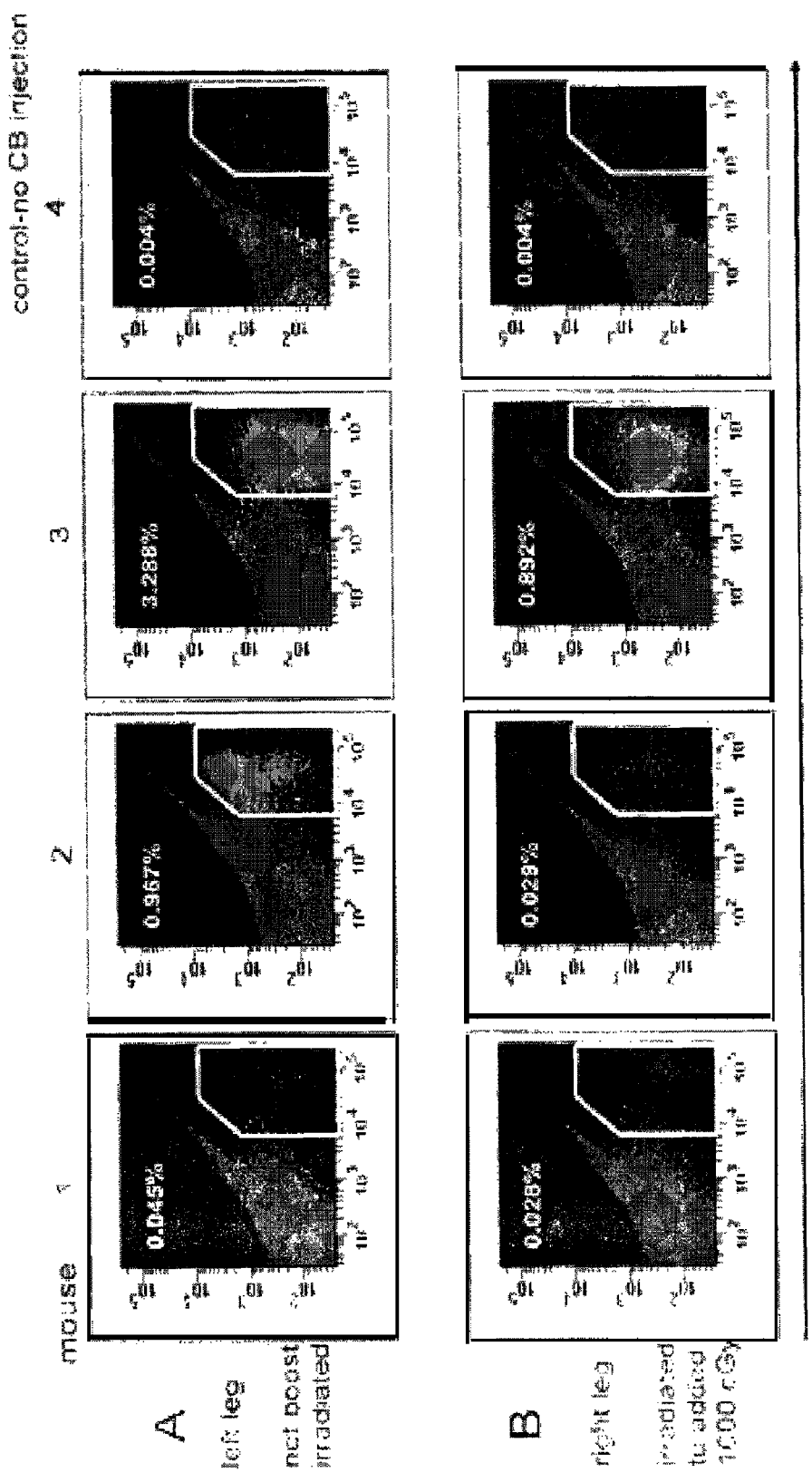
FIG. 21A shows results with detection of human cells in NOD/SCID mouse marrow harvested 27 days after cord blood transplanted I.V, showing flow cytometric analysis and identification of human CD45+ (light gray) hematopoietic cells in NOD/SCID mouse BM following irradiation, proximal tibia bone drilling (see below), and human cord blood injection.

We have significant preliminary data on use of NOD/SCID mice to test the effects of JP4-039 on human marrow stromal cell and hematopoietic stem cell recovery from total body irradiation to doses that cause the hematopoietic syndrome. FIG. 21A shows results with detection of human cells in NOD/SCID mouse marrow harvested 27 days after cord blood transplanted I.V, showing flow cytometric analysis and identification of human CD45+ (light gray) hematopoietic cells in NOD/SCID mouse BM following irradiation, proximal tibia bone drilling (see below), and human cord blood injection.

Six NOD/SCID mice were irradiated to 350cGy and injected with $1 \times 10^7$ human cord blood (CB) mononuclear cells (MNC). Five months after the CB MNC cells were initially injected, the right leg of 6 mice was irradiated to 10 Gy. 24 hours post-irradiation holes were drilled in the tibiae. (See FIG. 21B) Drill bit size 1 mm. diameter (Dremel Corp.). 24 hours post-bone drilling $1 \times 10^7$ CB MNC was injected into 3 of the 6 mice. Control mice (3) received no CB. 27 days after the CB was injected, the bones were harvested for histochemical analysis and flow cytometric analysis for human CD45+ cells (light grey) in the BM using a PE-conjugated anti-CD45 antibody (BD Biosciences). Analysis was performed on a BD LSR II flow cytometer (BD Biosciences). Human CD45+ cells were detectable in all of the mice (numbers 1-3) that received human CB MNC when compared to control mice (mouse 4). The percent of CD45+ cells ranged from 0.045-3.288 percent in the non boosted leg and from 0.028-0.892 percent in the high dose irradiated leg. There was no difference between the boost-irradiated and non boosted leg in these mice. Although the data suggest that there is a trend (the percent of human CD45+ cells was lower in the high dose irradiated leg), there was no statistically significant difference the total body irradiated non boosted compared to 1000 cGy boosted leg (p=0.25). Day 7 bone photo shown in FIG. 21B.

Figure 21B:
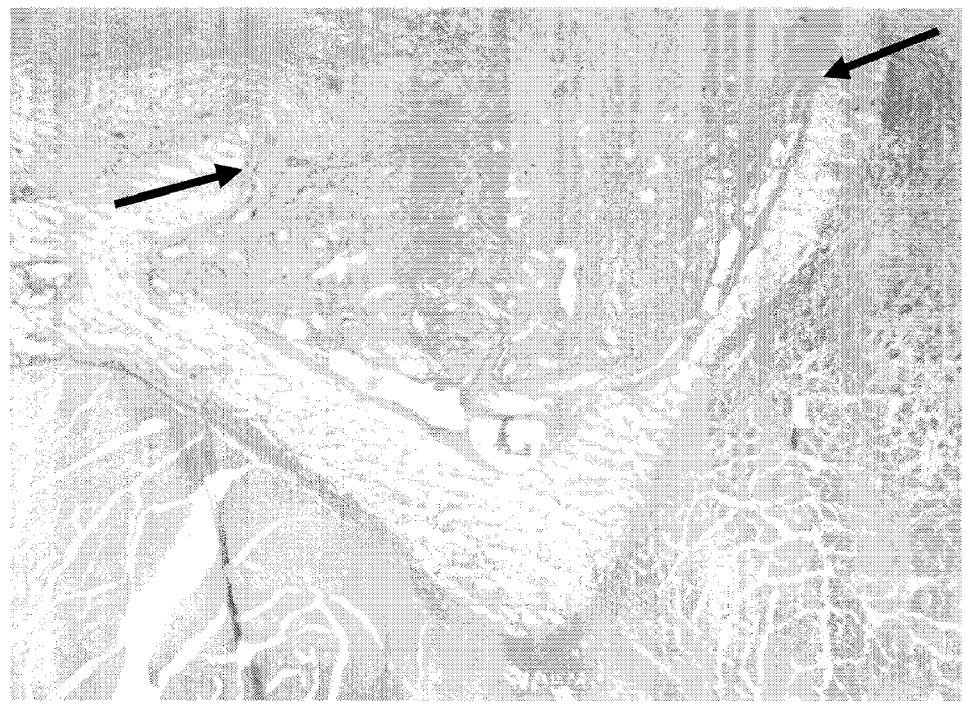
FIG. 21B is a photomicrograph of cross-section through a tibial wound 7-days after surgical construction with a drill bit of a unicortical 2-mm diameter wound in the lateral aspect of the tibia 2-mm below the proximal epiphyseal plate.

FIG. 21B is a photomicrograph of cross-section through a tibial wound 7-days after surgical construction with a drill bit of a unicortical 2-mm diameter wound in the lateral aspect of the tibia 2-mm below the proximal epiphyseal plate. Robust trabecular bone fills the intramedullary canal as well as the cortical window in this intermediate phase of spontaneous wound repair. This time point is optimal for assessing inhibition of marrow stromal cell mediated osteogenesis by irradiation and restoration by JP4-039, as proposed in this application. Arrows indicate margins of the wound. (Toluidine blue stain, ×35)(58)

EXAMPLE 12

Topical and transdermal absorption of GS-nitroxide. A practical skin patch is planned for delivery of JP4-039 or other compounds delivered herein. The patch can be administered to a subject before, during or after exposure to radiation, including 24 hr or later after irradiation exposure of the subject. In preliminary studies, we sought to characterize the absorption/penetration of a topically applied representative GS-Nitroxide XJB-5-125 in mouse skin. XJB-5-125 was selected as a potential topical agent based on its ability to inhibit ROS generation, inhibit apoptosis and suppress oxidative damage to mitochondrial lipids. XJB-5-125 comprises the (Leu-D-Phe-Pro-Val-Orn) segment of XJB-5-125 and has been shown to attenuate ActD-induced PS externalization in a dose-dependent manner of 2.5-20 µM. It can also inhibit the release of cytochrome c from mitochondria and suppress CL peroxidation. The physical properties of a chemical are critical to its ability to penetrate into and through the skin. Two important factors are the log octanal/water (Ko/w) partition coefficient and the molecular weight. For XJB-5-125, the log Ko/w=4.5 and molecular weight is 956. The lipophilicity "rule" is based on the need for a compound to partition out of the lipophilic stratum corneum and into the more hydrophilic epidermis and dermis. The log Ko/w and MW of XJB-5-125 are similar to ketaconazole (log Ko/w=4.34, MW=532), clotrimazole (log k/ow=6.27, MW=$_{902}$), and Indomethecin (log Ko/w=4.23, MW=358) suggesting feasibility of delivery using formulations similar to those used to effectively deliver these agents. Like JP4-039, XJB-5-125 is a radiation mitigator as well as a protector (see FIG. 15).

Figure 22:
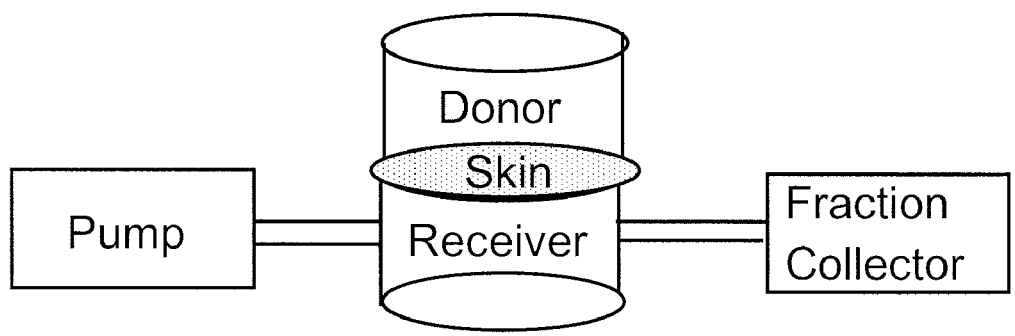
FIG. 22 is a schematic diagram of a Bronaugh diffusion system for studying in vitro transdermal flux.
Figure 23:
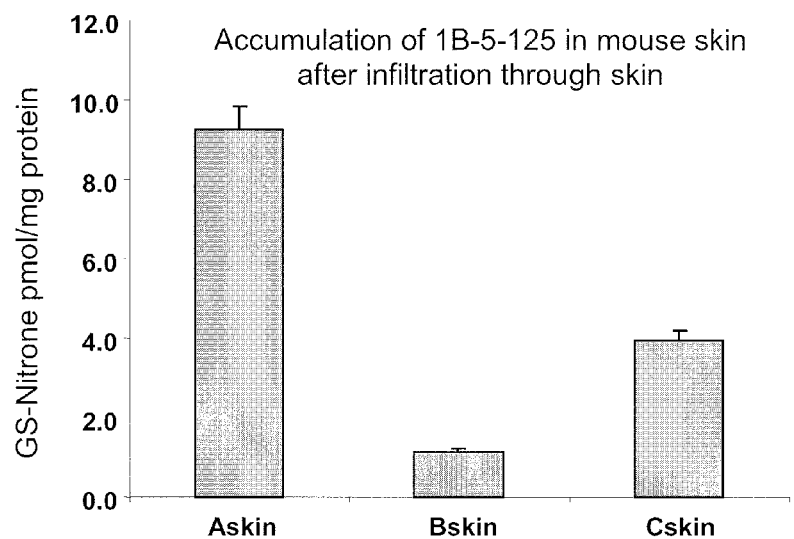
FIG. 23 is a graph showing delivery of XJB-5-125 into mouse skin after 24 hours.
Figure 24:
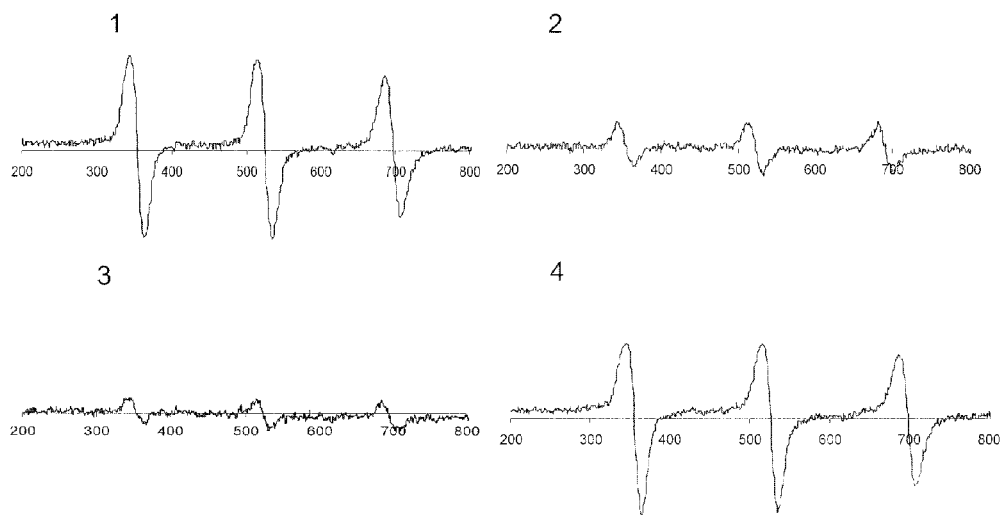
FIG. 24 shows typical EPR spectra of GS-nitroxides recorded from different fractions obtained after the filtration through the mouse skin. 1—donor fluid, 2—receiver fluid after 6 h of solution A filtration, 3—receiver fluid after 6 h of solution B filtration, 4—skin after 24 h exposure to solution A. The EPR spectra of GS-nitroxide radicals in medium, or skin homogenates were recorded in 28.5% of acetonitrile with addition of 2 mM $K_3Fe(CN)_6$
Figure 25:
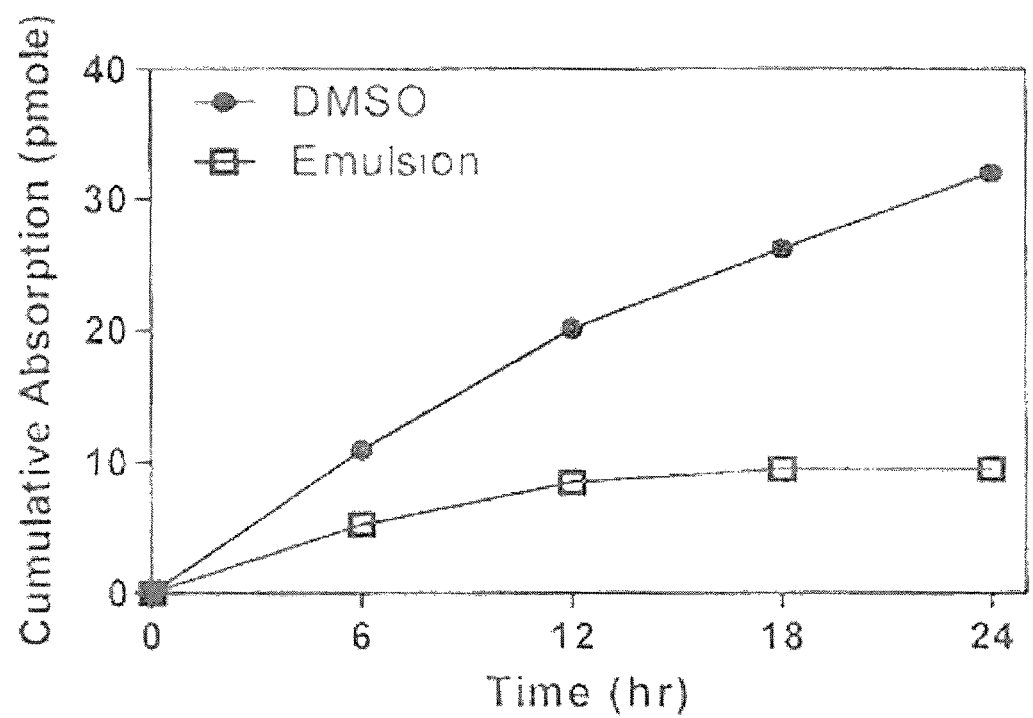
FIG. 25 is a graph showing cumulative transdermal absorption of XJB-5-125 through mouse skin over 24 hours FIGS. 26A and 26B provides structures for compounds JED-E71-37 and JED-E71-58, respectively.

A small piece of skin (2 cm$^2$) was placed in a Bronaugh style flow-through diffusion cell system (PermeGear, Riegelsville, Pa.) (FIG. 22). It was then sandwiched between two pieces of the inert polymer Kel-F and clamped shut to prevent leakage. The epidermal side faces upward and is exposed to the donor solution (test solution), and the dermal side is in contact with the receptor fluid. The exposed surface area is 0.79 cm$^2$ (circular chamber with 1 cm diameter). The skin forms a water-tight seal in the flow through chamber so the receiving fluid (PBS+25% ethanol) on the dermal side will contain the XJB-5-125 only if it has penetrated through the skin. The receiver chamber was perfused with this buffer that then passes to a fraction collector via Teflon tubing. The PBS+25% ethanol was used because it is an effective sink for hydrophobic compounds and produces better in vitro/in vivo correlations than other receiver solutions. The skin was maintained at 32° C. by placing the chamber in a metal block heated via a recirculating water bath. The skin was equilibrated for 60 minutes prior to introduction of the test compound. Seventy five µL of XJB-5-125 was placed on the skin and was allowed to remain for the course of the experiment. The efflux was collected for 24 hours. (FIGS. 23-25).

To evaluate XJB-5-125 penetration in mouse skin, C57/BL6 mice were shaved using animal clippers (#40 blade), followed by a brief treatment with Nair (depilatory) to remove remaining hair. The skin was washed immediately after hair removal to prevent further irritation. The skin was allowed to recover for 24 hours prior to study. This reduces interference by hair and allows time for small abrasions to heal prior to dermal penetration studies.

Upon completion of the study, the skin was removed from the diffusion chamber. The stratum corneum, which will contain the majority of the topically applied compound, but is not relevant from a therapeutic standpoint, was removed by sequential tape-stripping (15 times) using Brookman Tape (3M, Minneapolis, Minn.). The remaining skin (viable epidermis and dermis) and transdermal effluent were assayed for XJB-5-125 via ESR.

Mouse skin was homogenized in 400 µL 50 mM PBS pH 7.4. EPR measurements were performed in gas-permeable Teflon tubing (0.8 mm internal diameter, 0.013 mm thickness) obtained from Alpha Wire Corp. (Elizabeth, N.J., USA) on a JEOL JES-RE1X spectrometer at 25° C. The Teflon tube (approximately 8 cm in length) was filled with 70 µL of sample containing 28.5% of acetonitrile and 2 mM $K_3Fe(CN)_6$, folded in half, and placed into an open EPR quartz tube (inner diameter of 3.0 mm). (FIG. 24)

EPR spectra were recorded at 334.7 mT, center field; 20 mW, power; 0.079 mT, field modulation; 5 mT, sweep width; 400 and 4000, receiver gain; 0.1 s, time constraint. Spectra were collected using EPRware software (Scientific Software Services, Bloomington, Ill., USA).

These preliminary experiments demonstrate that XJB-5-125 can sufficiently penetrate intact skin. Further, the total transdermal absorption after 24 hours and the level of XJB-5-125 present in the viable skin can be successfully measured using the techniques described herein. The effect of formulation on topical delivery was examined by using three different donor solutions (FIG. 25). Donor A=1 mM XJB-5-125 in DMSO, donor B=1 mM XJB-5-125 in 95% Propylene Glycol+5% Linoleic Acid, and Donor C=1 mM XJB-5-125 in 50% EtOH+40% HSO+5% Propylene Glycol+5% Brij30. A total of 75 nmole was placed on top of each piece of skin to begin these experiments (75 ul of 100 mM). The delivery of XJB-5-125 into the skin resulted in between 0.07% and 0.46% remaining within the skin after 24 hours. The higher delivery rate is in the range of other topical products.

Given the observation that XJB-5-125 is active in cells in the concentration range from 2.5-20 µM and assuming a tissue density of 1 g/cm$^3$, an order of magnitude analysis based on these data indicates that the topical delivery of XJB-5-125 method to enhance systemic blood levels to protect bone marrow is feasible.

Additionally, the fact that the total skin absorption is generally regarded as linearly related to the donor concentration implies that topical delivery will be greatly enhanced by increasing the donor concentration. These preliminary studies demonstrate feasibility of XJB-5-125 delivery to therapeutic levels and indicate that the smaller JP4-039 molecule, as well as other compounds described herein, may be useful as a skin patch-deliverable radiation mitigator of the hematopoietic syndrome.

EXAMPLE 13

Proposed

The following can be used to select and optimize the best GS-nitroxide JP4-039 (radiation damage mitigator drug) that can enhance human bone marrow stromal cell and fresh human stromal cell line seeding efficiency into irradiated limbs of NOD/SCID mice. MnSOD-overexpressing cells are a positive control.

Experiments with KM101-MnSOD/ds-red (control KM101-ds-red) clonal cell lines. Groups of 12 NOD/SCID mice receive 300 cGy total body irradiation (low dose leg) and a 1000 cGy boost to the left hind leg (high dose leg), then 24 hours later intravenous injection of $1\times10^5$ or $1\times10^6$ cells of each cell line (groups 1 and 2). Group 3 is mice that receive MnSOD-PL intravenously 24 hours prior to irradiation and then injection of KM101-MnSOD/ds-red. Group 4 is MnSOD-PL intravenously 24 hours prior to irradiation, then control KM101/ds-red cells. This experiment may be repeated twice. Mice will have bone marrow flushed from the hind limbs at days 1, 3, 7, 14 after cell transplantation, and scoring of the percent of total cells and number of colony forming cells recoverable which are ds-red positive thus of human origin. The scoring may be by ds-red positivity, and then by colony formation in vitro by stromal cells. We may score the total, then the percent of stromal cells of human origin.

Experiments demonstrating improvement in human bone marrow stromal cell line KM101 seeding by mitochondrial targeted radiation protection/mitigation JP4-039 (GS-nitroxide) administration. This experiment may be conducted essentially as described above (A), with all groups, but with a sub-group receiving JP4-039 (24 hours) after radiation (same day as cell lines are injected, or a sub-group receiving intraperitoneal JP4-039 (daily or weekly after cell line transplantation). Cells may be explanted from the high dose and low dose irradiated femurs at days 7, 14, 21, and cultured in vitro for human stromal colony forming progenitor cells (CFU-F). The percent and total number of human cells entering the high dose and low dose irradiated limbs can be quantitated by cell sorting for ds-red. Each experiment can be completed twice.

Experiments as in (A) above, but substituting fresh human marrow Stro1+stromal cells from a 45 y.o. donor.

Experiments as in (B) above substituting Stro1+human marrow stromal cells.

Statistical considerations—In (A), we propose comparing at 4 different time points between 4 groups where either MnSOD or no MnSOD, and either $10^5$ or $10^6$ KM101 cells are injected, in terms of the number of DsRed-KM101 cells. In (B), we propose comparing at 3 different time points between 10 groups where different doses and schedules of the experimental compound will be used, in terms of the same endpoint as in (A). (C) and (D) are the same as (A) and (B) respectively, except that human stromal cells are used in place of KM101 cells. All the comparisons in this task are performed separately for high and low dose radiated legs. ANOVA followed by Tukey's test can be used for these analyses. Sample size can be estimated by the two sample t-test for pairwise comparisons. Due to the lack of preliminary data, sample size estimation is based on the expected difference to detect between groups in terms of the common standard deviation σ. Six mice per group can be sacrificed per time point. With this sample size, there will be 82% power to detect a difference of 1.8σ between groups using the two sided two sample t test with significance level 0.05.

As the secondary endpoint, the number of colony forming unit fibroblast (human) CFU-F can also be compared between groups with the same method as the primary endpoint.

It is expected that MnSOD overexpression in KM101-MnSOD/ds-red cells will lead to a higher seeding efficiency into both the high and low dose irradiated limbs of NOD/SCID mice. We expect that MnSOD-PL treatment of the hematopoietic microenvironment prior to KM101 clonal line cell line infusion will further enhance engraftment of both KM101-MnSOD/ds-red and KM101-ds-red cell lines. We expect the highest percent of seeding efficiency will be detected in the mice receiving MnSOD-PL prior to irradiation and injection of KM101-MnSOD/ds-red cells.

We expect that JP4-039 administration daily after cell transplantation will facilitate improved stability of engraftment of all stromal cell lines by decreasing free radical production by the irradiated marrow microenvironment.

An inactive control compound for JP4-039 may be used, (JP4-039 absent the nitroxide active moiety). Based upon the results of these experiments, the optimal condition for bone marrow stromal cell seeding can be derived, and these conditions may be used in experiments described below.

EXAMPLE 14

Proposed

Selection and optimization of a GS-nitroxide JP4-039 therapy to enhance human CD34+ cord blood multilineage hematopoietic stem cell progenitor cell seeding into irradiated limbs of NOD/SCID mice that have been prepared by engraftment of human marrow stromal cells.
  i. Experiments with TBI treated C57BL/6J mice and mouse marrow screening. (preliminary system test)
  ii. Experiments using the optimal seeding protocol for human KM101 cells into irradiated NOD/SCID mice (anticipated to be those mice receiving MnSOD-PL prior to irradiation, and then injection with KM101-MnSOD/ds-red, supplemented with JP4-039 daily). Mice can then receive intravenous injection of $1\times10^5$ or $1\times10^6$ CD34+ LIN− cells from human umbilical cord blood origin. Control cells may be CD34+ LIN+ (differentiated progenitor) cells $10^5$ or $10^6$ per injection. Groups of 12 mice.

These experiments may be carried out in two schedules.
  Injection of cord blood cells at the same time as KM101-MnSOD/ds-red cells.
  Injection of cord blood cells at time of optimal recovery of KM101-MnSOD/ds-red cells from the explant experiments of Example 13. This should be at day 7 or day 14 after stromal cell injection.

In these experiments, mice can be followed and tested at serial time points out to two months after cord blood stem cell transplantation. The percent of human peripheral blood hematopoietic cells can be scored in weekly peripheral blood samples and number of cells forming CFU-GEMM colonies can be tested in explanted bones from sacrificed mice.

At days 7, 14, 21, 28, or 60 after cord blood transplantation, mice in sub-groups may be sacrificed, and all cells flushed from the high dose and low dose irradiated femurs, and assays carried out for human multilineage hematopoietic progenitors-CFU-GEMM. Assays may be carried out by two methods:
  i. Sorting human CD34+ cells with monoclonal antibodies specific for human.
  ii. Colony formation in human CFU-GEMM culture medium and then secondary scoring of human colonies as the subset of total mouse and human colony forming cells detected at days 7 and days 14 in vitro.

In vitro experiments may be carried out in parallel as follows:
  KM101-MnSOD-PL plateau phase stromal cells may be irradiated in vitro to 100, 200, 500, 1000 cGy, and then CD34+ LIN− human cord blood cells co-cultivated with the stromal cells in vitro. Controls can include unirradiated KM101-MnSOD/ds-red, irradiated KM101-ds-red cells, unirradiated KM101-ds-red.

We can score human cobblestone islands (stem cell colonies) on these cultures weekly, plot cumulative cobblestone island formation, cumulative non-adherent cell production with weekly cell harvest, and assay of weekly cell harvest for CFU-GEMM formation. These studies may be carried out over two-three weeks. In vitro co-cultivation studies can only partially duplicate the in vivo hematopoietic microenvironment, and thus two weeks should be the maximum efficient time for detection of whether MnSOD-PL expression in the adherent KM101 layer will increase engraftment of cord blood stem cells.

3. Experiments with JP4-039 supplementation of the cord blood transplantation program as in (1) above to increase homing, stable quiescence, and repopulation capacity of human cord blood stem cells by removing ROS production in the irradiated marrow stromal cell environment.

Experiments in vitro supplementing in co-cultivation culture media the drug JP4-039 daily. The experiments with irradiated KM101 subclonal lines, co-cultivated with cord blood stem cells may be carried out with the addition of JP4-039, or an active analog JP4-039 daily. Control experiments can include addition of CD34+ LIN+ differentiated cord blood cells that are expected to produce fewer CFU-GEMM over time. Stromal cell cultures may be irradiated, cord blood cells added, and cultures scored as above.

Groups of 12 mice can receive the optimal protocol for human CFU-GEMM cell engraftment from the experiment above, and then sub-groups can be treated as follows:
  i. JP4-039 twice weekly.
  ii. JP4-039 daily.
  iii. Inactive JP4-039 analog daily.

4. Experiments as in (1) above substituting fresh human Stro1+ marrow cells for KM101 subclonal lines.

5. Experiments as in (2) above substituting human Stro1+ marrow cells for KM101 subclonal lines.

Statistical considerations—In (1), we can compare at 5 different time points between 7 groups where we use MnSOD-KM101 and/or $10^5/10^6$ CD34+ cells, in terms of the number of CD45+ cells. In (2), we can compare at 5 different time points between 7 groups that use KM101, CD34+ cells, KM101 plus CD34+ cells, the experimental compound single or double administrations, or inactive analog of the experimental compound single or double administrations, in terms of the same endpoint as in (1). Tasks (3) and (4) are the same as (A) and (B) of Example 13, respectively, except that we can use human Stro1+ marrow cells in place of KM101 cells. All the comparisons in this task can be performed separately for high and low dose radiated legs. ANOVA followed by Tukey's test can be used for these analyses. Similar to the sample size considerations in Example 13, we will use 6 mice per group at each time point. As the secondary endpoint, the number of CFU-GEMM can also be compared between groups with the same method as the primary endpoint.

Likely Outcomes—Based on the results of Example 13, we expect that cord blood stem cell and human bone marrow stromal cell homing in vitro will be optimized by MnSOD-PL treatment of the mouse microenvironment prior to stromal cell transplantation, and that MnSOD-PL overexpressing KM101 cells will show further stability in the irradiated microenvironment. We expect that JP4-039 treatment will further enhance hematopoietic cell survival and increase CFU-GEMM in numbers.

EXAMPLE 15

Proposed

These experiments utilize osteogenesis by human stromal cells as a measure of effective mitigation of marrow injury by JP4-039. JP4-039 can be tested for repair of artificial fracture of the proximal tibiae in NOD/SCID mice by human stromal cell derived osteoblasts producing human collagen and can show enhanced fracture healing by antioxidant JP4-039 treatment.

Experiments with mice engrafted with KM101-MnSOD/ds-red compared to KM101 cells. Mice may have holes drilled in both proximal tibias as described above, then irradiation 300 cGy total body dose, 1000 cGy to one hind limb, and then 24 hours later injection of $1 \times 10^5$ bone marrow stromal cells of each line. Mice can be followed for 21 days and at serial seven days time points tibias explanted and assayed for relative content of human collagen in the healed bones.

JP4-039 weekly or daily supplemented injections in a repeat experiment of experiment described in (A) (12 mice per group).

Mice receiving MnSOD-PL intravenously 24 hours prior to irradiation (on the day of bone drilling), and then injection of either KM101-MnSOD/ds-red or KM101-ds-red.

Mice receiving scrambled sequence MnSOD-PL injection prior to cell line injection as described in (C) above.

Experiments as in (A-D) substituting fresh Stro1+ stromal cells for KM101 subclones.

Statistical considerations—In (A), we compare at 3 different time points 17 groups that use KM101 cells, MnSOD, the experimental compound single or double administrations, scrambled MnSOD, or a combination of some of these, in terms of the percent of human collagen. (B) is the same as (A) except that human Stro1+ marrow cells are used in place of KM101 cells. All the comparisons in this task can be performed separately for high and low dose radiated legs. ANOVA followed by Tukey's test can be used for these analyses. Similar to the sample size considerations in Example 13, we can use 6 mice per group at each time point.

Likely Outcomes—We expect that KM101-MnSOD/ds-red will demonstrate improved osteogenic capacity in vivo. We anticipate that MnSOD-PL administration to mice 24 hours prior to irradiation will further enhance homing and osteoblast differentiation of KM101-MnSOD/ds-red.

Preliminary data show radiation survival curves of bone marrow stromal cell lines and enhancement of survival by MnSOD overexpression. Other preliminary data are expected to show that each Stro1+ cell transfected with MnSOD-PL and KM101-MnSOD/ds-red as well as KM101-ds-red are capable to differentiation to osteoblasts in vitro (osteogenic media experiments in progress) and in vivo in hole drilled NOD/SCID mice. Radiation survival curves of KM101-MnSOD/ds-red and KM101-ds-red treated with JP4-039, but not the inactive analog of JP4-039 are shown above. We anticipate that three conditions: 1) MnSOD-PL administration to the microenvironment, 2) overexpression of MnSOD in bone marrow stromal cell lines of human origin, and 3) supplementation of JP4-039 antioxidant therapy will lead to maximum osteogenic differentiation by human origin collagen producing cells. As further controls for the experiments, we can determine whether hematopoietic cells of human origin are required for optimal functioning of bone marrow stromal cells. KM101-MnSOD/ds-red stromal cell seeded NOD/SCID mice can be supplemented with injection of human cord blood CD34+ LIN−, or CD34+ LIN+ cells administered either with the stromal cells, or 24 hours later, to see if these cells produce optimal colony formation. Other controls can be CD34+ LIN−, CD34+ LIN+ hematopoietic cells only. Other controls may include STRO1+ stromal cells progenitors from cord blood alone or whole cord blood controls.

EXAMPLE 16

Figure 32:
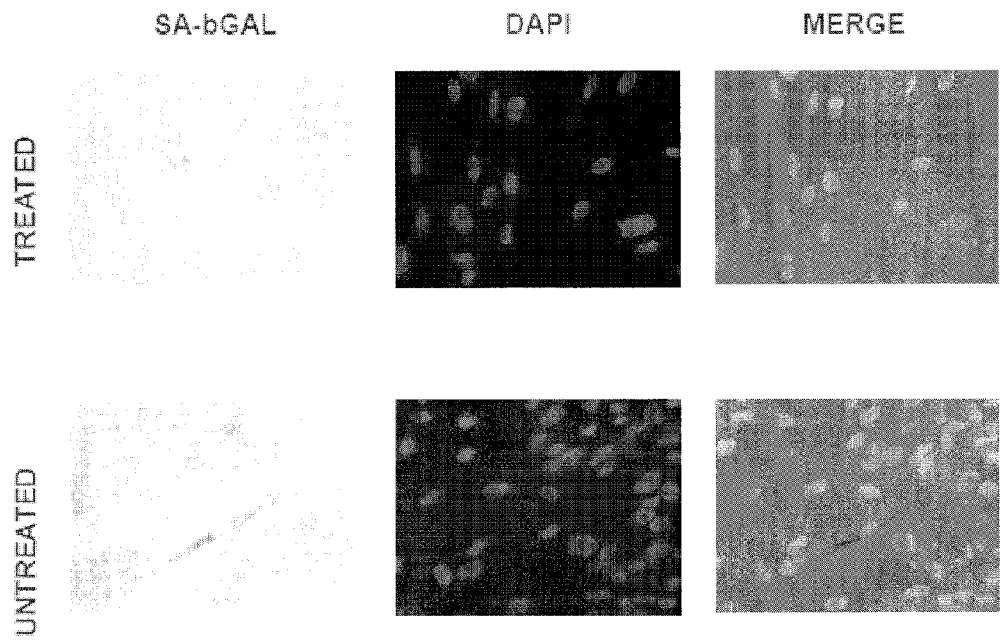
FIG. 32 provides photomicrographs of SA-β galactosidase (a marker of cellular senescence) staining in mouse embryonic fibroblast ("MEF") cells prepared from Ercc1$^{-/-}$ mice, where the MEF cells were either treated with XJB-5-131 ("XJB" in this figure; 500 nM dissolved in media) or media alone continuously for 48 hr prior to fixing and staining the cells.

To assess the effectiveness of XJB-5-131 in inhibiting degeneration and/or signs of aging, the compound was administered, over an 18-21 week period, progeroid Ercc1$^{-/\Delta}$ mice, at a dose of 2 mg/kg in sunflower oil carrier (to promote solubility) administered intraperitoneally three times per week (FIG. 32). Sunflower seed oil was administered to twin Ercc1$^{-/\Delta}$ mice according to the same schedule as a control. The treated and control mice were monitored twice a week for weight and symptom/sign development.

Figure 33:
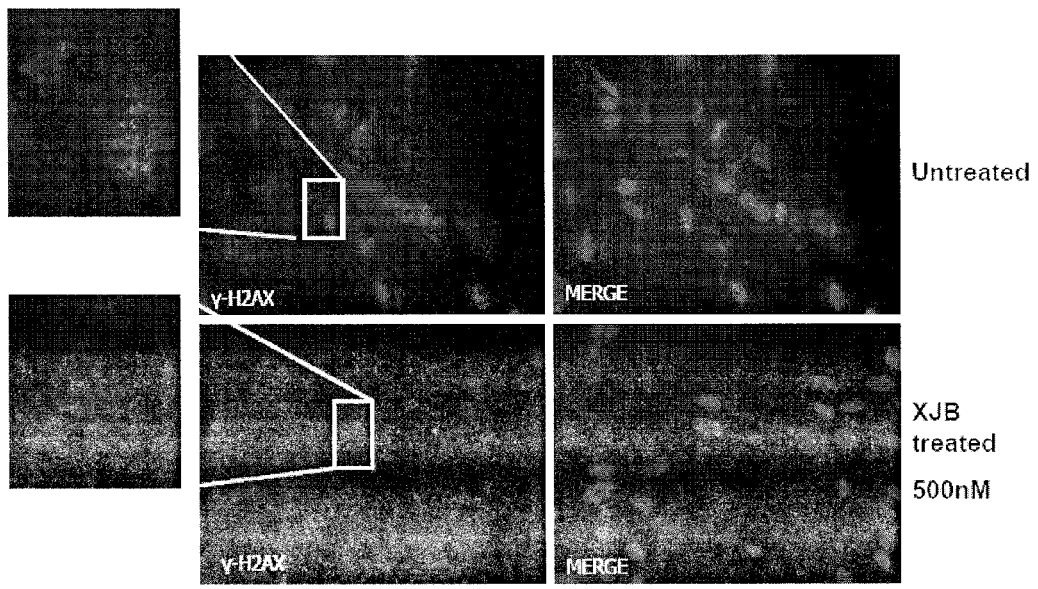
FIG. 33 provides photomicrographs of γH2AX immunostaining (a marker of DNA double strand breaks and cellular senescence) of mouse embryonic fibroblast ("MEF") cells prepared from Ercc1$^{-/-}$ mice, where the MEF cells were either treated with XJB-5-131 ("XJB" in this figure; 500 nM dissolved in media) or media alone continuously for 48 hr prior to fixing and staining the cells.

FIG. 33 presents a summary table showing the results of the treatment with XJB-5-131 ("XJB" in this figure), relative to control (sunflower seed oil) after treatment from 5 wks of life until death. The numbers indicate the average age at onset of each age-related symptom for mice treated with XJB-5-131 or vehicle only (oil) (n=5 mice per group). Cells highlighted in yellow indicate symptoms that were significantly delayed by XJB-5-131. In addition to improvement in most signs measured, the overall aging score was significantly improved in the XJB-5-131-treated mice. Of note, all of the signs of neurodegeneration, including dystonia, trembling, ataxia, wasting and urinary incontinence were delayed in the treated animals, providing strong evidence that XJB-5-131 protects neurons against degenerative changes caused by oxidative stress.

Figure 34:
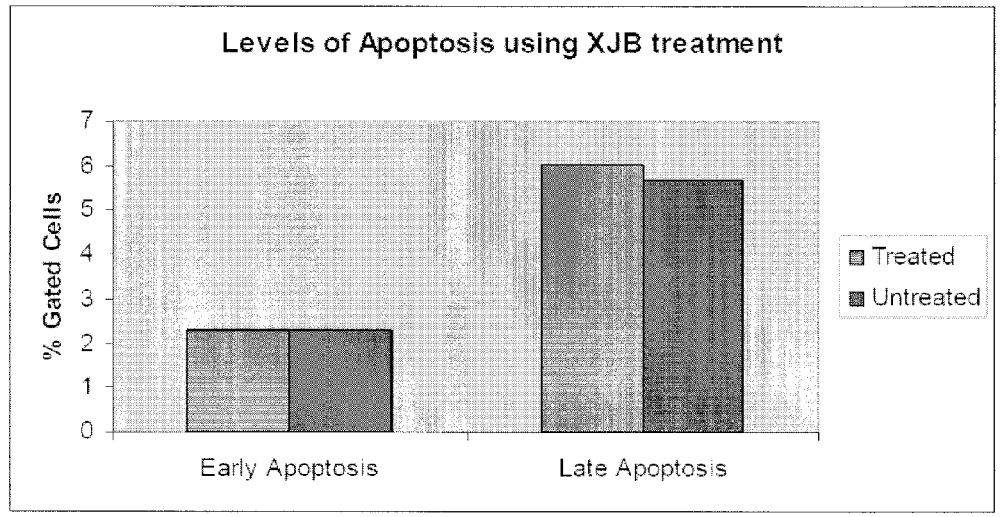
FIG. 34 is a graph showing apoptosis in mouse embryonic fibroblast ("MEF") cells prepared from Ercc1$^{-/-}$ mice, where the MEF cells were either treated with XJB-5-131 ("XJB" in this figure; 500 nM dissolved in media) or media alone continuously for 48 hr prior to fixing and staining the cells.

To assess the ability of XJB-5-131 to inhibit deterioration of intervertebral discs (an index of degenerative disease of the vertebra), the level of glycosaminoglycan in the discs in treated and control mice were measured, and the results are shown in FIG. 34. The intervertebral discs of treated mice contained approximately 30 percent more glycosaminoglycan relative to control mice, indicating inhibition of disc degeneration.

As a measure of the effect of XJB-5-131 on photoaging, Ercc1$^{-/cond}$;K14-Cre mice, which are missing ERCC1 only in the skin, were shaved, treated with a depilatory then irradiated with UV-B light to induce a sunburn (500 J/m$^2$, the median erythemal dose). Subsequently, the mice were treated with XJB-5-131 (80 μg) emulsified in a cream daily for five days. The results, shown in FIG. 35, indicate that the skin of treated mice appeared much more smooth and healthy relative to control (mice treated with cream only).

Figure 36:
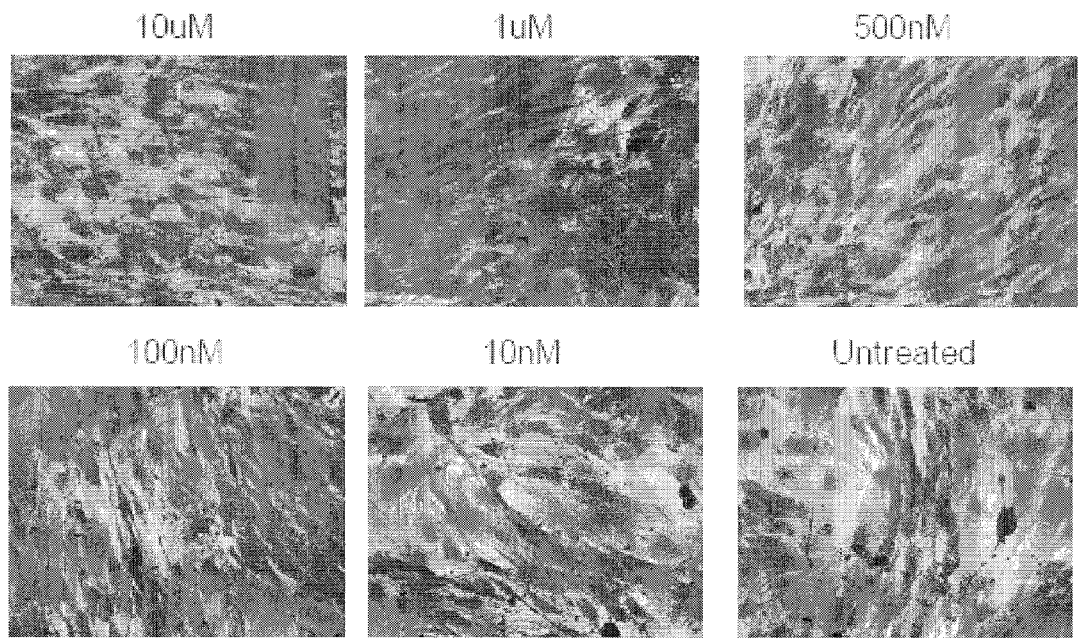
FIG. 36 provides photomicrographs showing the effects of varying doses of JP4-039 on proliferation and growth of mouse embryonic fibroblast ("MEF") cells prepared from wild-type mice. JP4-039 is not toxic to cells at concentrations as high as 10 μM.
Figure 37:
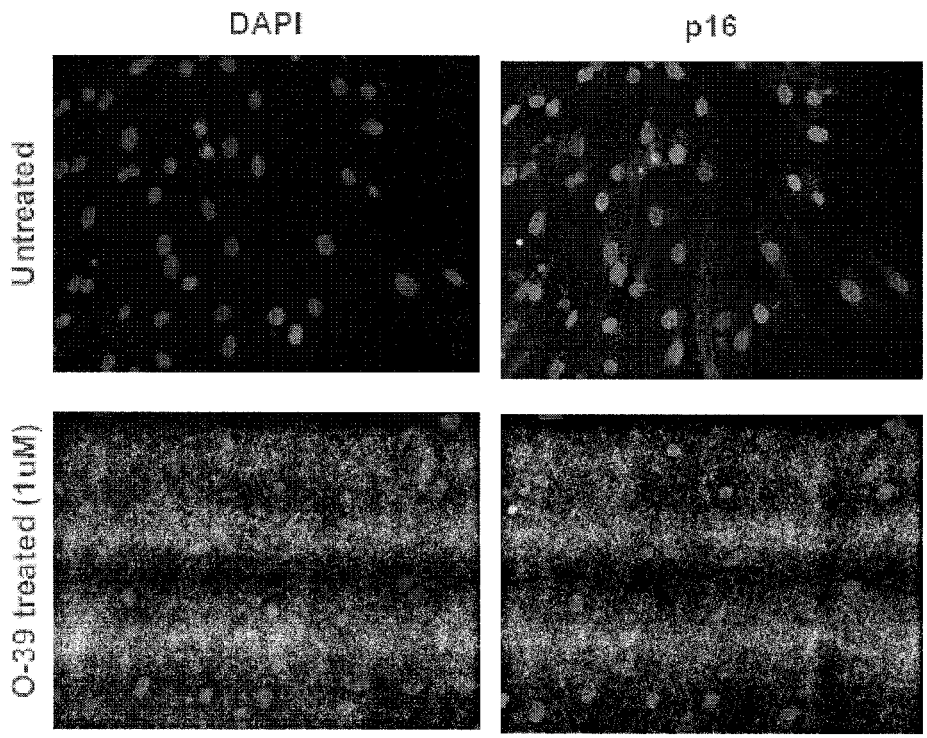
FIG. 37 provides photomicrographs showing levels of p16, a marker of irreversible cellular senescence, in mouse embryonic fibroblast ("MEF") cells prepared from Ercc1$^{-/\Delta}$ mice, where the MEF cells were either treated with either JP4-039 ("0-39" in this figure; 10 μM dissolved in media) or media alone for 48 hrs prior to fixing and immunostaining the cells.
Figure 38:
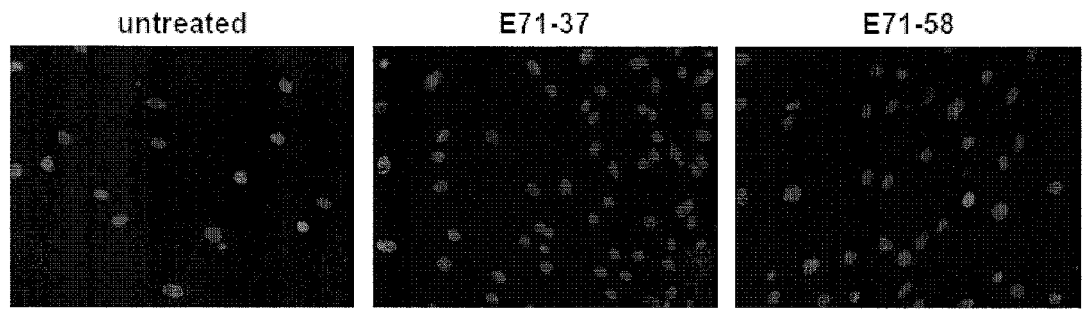
FIG. 38 provides photomicrographs showing cell proliferation of primary mouse embryonic fibroblast ("MEF") cells prepared from Ercc1$^{-/-}$ mice and grown in conditions of oxidative stress (20% oxygen), where the MEF cells were either treated with either JED-E71-37, JED-E71-58 91 uM dissolved in media), or media alone for a duration of 48 hrs prior to fixing and staining the cells.
Figure 39:
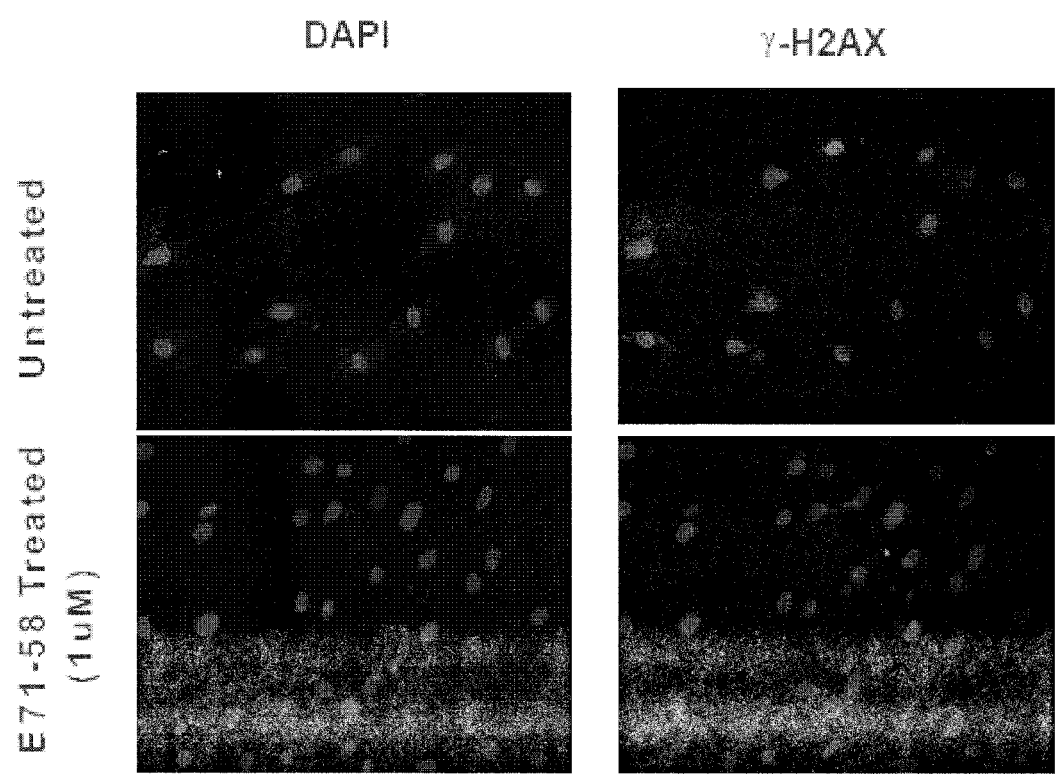
FIG. 39 provides photomicrographs showing γH2AX immunostaining (a marker of DNA double strand breaks and cellular senescence) of mouse embryonic fibroblast ("MEF") cells prepared from Ercc1$^{--\Delta}$ mice and grown in conditions of oxidative stress (20% oxygen), where the MEF cells were either treated with either JED-E71-58 (1 μM dissolved in media, or media alone for a duration of 48 hrs prior to fixing and staining the cells.

At a macroscopic level, administration of XJB-5-131 appears to have been well-tolerated by the animals, as indicated by the fact that they did not lose weight as a result of treatment. Graphs showing weight over time of treated, untreated and control animals are shown in FIG. 36A-B. To assess the impact of XJB-5-131 at a cellular level, a number of experiments were carried out using mouse embryonic fibroblasts ("MEF") cells harvested from Ercc1$^{-/-}$ mouse embryos. As shown in FIG. 37, such MEF cultures were prepared and grown under ambient oxygen (oxidative stress) conditions, and then either untreated (media only) or treated with a concentration of 500 nM (in media) XJB-5-131, and then tested for SA-β galactosidase staining (a marker of cellular senescence). The amount of staining was notably less in the treated cells. In addition, XJB-5-131 treatment was found to reduce the number of γH2AX foci in DNA (a second marker of cellular senescence as well as DNA double-strand breaks) (FIG. 38), although it did not reduce the amount of apoptosis (FIG. 39).

EXAMPLE 17

Protective Effects of JP4-039

Figure 35:
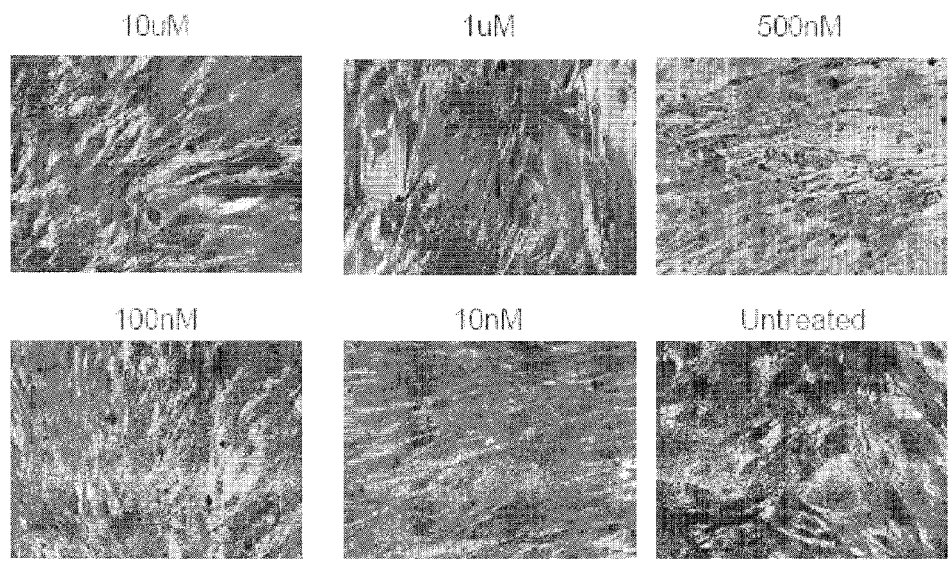
FIG. 35 provides photomicrographs showing the effects of varying doses of JP4-039 on proliferation and growth of mouse embryonic fibroblast ("MEF") cells prepared from Ercc1$^{-/-}$ mice. JP4-039 is not toxic to cells at concentrations as high as 10 μM.

To assess the therapeutic potential of JP4-039, tests for safety and protective activity were performed. FIGS. 35 and 36 show the results of tests to evaluate whether varying concentrations of JP4-039 produce toxic effects after 48 hours in cultures of MEF cells prepared from Ercc1$^{-/-}$ or wild-type mouse embryos, respectively. Even under the highest concentrations tested (10 µM), no signs of toxicity were observed in either culture system and cellular proliferation is enhanced relative to untreated control cells (media only).

To test the protective activity of JP4-039, cultures of primary MEFs were prepared from Ercc1$^{-/-}$ mouse embryos and grown under 20% oxygen (ambient air), which creates oxidative stress in these cells that are hypersensitive to reactive oxygen species. The cells were then either treated with a concentration of 1 µM XJB-5-131, JP4-039, JED-E71-37 or JED-E71-58, or left untreated (media), and then after 48 hrs the level of p16, a marker of irreversible cellular senescence, was measured by immunofluorescence staining. As seen in FIG. 37, the level of p16 was much lower in MEF cells treated with JP4-039 relative to its level in untreated cells, whereas XJB-5-131, JED-E71-37 and JED-E71-58 were observed to be less effective at this concentration.

EXAMPLE 18

Protective Effects of Antioxidants in Cell Culture

To evaluate the protective activities of JED-E71-37 and JED-E71-58, primary MEF cells were prepared from Ercc1$^{-/-}$ mice and grown under conditions of oxidative stress (ambient air, 20% oxygen). The cells were then either untreated or treated with 1 µM JED-E71-37 or JED-E71-58 for a period of 48 hours. As can be seen in FIG. 38, both compounds improved cell proliferation despite the oxidative stress.

Next, the abilities of these two agents, as well as XJB-5-131 and JP4-039, each at a concentration of 1 µM, were tested for their ability to prevent oxidation-induced DNA double-strand breaks in cell cultures prepared, and oxidatively stressed, as in the preceding paragraph. Treated as well as untreated cells were, after 48 hours of treatment, immunostained for γ-H2AX, a marker of DNA double-strand breaks as well as cellular senescence. Results for JED-E71-58 are shown in FIG. 39, showing a distinct decrease in γ-H2AX. JP4-039 was also effective, but XJB-5-131 and JED-E71-37 were observed to be less effective at this concentration.

EXAMPLE 19

Alternative Designs of Nitroxide Analogues

Figure 40:
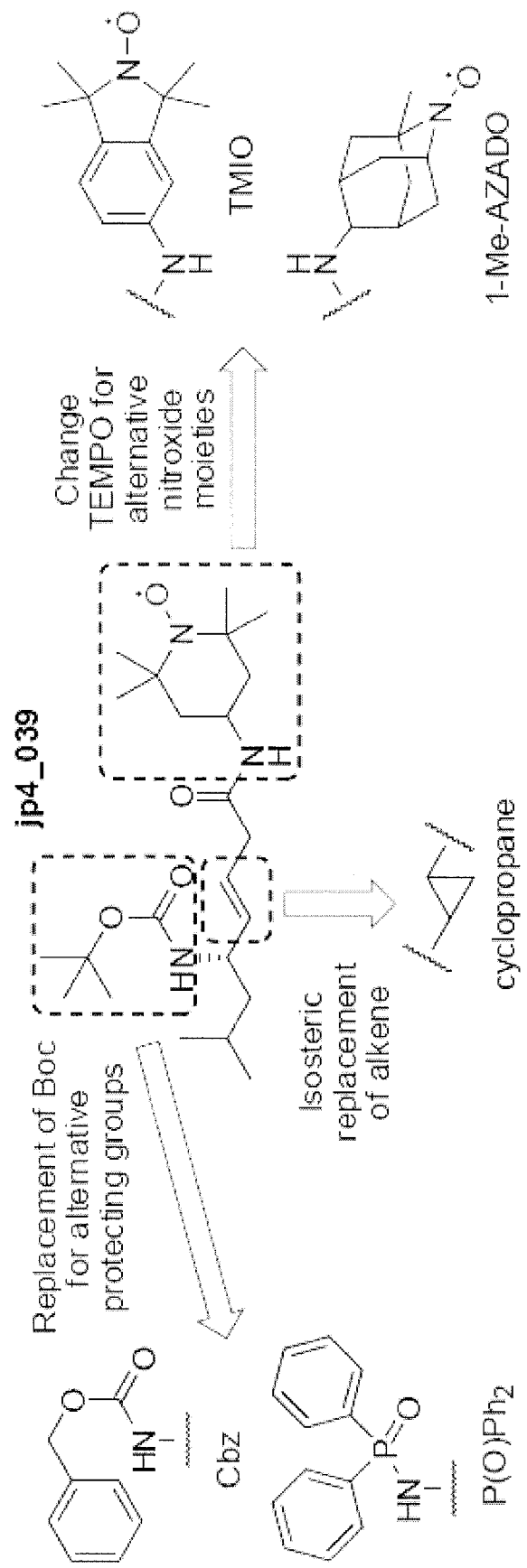
FIG. 40 is a schematic showing alternative designs of nitroxide analogues.

To further investigate the structural requirements for high activity of GS-nitroxide compound JP4-039, we have designed several nitroxide analogues. FIG. 40 shows a schematic of alternative designs of nitroxide analogues. The design can encompass one or both of: modification of the targeting group to optimize the drug-like properties and/or investigation of alternative nitroxide containing groups to improve their oxidant efficiency (for example and without limitation, see Reid, D. A. et al The synthesis of water soluble isoindoline nitroxides and a pronitroxide hydroxylamine hydrochloride UV-VIS probe for free radicals. Chem. Comm. 1998, 17:1907-8; Iwabuchi, Y. J., Exploration and Exploitation of Synthetic Use of Oxoammonium Ions in Alcohol Oxidation. J. Synth. Org. Chem. Jpn. 2008, 66(11):1076-84). Modification of the targeting group can include replacement of Boc for alternative protecting groups, such as Ac (—C(O)CH$_3$), Cbz (—C(O)O-Bn, where Bn is a benzyl group) or dialkylphosphates. Dialkylphosphates include —P(O)-Ph$_2$, where Ph is a phenyl group. Other modifications also include isosteric replacement of the alkene group within the targeting group, such as with a cyclopropane group. The nitroxide containing group includes TEMPO and TEMPOL, as well as alternative nitroxide moieties, such as TMIO (1,1,3,3-tetramethylisoindolin-2-yloxyl) or 1-Me-AZADO (1-methyl 2-azaadamantane N-oxyl). Synthesis protocols of these alternative nitroxide moieties are provided below.

Figure 41:
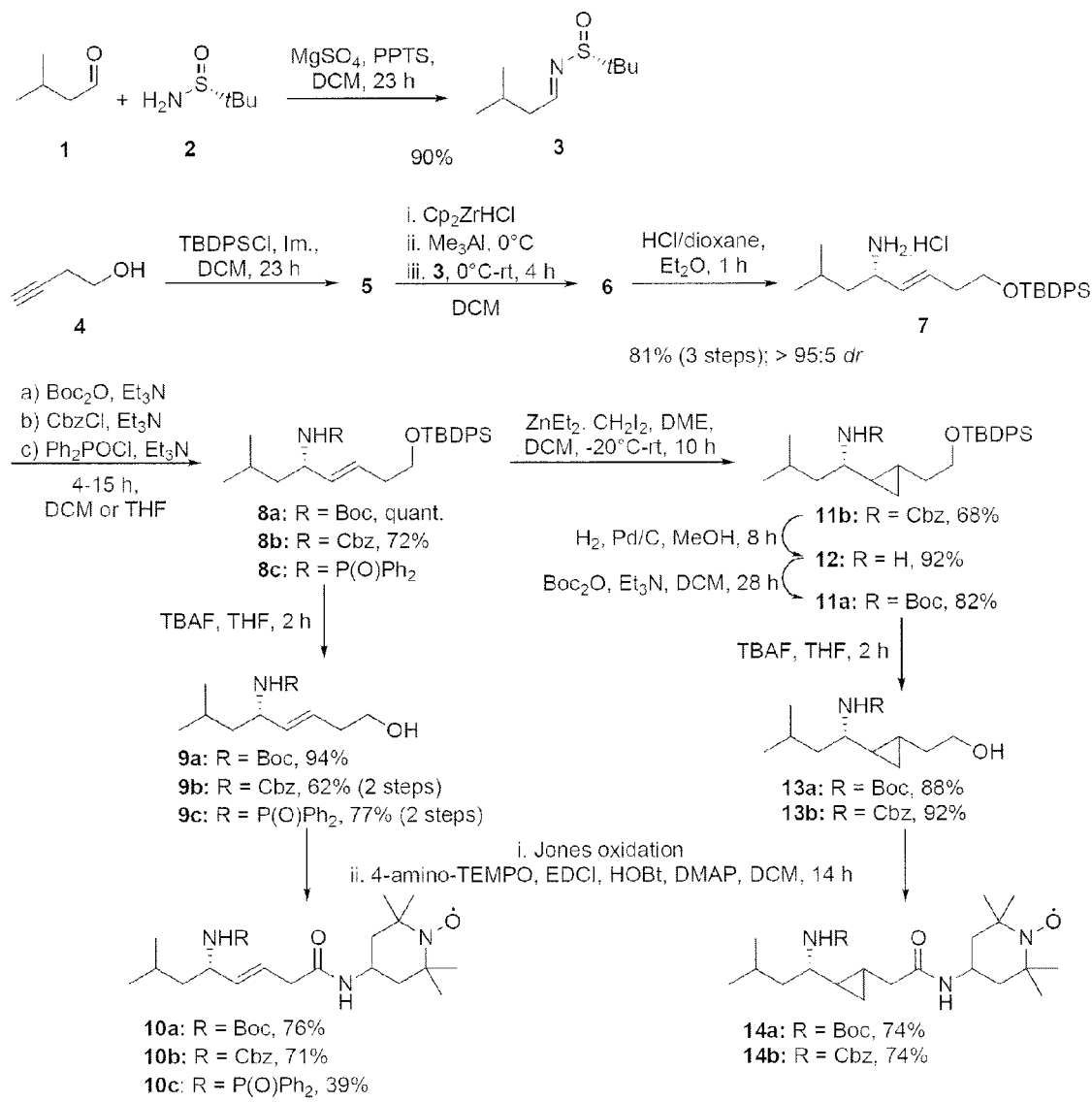
FIG. 41 is a schematic of a synthesis protocol for various alternative designs of nitroxide analogues.

FIG. 41 shows a synthetic protocol that can be used to produce various alternative designs of nitroxide analogues, including JP4-039, compounds according to Formula 2, compounds according to Formula 3, and other analogues. The specific synthesis of JP4-039 has been described above in Example 8. JP4-039 and its analogues were prepared via an efficient method for the asymmetric synthesis of allylic amines, previously developed in our laboratory (Wipf P. & Pierce J. G. Expedient Synthesis of the α-C-Glycoside Analogue of the Immunostimulant Galactosylceramide (KRN7000), Org. Lett. 2006, 8(15):3375-8). One key step in FIG. 41 includes use of the zirconium methodology to produce a diastereomeric allylic amine (7). This methodology includes hydrozirconation of alkyne (5) with Cp$_2$ZrHCl, transmetalation to Me$_3$Al, and addition to N-tBu-sulfinyl amine (3). The Smith cyclopropanation of the alkene (8b) with Zn(CH$_2$I)$_2$ is another key step in FIG. 41. In this latter step, the stereochemistry around the cyclopropane ring is to be determined after the reaction.

Synthesis of compounds (10a, JP4-039), (10b), (10c), (14a), and (14b) (shown in FIG. 41) was accomplished according to the following.

(R,E)-2-Methyl-N-(3-methylbutylidene)propane-2-sulfinamide (3). The synthesis of the title compound has already been described in Example 8 (compound 1).

(But-3-ynyloxy)(tert-butyl)diphenylsilane (5). The synthesis of the title compound has already been described in Example 8 (compound 2).

(S,E)-8-(tert-Butyldiphenylsilyloxy)-2-methyloct-5-en-4-amine hydrochloride (7). The synthesis of the title compound has already been described in Example 8 (compound 3).

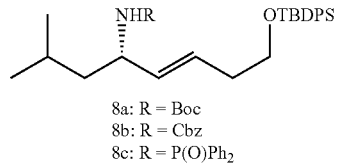

8a: R = Boc
8b: R = Cbz
8c: R = P(O)Ph$_2$ (S,E)-tert-Butyl 8-(tert-butyldiphenylsilyloxy)-2-methyloct-5-en-4-ylcarbamate (8a). The synthesis of the title compound has already been described in Example 8 (compound 4).

(S,E)-Benzyl 8-(tert-butyldiphenylsilyloxy)-2-methyloct-5-en-4-ylcarbamate (8b). To a mixture of the amine 7 (1.50 g, 3.79 mmol) in dry THF (15 mL) were added Et$_3$N (1.65 mL, 11.75 mmol), and then a solution of benzyl chloroformate (CbzCl, 0.59 mL, 4.17 mmol) in dry THF (4 mL) at 0° C. The resulting white suspension was allowed to warm to rt and stirred for 5 h, then diluted with DCM and water. The aqueous phase was extracted with DCM (2×), and the combined organic layers were washed with 10% HCl and sat. NaHCO$_3$, dried (MgSO$_4$), filtered and concentrated in vacuo. Flash chromatography (SiO$_2$, 8:2, hexanes/EtOAc) afforded 1.45 g (72%) of the title compound as a yellow oil. $^1$H NMR (300 MHz, CDCl$_3$) δ 7.75-7.65 (m, 4 H), 7.50-7.28 (m, 11 H), 5.70-5.55 (m, 1H), 5.40 (dd, 1 H, J=15.4, 6.2 Hz), 5.11 (s, 2 H), 4.58 (m, 1 H), 4.21 (m, 1 H), 3.71 (t, 2 H, J=6.6 Hz), 2.30 (q, 2 H, J=6.6 Hz), 1.67 (m, 1 H), 1.40-1.22 (m, 2 H), 1.07 (s, 9 H), 0.92 (m, 6 H); HRMS (ESI) m/z calcd for C$_{33}$H$_{43}$NO$_3$SiNa 552.2910, found 552.2930.

(S,E)-N-(8-(tert-Butyldiphenylsilyloxy)-2-methyloct-5-en-4-yl)-P,P-diphenylphosphinic amide (8c). To a solution of the amine 7 (400 mg, 1.01 mmol) in dry DCM (7 mL) were added Et$_3$N (0.44 mL, 3.13 mmol), and then a solution of diphenylphosphinic chloride (Ph$_2$POCl, 0.22 mL, 1.11 mmol) in dry DCM (3 mL) at 0° C. After being stirred at 0° C. for 15 min, the reaction mixture was allowed to warm to rt and stirred for 4 h, then diluted with DCM and 10% HCl. The aqueous phase was extracted with DCM and the combined organic layers were washed with sat. NaHCO$_3$, dried (MgSO$_4$), filtered and concentrated in vacuo to afford 720 mg of the crude title compound as a pale yellow solidified oil, which was used for the next step without further purification.

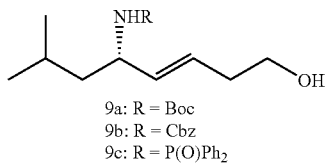

9a: R = Boc
9b: R = Cbz
9c: R = P(O)Ph$_2$ (S,E)-tert-Butyl 8-hydroxy-2-methyloct-5-en-4-ylcarbamate (9a). The synthesis of the title compound has already been described in Example 8 (compound 5).

(S,E)-Benzyl 8-hydroxy-2-methyloct-5-en-4-ylcarbamate (9b). To a solution of the TBDPS-protected alcohol 8b (584 mg, 1.10 mmol, crude) in dry THF (9 mL) at 0° C. was added TBAF (1.0M/THF, 1.38 mL, 1.38 mmol), and the reaction mixture was allowed to warm to rt while stirring under argon for 3.5 h, then quenched with sat. aq. NH$_4$Cl and diluted with EtOAc. The aqueous phase was separated and extracted with EtOAc. The combined organic layers were washed with brine, dried (Na$_2$SO$_4$), filtered and concentrated in vacuo. Flash chromatography (SiO$_2$, 5:5, hexanes/EtOAc) afforded 194 mg (60%, 2 steps) of the title compound as a colorless oil. [α]$_D^{23}$ −6.4 (c 1.0, DCM); $^1$H NMR (300 MHz, CDCl$_3$) δ 7.20-7.40 (m, 5 H), 5.65-5.49 (m, 1 H), 5.44 (dd, 1 H, J=15.3, 6.6 Hz), 5.09 (s, 2 H), 4.67 (bs, 1 H), 4.16 (m, 1 H), 3.63 (bs, 2 H), 2.28 (q, 2 H, J=6.0 Hz), 1.82 (bs, 1 H), 1.65 (m, 1 H), 1.40-1.25 (m, 2 H), 0.80-1.00 (m, 6 H); HRMS (ESI) m/z calcd for C$_{17}$H$_{25}$NO$_3$Na 314.1732, found 314.1739.

(S,E)-N-(8-Hydroxy-2-methyloct-5-en-4-yl)-P,P-diphenylphosphinic amide (9c). To a solution of the TBDPS-protected alcohol 8c (700 mg, 0.983 mmol, crude) in dry THF (8 mL) at 0° C. was added TBAF (1.0M/THF, 1.23 mL, 1.23 mmol), and the reaction mixture was allowed to warm to rt while stirring under argon. As completion was not reached after 4 h, 0.75 eq of TBAF (0.75 mL) was added at 0° C. The reaction mixture was stirred further at rt for 3 h, then quenched with sat. aq. NH$_4$Cl and diluted with EtOAc. The aqueous phase was separated and extracted with EtOAc. The combined organic layers were washed with brine, dried (Na$_2$SO$_4$), filtered and concentrated in vacuo. Flash chromatography (SiO$_2$, 95:5, EtOAc/MeOH) afforded 272 mg (77%, 2 steps) of the title compound as a white solid. mp 124.0-124.2° C.; [α]$_D^{23}$ −12.1 (c 1.0, DCM); $^1$H NMR (300 MHz, CDCl$_3$) δ 8.00-7.83 (m, 4 H), 7.58-7.35 (m, 6 H), 5.52 (dd, 1 H, J=15.3, 9.0 Hz), 5.24 (m, 1 H), 4.58 (bs, 1 H), 3.78-3.47 (m, 3 H), 2.80 (appdd, 1 H, J=9.2, 3.8 Hz), 2.16 (m, 2 H), 1.68 (bs, 1 H), 1.55-1.43 (m, 1 H), 1.43-1.31 (m, 1 H), 0.87 (dd, 6 H, J=8.6, 6.4 Hz); HRMS (ESI) m/z calcd for C$_{21}$H$_{28}$NO$_2$PNa 380.1755, found 380.1725.

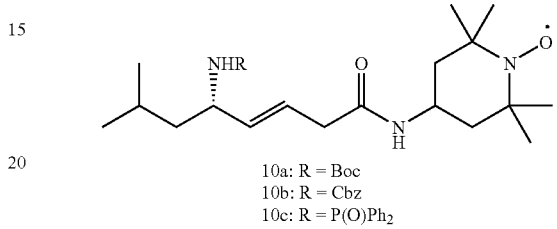

10a: R = Boc
10b: R = Cbz
10c: R = P(O)Ph$_2$

TEMPO-4-yl-(S,E)-5-(tert-butoxycarbonylamino)-7-methyloct-3-enamide (10a, JP4-039). The synthesis of the title compound has already been described in Example 8 (compound 7).

TEMPO-4-yl-(S,E)-5-(benzyloxycarbonylamino)-7-methyloct-3-enamide (10b). To a solution of the alcohol 9b (158 mg, 0.543 mmol) in acetone (5 mL) at 0° C. was added slowly a freshly prepared solution of Jones reagent (2.5M, 0.54 mL, 1.358 mmol). The resulting dark suspension was stirred at 0° C. for 1 h, then diluted with Et$_2$O and water. The aqueous phase was separated and extracted with Et$_2$O (2×). The combined organic layers were washed with water (2×) and brine (1×), dried (Na$_2$SO$_4$), filtered and concentrated in vacuo to yield 166 mg (quant.) of the crude acid as a slightly yellow oil, that was used for the next step without further purification.

To a solution of this acid (160 mg, 0.524 mmol, crude) in dry DCM (7 mL) at 0° C. were added successively a solution of 4-amino-TEMPO (139 mg, 0.786 mmol) in dry DCM (0.5 mL), DMAP (71 mg, 0.576 mmol), HOBt.H$_2$O (78 mg, 0.576 mmol) and EDCI (123 mg, 0.629 mmol). The resulting orange solution was stirred at rt under argon for 15 h, and then washed with sat. NH$_4$Cl. The aqueous phase was separated and extracted once with DCM, and the combined organic layers were dried (Na$_2$SO$_4$), filtered and concentrated in vacuo. Flash chromatography (SiO$_2$, 5:5 to 3:7, hexanes/EtOAc) afforded 171 mg (71%) of the title compound as a peach colored foam. mp 60.5° C. (softening point: 44° C.); [α]$_D^{23}$ +26.5 (c 0.5, DCM); EIMS m/z 458 ([M]$^+$, 37), 281 (19), 154 (28), 124 (47), 91 (100), 84 (41); HRMS (EI) m/z calcd for C$_{26}$H$_{40}$N$_3$O$_4$ 458.3019, found 458.3035.

TEMPO-4-yl-(S,E)-5-(diphenylphosphorylamino)-7-methyloct-3-enamide (10c). To a solution of the alcohol 9c (166.5 mg, 0.466 mmol) in acetone (5 mL) at 0° C. was slowly added a freshly prepared solution of Jones reagent (2.5M, 0.47 mL, 1.165 mmol). The resulting dark suspension was stirred at 0° C. for 2 h, then diluted with Et$_2$O and water. The aqueous phase was separated and extracted with Et$_2$O (2×). The combined organic layers were washed with water (2×) and brine (1×), dried (Na$_2$SO$_4$), filtered and concentrated in vacuo to yield 114 mg (66%) of the crude acid as a white foam, that was used for the next step without further purification.

To a solution of this acid (110 mg, 0.296 mmol, crude) in dry DCM (3.5 mL) at 0° C. were added successively a solution of 4-amino-TEMPO (78.4 mg, 0.444 mmol) in dry DCM (0.5 mL), DMAP (40.2 mg, 0.326 mmol), HOBt.H$_2$O (44.0 mg, 0.326 mmol) and EDCI (69.5 mg, 0.355 mmol). The resulting orange solution was stirred at rt under argon for 13 h, and then washed with sat. NH$_4$Cl. The aqueous phase was separated and extracted once with DCM, and the combined organic layers were dried (Na$_2$SO$_4$), filtered and concentrated in vacuo. Flash chromatography (SiO$_2$, EtOAc to 97:3, EtOAc/MeOH) afforded 91.2 mg (59%) of the title compound as an orange oil which solidified very slowly upon high vacuum. mp 168.0-168.8° C. (softening point: −75° C.); $[\alpha]_D^{23}$ −14.1 (c 0.5, DCM); EIMS m/z 525 ([M+H]$^+$, 10), 371 (27), 218 (28), 201 (74), 124 (100), 91 (35), 84 (26); HRMS (EI) m/z calcd for C$_{30}$H$_{43}$N$_3$O$_3$P 524.3042, found 524.3040.

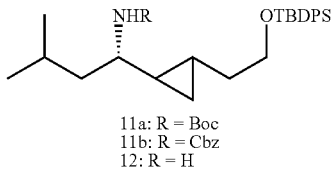

11a: R = Boc
11b: R = Cbz
12: R = H

Benzyl(1S)-1-(2-(2-(tert-butyldiphenylsilyloxy)ethyl)cyclopropyl)-3-methylbutylcarbamate (11b). To a solution of ZnEt$_2$ (110 mg, 0.844 mmol) in dry DCM (2 mL) was added DME (distilled, 0.088 mL, 844 mmol). The reaction mixture was stirred at rt for 10 min under N$_2$, then cooled to −20° C. and CH$_2$I$_2$ (0.137 mL, 1.687 mmol) was added dropwise over 4 min. After stirring for 10 min, a solution of the alkene 8b (149 mg, 0.281 mmol) in dry DCM (1 mL) was added dropwise over 5 min. The reaction mixture was allowed to warm to rt while stirring. After 10 h, the reaction mixture was quenched with sat. aq. NH$_4$Cl and diluted with DCM and water, the aqueous phase was separated and extracted with EtOAc. The combined organic layers were dried (Na$_2$SO$_4$), filtered and concentrated in vacuo. Flash chromatography (SiO$_2$, 9:1, hexanes/Et$_2$O) afforded 785 mg (68%) of the title compound as a colorless oil. $^1$H NMR analysis showed only 1 diastereomer (>95:5 dr). $[\alpha]_D^{23}$ −26.8 (c 1.0, DCM); $^1$H NMR (300 MHz, CDCl$_3$) δ 7.73-7.66 (m, 4 H), 7.48-7.28 (m, 11H), 5.13-4.96 (m, 2 H), 4.62 (appbd, 1 H, J=8.4 Hz), 3.72 (appbt, 2 H, J=6.4 Hz), 3.21 (m, 1 H), 1.80-1.63 (m, 1 H), 1.60-1.25 (m, 4 H), 1.08 (s, 9 H), 0.92 (appd, 6 H, J=6.3 Hz), 0.79 (m, 1 H), 0.51 (m, 1 H), 0.40 (m, 1 H), 0.30 (m, 1 H); HRMS (ESI) m/z calcd for C$_{34}$H$_{45}$NO$_3$SiNa 566.3066, found 566.3103.

(1S)-1-(2-(2-(Tert-butyldiphenylsilyloxy)ethyl)cyclopropyl)-3-methylbutan-1-amine (12). A flask containing a solution of the Cbz-protected amine 11b (460 mg, 0.846 mmol) in a 5:1 MeOH/EtOAc mixture (12 mL) was purged and filled 3 times with argon, then 10% Pd/C (50 mg) was added. The flask was purged and filled 3 times with H$_2$, and the resulting black suspension was stirred at rt under H$_2$ (1 atm). Since the reaction did not reach completion after 3 h, an additional amount of 10% Pd/C (30 mg) was added and stirring under H$_2$ was continued for 5 h. The reaction mixture was then filtered through a pad of Celite, the Celite washed with MeOH and AcOEt, and the solution concentrated in vacuo to yield 317 mg (92%) of the crude title compound as a pale yellow oil, that was used for the next step without further purification.

Tert-butyl(1S)-1-(2-(2-(tert-butyldiphenylsilyloxy)ethyl) cyclopropyl)-3-methylbutylcarbamate (11a). To a solution of the amine 12 (309 mg, 0.755 mmol) in dry DCM (12 mL) was added Et$_3$N (0.21 mL, 0.153 mmol) and then Boc$_2$O (183 mg, 0.830 mmol) at 0° C. The reaction mixture was stirred at rt under N$_2$ for 28 h. The reaction was quenched with sat. aq. NH$_4$Cl and the aqueous phase extracted with DCM. The combined organic layers were dried (Na$_2$SO$_4$), filtered and concentrated in vacuo to yield 471 mg of the crude title compound as a colorless oil, that was used for the next step without further purification.

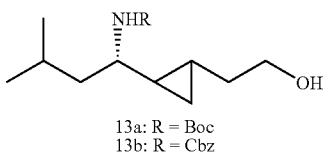

13a: R = Boc
13b: R = Cbz

Tert-butyl(1S)-1-(2-(2-hydroxyethyl)cyclopropyl)-3-methylbutylcarbamate (13a). To a solution of the crude TBDPS-protected alcohol 11a (464 mg, 0.742 mmol) in dry THF (6 mL) at 0° C. was added TBAF (1.0M/THF, 0.93 mL, 0.927 mmol), and the reaction mixture was allowed to warm to rt while stirring under N$_2$. Since TLC showed incomplete reaction after 5 h, 0.75 eq. TBAF (0.56 mL) was added. After 9 h, the reaction mixture was quenched with sat. aq. NH$_4$Cl and diluted with EtOAc. The aqueous phase was separated and extracted with EtOAc. The combined organic layers were washed with brine, dried (Na$_2$SO$_4$), filtered and concentrated in vacuo. Flash chromatography (SiO$_2$, 5:5, hexanes/EtOAc) afforded 177 mg (88%) of the title compound as a colorless oil which solidified upon high vacuum to give a white powder. mp 49.8-50.2° C.; $[\alpha]_D^{22}$ −30.8 (c 1.0, DCM); $^1$H NMR (300 MHz, CDCl$_3$) δ 4.50 (appbd, 1 H, J=4.5 Hz), 3.66 (bs, 2 H), 2.94 (m, 1 H), 2.36 (bs, 1H), 1.82 (bs, 1 H), 1.71 (m, 1 H), 1.45 (s, 9 H), 1.39 (t, 2 H, J=7.2 Hz), 1.01 (bs, 2 H), 0.90 (dd, 6 H, J=10.2, 6.6 Hz), 0.50 (m, 1 H), 0.43-0.27 (m, 2 H); HRMS (ESI) m/z calcd for C$_{15}$H$_{29}$NO$_3$Na 294.2045, found 294.2064.

Benzyl(1S)-1-(2-(2-hydroxyethyl)cyclopropyl)-3-methylbutylcarbamate (13b). To a solution of the TBDPS-protected alcohol 11b (320 mg, 0.588 mmol) in dry THF (5 mL) at 0° C. was added TBAF (1.0M/THF, 0.74 mL, 0.735 mmol), and the reaction mixture was allowed to warm to rt while stirring under argon for 7 h, then quenched with sat. aq. NH$_4$Cl and diluted with EtOAc. The aqueous phase was separated and extracted with EtOAc. The combined organic layers were washed with brine, dried (Na$_2$SO$_4$), filtered and concentrated in vacuo. Flash chromatography (SiO$_2$, 5:5, hexanes/EtOAc) afforded 166 mg (92%) of the title compound as a colorless oil. $[\alpha]_D^{23}$-21.6 (c 1.0, DCM); $^1$H NMR (300 MHz, CDCl$_3$) δ 7.42-7.28 (m, 5 H), 5.10 (m, 2 H), 4.76 (appbd, 1H, J=5.7 Hz), 3.63 (bs, 2 H), 3.04 (m, 1 H), 2.12-1.98 (bs, 1 H), 1.83-1.62 (m, 2 H), 1.42 (t, 2H, J=7.0 Hz), 1.16-0.95 (m, 2 H), 0.90 (appt, 6H, J=7.0 Hz), 0.53 (sept, 1H, J=4.3 Hz), 0.42 (dt, 1H, J=8.4, 4.5 Hz), 0.34 (dt, 1H, J=8.4, 5.0 Hz); HRMS (ESI) m/z calcd for C$_{18}$H$_{27}$NO$_3$Na 328.1889, found 328.1860.

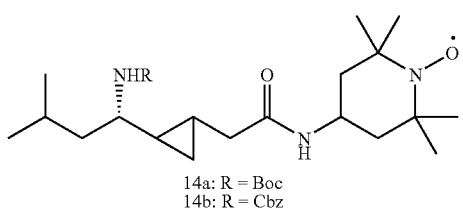

14a: R = Boc
14b: R = Cbz

TEMPO-4-yl-2-(2-((S)-1-(tert-butoxycarbonylamino)-3-methylbutyl)cyclopropyl)acetamide (14a). To a solution of the alcohol 13a (130 mg, 0.477 mmol) in acetone (5 mL) at 0° C. was slowly added a solution of Jones reagent (2.5M, 0.48 mL, 1.194 mmol). The resulting dark suspension was stirred at 0° C. for 1 h, then diluted with $Et_2O$ and water. The aqueous phase was separated and extracted with $Et_2O$ (2×). The combined organic layers were washed with water (2×) and brine (1×), dried ($Na_2SO_4$), filtered and concentrated in vacuo to yield 133 mg (97%) of the crude title compound as a colorless oil, that was used for the next step without further purification.

To a solution of this acid (127.6 mg, 0.447 mmol, crude) in dry DCM (5.5 mL) at 0° C. were added successively a solution of 4-amino-TEMPO (118.4 mg, 0.671 mmol) in dry DCM (0.5 mL), DMAP (60.7 mg, 0.492 mol), $HOBt·H_2O$ (66.4 mg, 0.492 mmol) and EDCI (105.0 mg, 0.536 mol). The resulting orange solution was stirred at rt under argon for 15 h, and then washed with sat. $NH_4Cl$. The aqueous phase was separated and extracted once with DCM, and the combined organic layers were dried ($Na_2SO_4$), filtered and concentrated in vacuo. Flash chromatography ($SiO_2$, 5:5 to 3:7, hexanes/EtOAc) afforded 150.0 mg (76%) of the title compound as a peach colored foam. mp 139.5° C.; $[\alpha]_D^{23}$ −15.7 (c 0.5, DCM); EIMS m/z 438 ($[M]^+$, 6), 252 (57), 140 (67), 124 (80), 91 (48), 84 (59), 57 (100); HRMS (EI) m/z calcd for $C_{24}H_{44}N_3O_4$ 438.3332, found 438.3352.

TEMPO-4-yl-2-(2-((S)-1-(benzyloxycarbonylamino)-3-methylbutyl)cyclopropyl)acetamide (14b). To a solution of the alcohol 13b (110.5 mg, 0.362 mol) in acetone (5 mL) at 0° C. was slowly added a solution of Jones reagent (2.5M, 0.36 mL, 0.904 mol). The resulting dark suspension was stirred at 0° C. for 1 h, then diluted with $Et_2O$ and water. The aqueous phase was separated and extracted with $Et_2O$ (2×). The combined organic layers were washed with water (2×) and brine (1×), dried ($Na_2SO_4$), filtered and concentrated in vacuo to yield 113.5 mg (98%) of the crude title compound as a colorless oil, that was used for the next step without further purification.

To a solution of this acid (110 mg, 0.344 mmol, crude) in dry DCM (4.5 mL) at 0° C. were added successively a solution of 4-amino-TEMPO (91.2 mg, 0.517 mmol) in dry DCM (0.5 mL), DMAP (46.7 mg, 0.379 mmol), $HOBt·H_2O$ (51.2 mg, 0.379 mmol) and EDCI (80.8 mg, 0.413 mmol). The resulting orange solution was stirred at rt under argon for 18 h, and then washed with sat. $NH_4Cl$. The aqueous phase was separated and extracted once with DCM, and the combined organic layers were dried ($Na_2SO_4$), filtered and concentrated in vacuo. Flash chromatography ($SiO_2$, 4:6, hexanes/EtOAc) afforded 123 mg (75%) of the title compound as a peach colored foam. mp 51.8° C. (softening point: 44° C.); $[\alpha]_D^{23}$ −15.3 (c 0.5, DCM); EIMS m/z 472 ($[M]^+$, 42), 415 (58), 322 (43), 168 (47), 140 (46), 124 (75), 91 (100), 84 (53); HRMS (EI) m/z calcd for $C_{27}H_{42}N_3O_4$ 472.3175, found 472.3165.

EXAMPLE 20

Synthesis of Alternative Nitroxide Moieties

Figure 42:
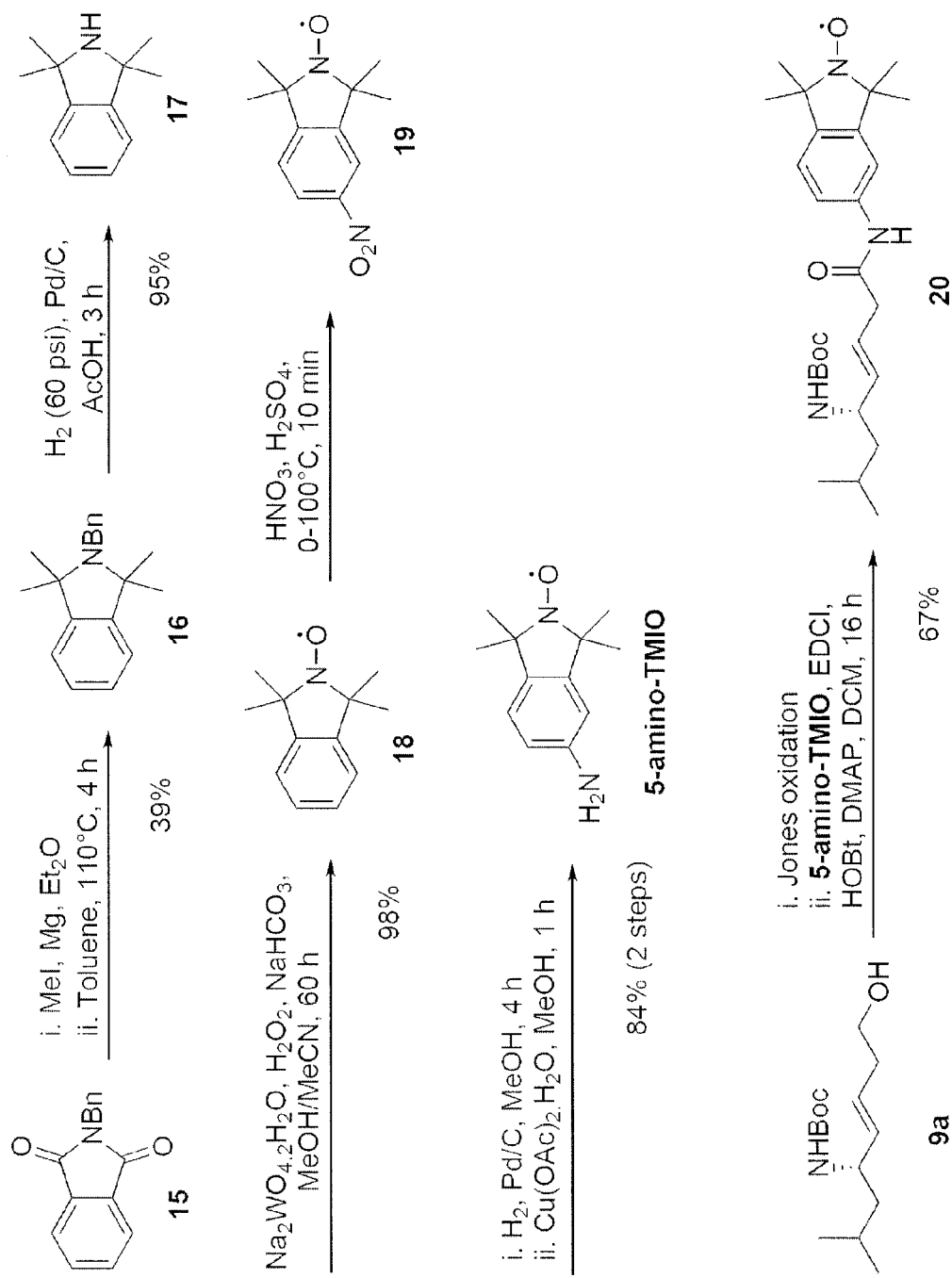
FIG. 42 is a schematic of a synthesis protocol for an alternative nitroxide moiety of 1,1,3,3-tetramethylisoindolin-2-yloxyl (TMIO).
Figure 43:
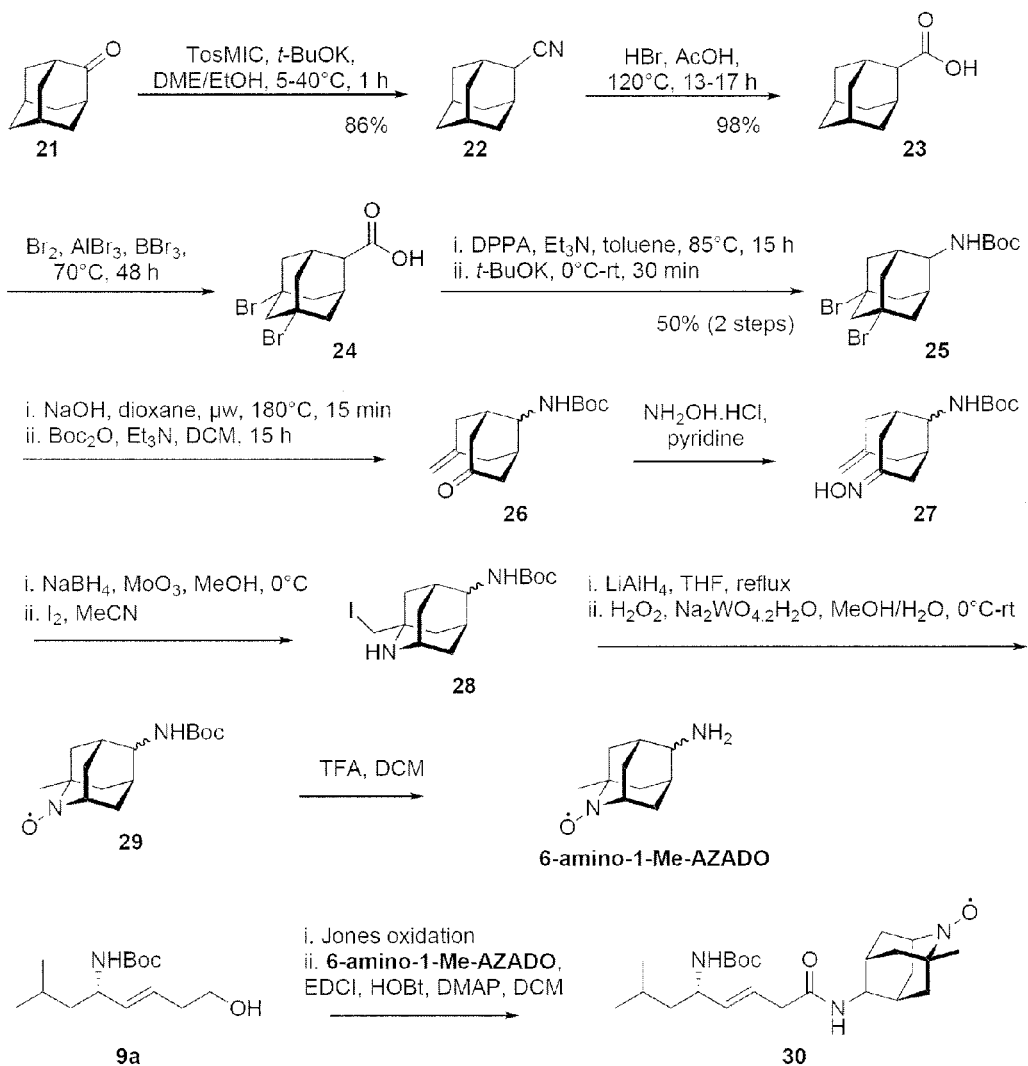
FIG. 43 is a schematic of a synthesis protocol for an alternative nitroxide moiety of 1-methyl 2-azaadamantane N-oxyl (1-Me-AZADO).

Schematics are shown for alternative nitroxide moieties, where FIG. 42 shows a synthesis protocol for 5-amino-1,1,3,3-tetramethylisoindolin-2-yloxyl (5-amino-TMIO) and FIG. 43 shows a synthesis protocol for 6-amino-1-methyl 2-azaadamantane N-oxyl (6-amino-1-Me-AZADO).

Compounds 5-amino-1,1,3,3-tetramethylisoindolin-2-yloxyl (5-amino-TMIO) and (20) are shown in FIG. 42 and were prepared according to the following.

Synthesis of 5-amino-TMIO was previously described by Reid, D. A. et al. (The synthesis of water soluble isoindoline nitroxides and a pronitroxide hydroxylamine hydrochloride UV-VIS probe for free radicals. *Chem. Comm.* 1998, 17, 1907-8) and references cited therein.

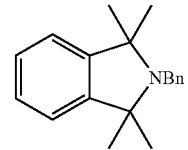

16

2-Benzyl-1,1,3,3-tetramethylisoindoline (16). (First step: *Org. Synth.* 1998, 9, 649; second step: Griffiths, P. G. et al. Synthesis of the radical scavenger 1,1,3,3-tetramethylisoindolin-2-yloxyl. *Aust. J. Chem.* 1983, 36, 397-401). An oven-dried 250 mL, three-necked, round-bottom flask was flushed with nitrogen, and magnesium turnings (3.84 g, 156.5 mmol) were introduced, that were covered with dry $Et_2O$ (9 mL). A solution of MeI (9.45 mL, 150.2 mmol) in dry $Et_2O$ (80 mL) was then added dropwise via a dropping funnel while stirring over a period of 50 min. The resulting reaction mixture was then stirred for an additional 30 min, and then concentrated by slow distillation of solvent until the internal temperature reached 80° C. The residue was allowed to cool to 60° C., and a solution of N-benzylphthalimide (6.00 g, 25.04 mmol) in dry toluene (76 mL) was added dropwise via a dropping funnel with stirring at a sufficient rate to maintain this temperature. When the addition was complete, solvent was distilled slowly from the mixture until the temperature reached 108-110° C. The reaction mixture was refluxed at 110° C. for 4 h, then concentrated again by further solvent distillation. It was then cooled and diluted with hexanes (turned purple). The resulting slurry was filtered through Celite and washed with hexanes. The combined yellow filtrate turned dark red-purple after standing in air overnight. It was then concentrated in vacuo. The resulting purple residue was passed through a short column of basic alumina (grade I, 70-230 mesh), eluting with hexanes (~1 L), to afford 2.585 g (39%) of the title compound as a colorless oil which solidified to give a white solid. mp 61.0-61.4° C. $^1$H NMR (300 MHz, $CDCl_3$) δ 7.48 (appd, 2 H, J=7.2 Hz), 7.34-7.19 (m, 5 H), 7.18-7.11 (m, 2 H), 4.00 (s, 2 H), 1.31 (s, 12 H); HRMS (EI) m/z calcd for $C_{19}H_{23}N$ 265.1830, found 265.1824.

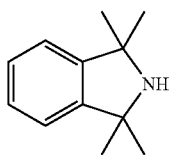

17

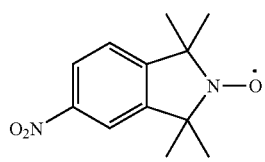

19

1,1,3,3-Tetramethylisoindoline (17). (Griffiths, P. G. et al Synthesis of the radical scavenger 1,1,3,3-tetramethylisoindolin-2-yloxyl. *Aust. J. Chem.* 1983, 36, 397-401; Chan, K. S. et al. Reactions of nitroxides with metalloporphyrin alkyls bearing beta hydrogens: aliphatic carbon-carbon bond activation by metal centered radicals. *J. Organomet. Chem.* 2008, 693, 399-407). The protected benzyl-amine 16 (1.864 g, 7.02 mmol) was dissolved in AcOH (34 mL) in a Parr flask, and 10% Pd/C (169.5 mg) was added. (The reaction was splited in 3 batches.) The flask was placed in a high pressure reactor. The reactor was charged with $H_2$ and purged for 5 cycles and was finally pressurized with $H_2$ at 4 bars (60 psi). After stirring at rt for 3 h, the reaction mixture was filtered through Celite, and the solvent removed in vacuo. The resulting residue was dissolved in water (5 mL) and the solution neutralized with 2.5N NaOH (pH 11.5), and extracted with $Et_2O$ (3×50 mL). The combined organic layers were dried ($Na_2SO_4$), filtered and concentrated in vacuo to yield 1.165 g (95%) of the crude title compound as slightly yellow crystals. mp 36.0-36.5° C. $^1H$ NMR (300 MHz, $CDCl_3$) δ 7.30-7.23 (m, 2 H), 7.18-7.11 (m, 2 H), 1.86 (bs, 1 H), 1.48 (s, 12 H).

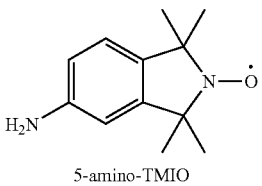

18

1,1,3,3-Tetramethylisoindolin-2-yloxyl (18). (Griffiths, P. G. et al. Synthesis of the radical scavenger 1,1,3,3-tetramethylisoindolin-2-yloxyl. *Aust. J. Chem.* 1983, 36, 397-401; Chan, K. S. et al. Reactions of nitroxides with metalloporphyrin alkyls bearing beta hydrogens: aliphatic carbon-carbon bond activation by metal centered radicals. *J. Organomet. Chem.* 2008, 693, 399-407). To a solution of the amine 17 (1.46 g, 8.33 mmol) in a 14:1 mixture of MeOH/MeCN (16.6 mL) were added successively $NaHCO_3$ (560 mg, 6.67 mmol), $Na_2WO_4 \cdot 2H_2O$ (83.3 mg, 0.25 mmol) and 30% aq. $H_2O_2$ (3.12 mL, 27.50 mmol). The resulting suspension was stirred at rt. After 18 h, a bright yellow suspension formed and 30% aq. $H_2O_2$ (3.00 mL, 26.44 mmol) was added. The reaction mixture was stirred for 2 days, then diluted with water and extracted with hexanes (2×). The combined organic layers were washed with 1M $H_2SO_4$ and brine, dried ($Na_2SO_4$), filtered and concentrated in vacuo to yield 1.55 g (98% crude) of the title compound as a yellow crystalline powder, that was used for the next step without further purification. mp 122-125° C. (softening point: 108° C.); HRMS (EI) m/z calcd for $C_{12}H_{17}NO$ 191.1310, found 191.1306.

5-Nitro-1,1,3,3-tetramethylisoindolin-2-yloxyl (19). (Bolton, R. et al. An EPR and NMR study of some tetramethyl-isoindolin-2-yloxyl free radicals. *J. Chem. Soc. Perkin Trans. 2*, 1993, 2049-52). Conc. $H_2SO_4$ (13.5 mL) was added dropwise to 18 (1.345 g, 7.07 mmol) cooled in an ice-water bath, forming a dark-red solution which was then warmed to 60° C. for 15 min and then cooled to 0° C. Conc. $HNO_3$ (0.90 mL, 19.09 mmol) was added dropwise. When the reaction appeared complete, the yellow-orange solution was heated at 100° C. for 10 min, the color turning to red-orange. After cooling to rt, the reaction mixture was neutralized by careful addition to ice-cooled 2.5N NaOH (30 mL). This aqueous phase was extracted with $Et_2O$ until it became colorless and the combined organic layers were dried ($Na_2SO_4$), filtered and concentrated in vacuo to yield 1.64 g (98%) of the crude title compound as a yellow-orange powder, that was used for the next step without further purification.

5-amino-TMIO 5-amino-1,1,3,3-tetramethylisoindolin-2-yloxyl (5-amino-TMIO). (First step: Reid, D. A. et al. The synthesis of water soluble isoindoline nitroxides and a pronitroxide hydroxylamine hydrochloride UV-VIS probe for free radicals. *Chem. Comm.* 1998, 17,1907-8; Giroud, A. M. and Rassat, A. Nitroxydes LXXX: syntheses de mono et biradicaux nitroxydes derives de l'isoindoline. *Bull. Soc. Chim. Fr.* 1979, *II*, 48-55; second step: Keana, J. F. W. and Lee, T. D. Versatile synthesis of doxyl spin labels bypassing the usual ketone precursors. *J. Am. Chem. Soc.* 1975, 97, 1273-4). A flask containing a solution of 19 (1.50 g, 6.38 mmol, crude) in MeOH (75 mL) was purged and filled with argon, then 10% Pd/C (150 mg) was added. The flask was purged and filled 3 times with $H_2$, and the resulting black suspension was stirred at rt under $H_2$ (1 atm) for 4 h. The reaction mixture was then filtered through Celite, the Celite washed with MeOH, and the solution concentrated in vacuo to yield 1.38 g of the crude title compound as a yellow solid, that was used for the next step without further purification. $^1H$ NMR (300 MHz, $CD_3OD$) δ 6.89 (d, 1 H, J=8.1 Hz), 6.25 (dd, 1 H, J=8.1, 2.1 Hz), 6.54 (d, 1 H, J=2.1 Hz), 3.35 (s, 2 H), 1.34 (appd, 12 H, J=5.7 Hz).

To a solution of the crude hydroxylamine (1.38 g, 6.38 mmol) in MeOH (75 mL) was added $Cu(OAc)_2 \cdot H_2O$ (26 mg, 0.128 mmol). The reaction mixture was stirred at rt under air for 1.5 h, the color turning to dark brown. The solvent was then removed in vacuo, the residue taken up in $CHCl_3$ and a small amount of MeOH to dissolve the insoluble material, and washed with water. The aqueous phase was extracted twice with $CHCl_3$, and the combined organic layers were washed with brine, dried ($Na_2SO_4$), filtered and concentrated

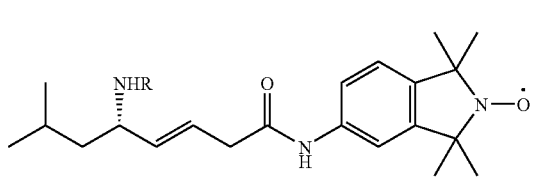

TMIO-5-yl-(S,E)-5-(tert-butoxycarbonylamino)-7-methyloct-3-enamide (20). To a solution of the alcohol 9a (187 mg, 0.728 mmol, prepared according to previous examples) in acetone (7 mL) at 0° C. was slowly added a solution of Jones reagent (2.5M, 0.73 mL, 1.821 mmol). The resulting dark suspension was stirred at 0° C. for 1 h, then diluted with Et$_2$O and water. The aqueous phase was separated and extracted with Et$_2$O (2×). The combined organic layers were washed with water (2×) and brine (1×), dried (Na$_2$SO$_4$), filtered and concentrated in vacuo to yield 190 mg (96%) of the crude title compound as a slightly yellow oil, that was used for the next step without further purification.

To a solution of this acid (187.4 mg, 0.691 mmol, crude) in dry DCM (8 mL) at 0° C. were added successively 5-amino-TMIO (212.6 mg, 1.036 mmol), DMAP (93.7 mg, 0.760 mmol), HOBt.H$_2$O (102.6 mg, 0.760 mmol) and EDCI (162.1 mg, 0.829 mmol). The resulting yellowish solution was stirred at rt under argon for 16 h, and then washed with sat. NH$_4$Cl. The aqueous phase was separated and extracted once with DCM, and the combined organic layers were washed twice with 1N HCl and once with sat. NaHCO$_3$, dried (Na$_2$SO$_4$), filtered and concentrated in vacuo. Flash chromatography (SiO$_2$, 6:4, hexanes/EtOAc) afforded 221.0 mg (70%) of the title compound as a pale orange foam. mp 78-79° C. (softening point: 70° C.); [α]$_D^{22}$ +72.2 (c 0.5, DCM); ESIMS m/z 481 ([M+Na]$^+$, 50), 939 ([2M+Na]$^+$, 100).

Compound 6-amino-1-methyl 2-azaadamantane N-oxyl (6-amino-1-Me-AZADO) and (30) are shown in FIG. 43 and were prepared according to the following.

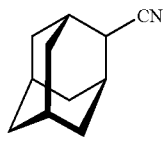

2-Adamantanecarbonitrile (tricyclo[3.3.1.1$^{3,7}$]decane-2-carbonitrile, 22). (Oldenziel, O. H. et al. 2-Adamantanecarbonitrile. *Org. Synth.* 1977, 57, 8; Rohde, J. J. et al. Discovery and Metabolic Stabilization of Potent and Selective 2-Amino-N-(adamant-2-yl) Acetamide 11β-Hydroxysteroid Dehydrogenase Type 1 Inhibitors. *J. Med. Chem.* 2007, 50, 149-64). A 3-5° C. solution of 2-adamantanone (tricyclo [3.3.1.1$^{3,7}$]decan-2-one, 21) (21.0 g, 137 mmol), p-tolylsulfonylmethyl isocyanide (TosMIC, 35.5 g, 178 mmol) and EtOH (14 mL, 233 mmol) in 1,2-dimethoxyethane (DME, 470 mL) was treated with portionwise addition of solid t-BuOK (39.2 g, 342 mmol), maintaining the internal temperature below 10° C. After the addition, the resulting slurry reaction mixture was stirred at rt for 30 min and then at 35-40° C. for 30 min. The heterogeneous reaction mixture was filtered and the solid washed with DME. The filtrate was concentrated in vacuo, loaded to a short Al$_2$O$_3$ column (activated, neutral, Brockmann 1,150 mesh, 7 cm thick×15 cm height), and washed off with a 5:1 mixture of hexanes/DCM (~1.5 L). The solution was concentrated in vacuo to afford 19.0 g (86%) of the title compound as a white powder. $^1$H NMR (300 MHz, CDCl$_3$) δ 2.91 (s, 1 H), 2.23-2.08 (m, 4 H), 2.00-1.80 (m, 4 H), 1.80-1.66 (m, 6 H).

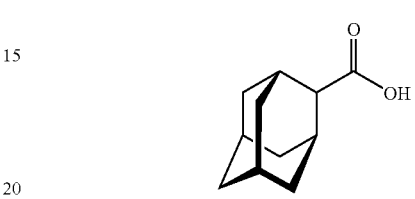

2-Adamantane carboxylic acid (23). (Rohde, J. J. et al. Discovery and Metabolic Stabilization of Potent and Selective 2-Amino-N-(adamant-2-yl) Acetamide 11β-Hydroxysteroid Dehydrogenase Type 1 Inhibitors. *J. Med. Chem.* 2007, 50, 149-64). A mixture of the nitrile 22 (18.9 g, 117 mmol) in AcOH (56 mL) and 48% HBr (224 mL) was stirred at 120° C. overnight. The reaction mixture was cooled at 4° C., standing for 4 h, then filtered. The solid was washed with water and dried in vacuum over silica gel overnight, to yield 20.6 g (98%) of the title compound as off-white crystals. $^1$H NMR (300 MHz, DMSO-d$_6$) δ 12.09 (s, 1 H), 2.55-2.47 (m, 1 H), 2.20 (bs, 2 H), 1.87-1.64 (m, 10 H), 1.60-1.50 (m, 2 H).

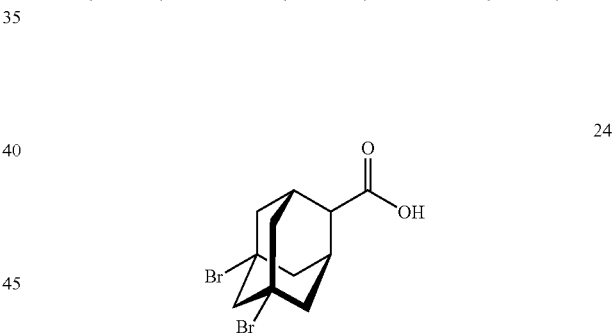

5,7-Dibromo-2-adamantane carboxylic acid (24). (Adapted from Rohde, J. J. et al. Discovery and Metabolic Stabilization of Potent and Selective 2-Amino-N-(adamant-2-yl) Acetamide 11-Hydroxysteroid Dehydrogenase Type 1 Inhibitors. *J. Med. Chem.* 2007, 50, 149-64). A vigorously stirred 0° C. solution of AlBr$_3$ (18.9 g, 69.6 mmol), BBr$_3$ (2.40 g, 9.49 mmol) and Br$_2$ (40 mL) was treated portionwise with the acid 23 (5.70 g, 31.6 mmol). Upon completion of the addition, the reaction mixture was stirred at 70° C. for 48 h, then cooled in an ice bath, and quenched carefully with sat. sodium bisulfite. Stirring was continued at rt overnight. The resultant pale brown suspension was filtered, the solid washed with water and dried overnight under vacuum at 60° C. to yield 10.95 g (quant.) of the crude title compound as a beige powder. $^1$H NMR (300 MHz, DMSO-d$_6$) δ 12.56 (bs, 0.3 H), 2.85 (appd, 2 H, J=12.9 Hz), 2.75-2.55 (m, 2 H), 2.50-2.35 (m, 2 H), 2.35-2.10 (m, 7 H).

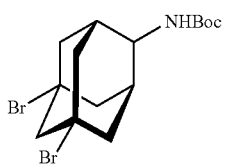

25

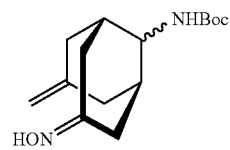

27

(5,7-Dibromo-adamantan-2-yl)-carbamic acid tert-butyl ester (25). A suspension of the acid 24 (2.00 g, 5.92 mmol) in dry toluene (30 mL) was treated successively with Et$_3$N (1.0 mL, 7.10 mmol) and diphenylphosphoryl azide (DPPA, 1.6 mL, 7.10 mmol). The resulting mixture was stirred at 85° C. for 15 h. To a separated flask containing a solution of t-BuOK (1.35 g, 11.8 mmol) in dry THF (80 mL) at 0° C. was added the isocyanate solution dropwise via a dropping funnel. The resulting reaction mixture was allowed to warm to rt over 30 min, and then it was quenched with water. The THF was removed in vacuo, and the resulting material was diluted with EtOAc. The organic layer was washed with 1N HCl, sat. NaHCO$_3$ and brine, dried (Na$_2$SO$_4$), filtered and concentrated in vacuo. Flash chromatography (SiO$_2$, 95:5 to 8:2, hexanes/EtOAc) afforded 1.20 g (50%, 2 steps) of the title compound as a white powder. $^1$H NMR (300 MHz, CDCl$_3$) δ4.68 (bs, 1 H), 3.76 (bs, 1 H), 2.87 (s, 2 H), 2.47-2.13 (m, 10 H), 1.46 (s, 9 H).

(7-Methylene-bicyclo[3.3.1]nonan-3-one oxime-9-yl)-carbamic acid tert-butyl ester (27). To a solution of ketone 26 (137 mg, 0.515 mmol) in dry pyridine (1 mL) was added NH$_2$OH.HCl (109 mg, 1.54 mmol). The reaction mixture was stirred at rt under argon for 23 h. The solvent was then removed in vacuo, and the residue was diluted with EtOAc and then water was added. The layers were separated and the aqueous phase extracted with EtOAc. The combined organic layers were washed with 5% aq. CuSO$_4$ (3×), brine (1×), dried (Na$_2$SO$_4$), filtered and concentrated in vacuo. Flash chromatography (SiO$_2$, 4:6, hexanes/EtOAc) afforded 133 mg (92%) of the title compound as a colorless gum. $^1$H NMR (300 MHz, CDCl$_3$) δ 7.02 (bs, 0.6 H), 4.90 (bs, 0.25 H), 4.80 (d, 1 H, J=2.1 Hz), 4.76 (bs, 0.75 H), 4.69 (d, 1 H, J=2.1 Hz), 3.87 (bs, 1 H), 3.26 (d, 0.25 H, J=16.8 Hz), 3.11 (d, 0.75 H, J=16.8 Hz), 2.55-2.48 (m, 4 H), 2.48-2.20 (m, 4 H), 2.16 (appd, 0.25 H, J=17.1 Hz), 2.04 (dd, 0.75 H, J=17.1, 5.4 Hz), 1.47 (s, 9 H).

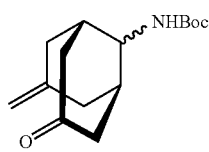

26

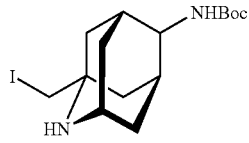

28

(7-Methylene-bicyclo[3.3.1]nonan-3-one-9-yl)-carbamic acid tert-butyl ester (26). (First step: Rohde, J. J. et al. Discovery and Metabolic Stabilization of Potent and Selective 2-Amino-N-(adamant-2-yl) Acetamide 11β-Hydroxysteroid Dehydrogenase Type 1 Inhibitors. *J. Med. Chem.* 2007, 50, 149-64). A solution of 25 (125 mg, 0.305 mmol) in dioxane (0.80 mL) was treated with 2N NaOH (0.70 mL, 1.37 mmol) and irradiated under microwaves (µw, Biotage) for 15 min at 180° C. The dioxane was removed in vacuo. The residue was dissolved in DCM, washed with water, dried (Na$_2$SO$_4$), filtered and concentrated in vacuo to afford 82.5 mg of crude 9-amino-7-methylene-bicyclo[3.3.1]nonan-3-one as a yellow oil, that was used for the next step without further purification.

To a solution of this crude amine in dry DCM (5 mL) was added Et$_3$N (0.13 mL, 0.913 mmol) and then Boc$_2$O (73.8 mg, 0.335 mmol) at 0° C. The reaction mixture was stirred at rt under N$_2$ for 14 h. The reaction was quenched with sat. aq. NH$_4$Cl and the aqueous phase extracted twice with DCM. The combined organic layers were dried (Na$_2$SO$_4$), filtered and concentrated in vacuo. Flash chromatography (SiO$_2$, 7:3, hexanes/EtOAc) afforded 48.0 mg (59%, 2 steps) of the title compound as a white powder. $^1$H NMR (300 MHz, CDCl$_3$) δ 4.93 (bs, 0.25 H), 4.84 (s, 2 H), 4.81 (bs, 0.75 H), 4.12 (bs, 0.25 H), 3.91 (appbd, 0.75 H, J=3.6 Hz), 2.64-2.37 (m, 6 H), 2.37-2.23 (m, 3.25 H), 2.17 (appbd, 0.75 H, J=13.8 Hz), 1.48 and 1.46 (2 s, 9 H).

(1-Iodomethyl-2-azaadamantan-6-yl)-carbamic acid tert-butyl ester (28). To a mixture of oxime 27 (130 mg, 0.464 mmol) and MoO$_3$ (94 mg, 0.649 mmol) in dry MeOH (4.6 mL) at 0° C. under argon was added NaBH$_4$ (179 mg, 4.64 mmol) portionwise. The reaction mixture was stirred at 0° C., and 2 additional amounts of NaBH$_4$ (179 mg, 4.64 mmol) were added portionwise after 2.5 h and after 5.5 h. After 7 h, the dark brown reaction mixture was quenched with acetone and then filtered through Celite, and the Celite rinsed with acetone. The filtrate was concentrated in vacuo. The resulting residue was diluted with water and extracted twice with EtOAc. The combined organic layers were washed with brine, dried (K$_2$CO$_3$), filtered and concentrated in vacuo to afford 136 mg of the crude amine as a yellow oil, that was used for the next step without further purification.

To a suspension of this crude amine in dry acetonitrile (MeCN, 2.3 mL) at 0° C. under argon was added 12 (117 mg, 0.462 mmol). The reaction mixture was allowed to stir at rt for 4 h and then quenched with sat. NaHCO$_3$ and sat. Na$_2$S$_2$O$_3$. The resulting mixture was extracted twice with DCM/CHCl$_3$, and the organic layer was dried (K$_2$CO$_3$), filtered and concentrated in vacuo. Flash chromatography (SiO$_2$, 95:5 to 9:1, DCM/MeOH) afforded 76.5 mg (42%) of the title compound as a brown oil. $^1$H NMR (300 MHz, CDCl$_3$) δ 4.83 (bs, 1 H), 3.77 (bs, 1 H), 3.30 (bs, 1H), 3.24 (apps, 2 H), 2.14 (appbs, 2 H), 1.94 (appbd, 2 H, J=13.5 Hz), 1.75 (m, 6 H), 1.46 (s, 9H).

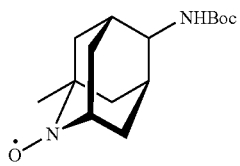

(1-Methyl-2-azaadamantane-N-oxyl-6-yl)-carbamic acid tert-butyl ester (29). Deiodination of the amine 28 can be achieved by treating 28 with a reducing agent, such as LiAlH$_4$ or NaBH$_4$, possibly in the presence of a catalyst, such as InCl$_3$, and in a polar aprotic solvent such as THF or MeCN.

Oxidation of the resulting amine to afford the corresponding nitroxide 29 can be achieved by treating the said amine with H$_2$O$_2$ in the presence of a catalytic amount of Na$_2$WO$_4$.2H$_2$O, in a solvent mixture of MeOH and H$_2$O.

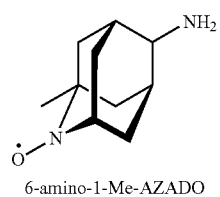

6-amino-1-Me-AZADO

6-Amino-1-methyl-2-azaadamantane-N-oxyl (6-amino-1-Me-AZADO). Cleavage of the Boc-protecting group can be achieved by treating the protected amine 29 with trifluoroacetic acid (TFA) in DCM, to afford the free amine 6-amino-1-Me-AZADO.

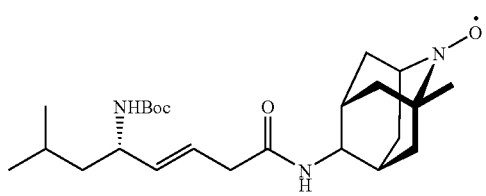

(1-Me-AZADO-6-yl)-(S,E)-5-(tert-butoxycarbonylamino)-7-methyloct-3-enamide (30). Jones oxidation of (S,E)-tert-butyl 8-hydroxy-2-methyloct-5-en-4-ylcarbamate (9a) affords the corresponding acid as described above. Compound (9a) is prepared according to previous examples.

Amide coupling of the said acid with 6-amino-1-Me-AZADO is achieved following the conditions described above, using the coupling agents EDCI, DMAP, and HOBt-hydrate in CH$_2$Cl$_2$ (DCM), to yield compound (30).

Whereas particular embodiments of this invention have been described above for purposes of illustration, it will be evident to those skilled in the art that numerous variations of the details of the present invention may be made without departing from the invention as defined in the appended claims.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

We claim:

1. A compound having the structure:

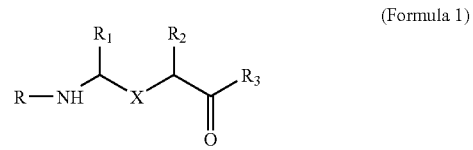

(Formula 1)

wherein X is one of

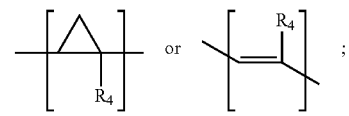

$R_1$ and $R_2$ are hydrogen, $C_1$-$C_6$ straight or branched-chain alkyl, or a $C_1$-$C_6$ straight or branched-chain alkyl further comprising a phenyl ($C_6H_5$) group, that is unsubstituted or is methyl-, hydroxyl- or fluoro-substituted; $R_4$ is hydrogen, $C_1$-$C_6$ straight or branched-chain alkyl, or a $C_1$-$C_6$ straight or branched-chain alkyl further comprising a phenyl ($C_6H_5$) group, that is unsubstituted or is methyl-, hydroxyl- or fluoro-substituted; $R_3$ is —NH—$R_5$; R is —C(O)—$R_6$, —C(O)O—$R_6$, or —P(O)—($R_6$)$_2$, wherein $R_6$ is $C_1$-$C_6$ straight or branched-chain alkyl or $C_1$-$C_6$ straight or branched-chain alkyl further comprising one or more phenyl (—$C_6H_5$) groups that are independently unsubstituted, or methyl-, ethyl-, hydroxyl- or fluoro-substituted; $R_5$ has the structure

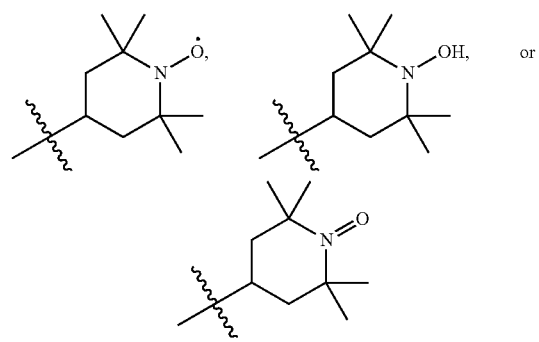

and wherein the compound is not XJB-5-208.

2. The compound of claim 1, having the structure

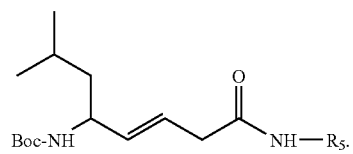

3. The compound of claim 2, having the structure

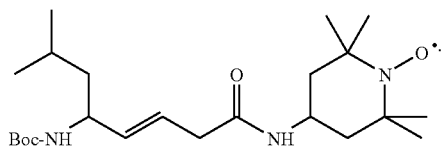

4. The compound of claim 3, having the structure

JP4-039

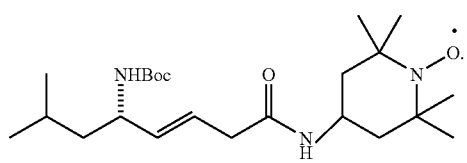

5. The compound of claim 1, in which R is Ac, Boc, Cbz, or —P(O)-Ph$_2$.

6. The compound of claim 1, in which R$_1$, R$_2$, R$_4$ and R$_6$ are independently chosen from hydrogen, methyl, ethyl, propyl, 2-propyl, butyl, t-butyl, pentyl, hexyl, benzyl, and hydroxybenzyl.

7. The compound of claim 1, wherein when X is —CH=CR$_4$—, R$_4$ is hydrogen, methyl or ethyl.

8. The compound of claim 1, having the structure:

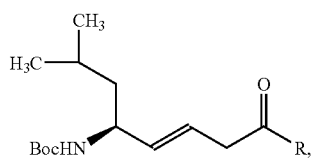

9. The compound of claim 1, wherein X is

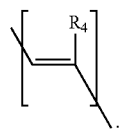

10. The compound of claim 9, in which R is Ac, Boc, Cbz, or —P(O)-Ph$_2$.

11. The compound of claim 9 in which R$_1$, R$_2$ and R$_4$ independently are methyl, ethyl, propyl, 2-propyl, butyl, t-butyl, pentyl, hexyl, benzyl, and hydroxybenzyl.

12. The compound of claim 9 having a structure chosen from

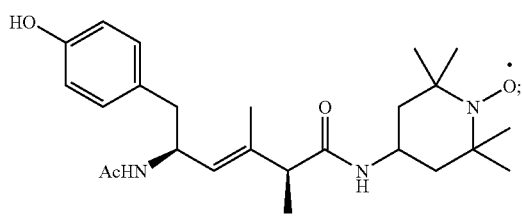

A1

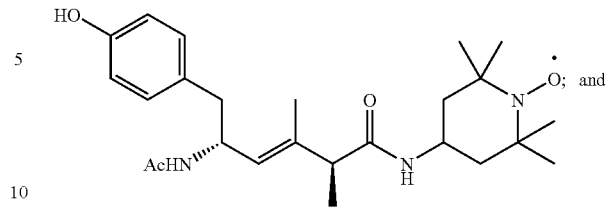
A2

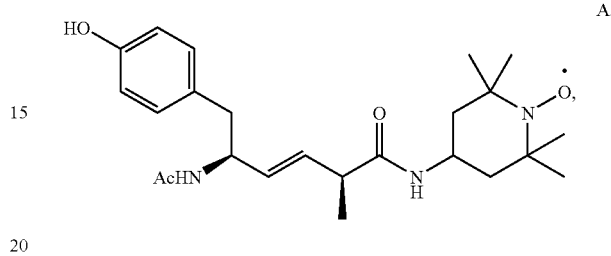
A3 wherein Ac is acetyl.

13. The compound of claim 1 wherein X is

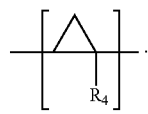

14. The compound of claim 13, in which R is Ac, Boc, Cbz, or —P(O)-Ph$_2$.

15. The compound of claim 13, in which R$_1$, R$_2$ and R$_4$ independently are methyl, ethyl, propyl, 2-propyl, butyl, t-butyl, pentyl, hexyl, benzyl, and hydroxybenzyl.

16. The compound of claim 13, having a structure chosen from:

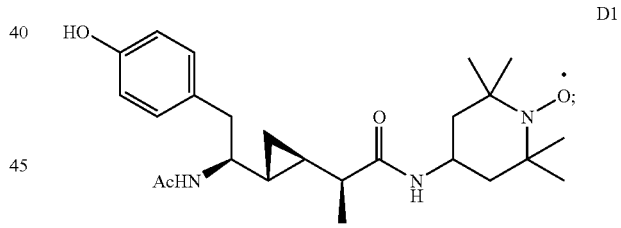
D1

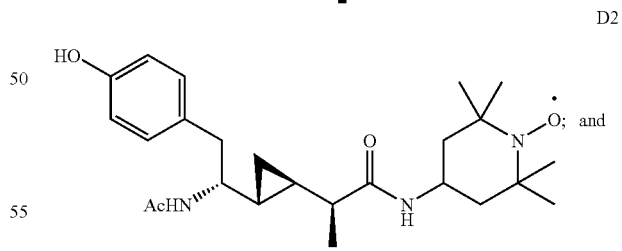
D2

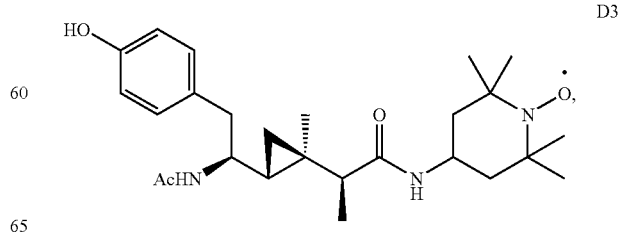
D3 wherein Ac is acetyl.

17. The compound of claim 1, wherein $R_5$ has the structure:

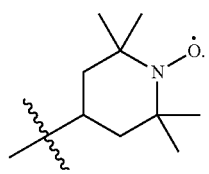

18. The compound of claim 9, wherein $R_5$ has the structure:

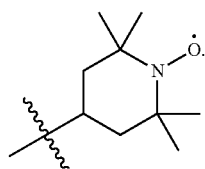

19. The compound of claim 10, wherein $R_5$ has the structure:

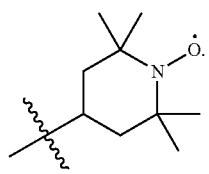

20. The compound of claim 11, wherein $R_5$ has the structure:

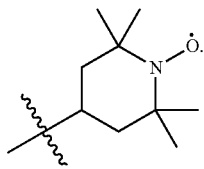

21. A pharmaceutical composition comprising a therapeutically effective amount of a compound of claim 1 and a pharmaceutically acceptable carrier.

22. A pharmaceutical composition comprising a therapeutically effective amount of a compound of claim 4 and a pharmaceutically acceptable carrier.

\* \* \* \* \*

UNITED STATES PATENT AND TRADEMARK OFFICE
CERTIFICATE OF CORRECTION

PATENT NO. : 8,288,551 B2
APPLICATION NO. : 12/505294
DATED : October 16, 2012
INVENTOR(S) : Peter Wipf et al.

It is certified that error appears in the above-identified patent and that said Letters Patent is hereby corrected as shown below:

In the Specification:

Column 14, lines 50-51, "—N—O." should be -- -N-O• --.

Column 15, line 11, "—N—O." should be -- -N-O• --.

Column 16, line 10, "—N—O." should be -- -N-O• --.

Column 27, lines 28 and 46, "—N—O." should be -- -N-O• --.

Column 29, line 4, "—N—O." should be -- -N-O• --.

Column 30, line 54, "—N—O." should be -- -N-O• --.

Column 33, lines 41 and 48, "—N—O." should be -- -N-O• --.

Column 59, line 19, after "through a pad a SiO$_2$, the" add the following text:

-- SiO$_2$ washed with CH$_2$Cl$_2$ and the colorless solution concentrated to yield 21.4 g (97%) of crude alkyne that was carried on without further purification.

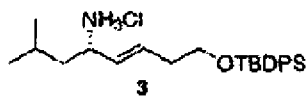

($S$,$E$)-8-($tert$-Butyldiphenylsilyloxy)-2-methyloct-5-en-4-amine hydrochloride (3) - To a solution of (2) (15.9 g, 51.5 mmol) in CH$_2$C$_2$ (300 mL) was added zirconocene hydrochloride (15.1 g, 58.4 mmol) in 3 portions and the resulting suspension was stirred at RT for 10 min. The resulting yellow solution was cooled to 0 °C and Me$_3$Al (2.0 M in hexanes, 27 .5 mL, 54.9 mmol) was added and stirred for 5 minutes followed by addition of a solution of imine (1) (6.50 g, 34.3 mmol) in CH$_2$Cl$_2$ (50 mL) and the orange solution was stirred for an additional 4 h while allowed to warm to rt. The reaction was quenched with MeOH, diluted with H$_2$0 and CH$_2$Cl$_2$ and HCl (1 M) was added to break Signed and Sealed this
Sixteenth Day of June, 2015

Michelle K. Lee
*Director of the United States Patent and Trademark Office* up the emulsion (prolonged stirring with Rochelle's salt can also be utilized). The organic layer was separated and the aqueous layer was washed with $CH_2Cl_2$ (2x). The organic layers were combined, washed with brine, dried ($MgSO_4$), filtered though a pad of Celite® and concentrated. Since the crude oil was contaminated with metal salts, the oil was dissolved in Et20 (diethyl ether, Et = ethyl), allowed to sit for 2 h, and then filtered though a pad of Celite® and concentrated. Analysis of the crude residue by IH NMR showed only 1 diastereomer (> 95:5 dr).

To the crude residue in $Et_2O$ (800 mL) was added HCl (4.0 M in dioxane, 17.2 mL, 68.7 mmol) and the reaction was stirred for 30 minutes, during which time a white precipitate formed. The precipitate was filtered, washed with dry $Et_2O$, and dried to afford 11.0 g (74% over 2 steps) of (3) as a colorless solid. mp 151-154°C;
$[\alpha]_D$-2.9 (c 1.0, $CH_2Cl_2$); $^1$H NMR δ8.42 (bs, 3 H), 7.70-7.55 (m, 4 H), 7.48-7.30 (m, 6 H),5.90 (dt, 1 H, $J$ = 14.9, 7.5 Hz), 5.52 (dd, 1 H, $J$ = 15.4, 8.4 Hz), 3.69 (appt, 3 H, $J$ = 6.5 Hz), 2.45-2.20 (m, 2 H), 1.80-1.50 (m, 3 H), 1.03 (s, 9 H), 0.95-0.84 (m, 6 H); $^{13}$C NMR δ 135.5, 134.5, 133.7, 129.5, 127.6, 127.3, 63.0, 52.9, 42.1, 35.6, 26.7, 24.4, 22.9, 21.5, 19.1; EIMS $m/z$ 395 ([M-HCl], 40), 338 (86), 198 (100); HRMS (EI) $m/z$ calcd for $C_{25}H_{37}$ NOSi (M-HCl) 395.2644, found 395.2640.

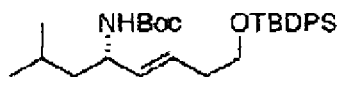

4

*(S,E)-tert*-Butyl 8-(*tert*-butyldiphenylsilyloxy)-2-methyloct-5-en-4-ylcarbamate (4) - To a solution of (3) (10.5 g, 24.3 mmol) in $CH_2Cl_2$ (400 mL) was added $Et_3N$ (triethylamine) (3.0 eq, 10.3 mL, 72.9 mmol) and $Boc_2O$ (1.05 eq, 5.74 g, 25.5 mmol) and the resulting suspension was stirred at --.

Column 81, in the first chemical structure, "NHR" should be -- NHBoc --.

Column 82, line 52, "11-Hydroxysteroid" should be -- 11-βHydroxysteroid --.

Column 84, line 13, "$NH_2OH.HCl$" should be -- $NH_2OH•HCl$ --.

Column 84, line 58, "12" should be -- $I_2$ --.

Column 85, line 18, "$Na_2WO_4.2H_2O$" should be -- $Na_2WO_4•2H_2O$ --.